(12) United States Patent  
Cambier et al.

(10) Patent No.: US 9,150,831 B2  
(45) Date of Patent: Oct. 6, 2015

(54) CONDITIONALLY IMMORTALIZED LONG-TERM STEM CELLS AND METHODS OF MAKING AND USING SUCH CELLS

(75) Inventors: John C. Cambier, Denver, CO (US); Yosef Refaeli, Denver, CO (US); Sara Ann Johnson, Denver, CO (US); Brian Curtis Turner, Denver, CO (US)

(73) Assignees: The Regents of the University of Colorado, Boulder, CO (US); National Jewish Health, Denver, CO (US)

( * ) Notice: Subject to any disclaimer, the term of this patent is extended or adjusted under 35 U.S.C. 154(b) by 0 days.

(21) Appl. No.: 12/701,383

(22) Filed: Feb. 5, 2010

(65) Prior Publication Data

US 2010/0297763 A1 Nov. 25, 2010

Related U.S. Application Data

(63) Continuation of application No. 11/583,970, filed on Oct. 18, 2006, now Pat. No. 8,883,507.

(60) Provisional application No. 60/728,131, filed on Oct. 18, 2005, provisional application No. 60/765,993, filed on Feb. 6, 2006.

(51) Int. Cl.
| | |
|---|---|
| *C12N 5/0789* | (2010.01) |
| *C07K 14/47* | (2006.01) |
| *C12N 15/62* | (2006.01) |
| *C12N 5/0735* | (2010.01) |

(52) U.S. Cl.
CPC .......... *C12N 5/0647* (2013.01); *C07K 14/4738* (2013.01); *C07K 14/4747* (2013.01); *C07K 2319/50* (2013.01); *C12N 5/0606* (2013.01); *C12N 15/62* (2013.01); *C12N 2510/04* (2013.01)

(58) Field of Classification Search
CPC .......... C07K 14/4738; C07K 14/4747; C07K 2319/50; C12N 5/0647; C12N 2510/04
See application file for complete search history.

(56) References Cited

U.S. PATENT DOCUMENTS

| | | | |
|---|---|---|---|
| 4,963,489 A | 10/1990 | Naughton et al. | |
| 5,476,996 A | 12/1995 | Wilson et al. | |
| 5,698,767 A | 12/1997 | Wilson et al. | |
| 5,811,301 A | 9/1998 | Cameron | |
| 5,824,837 A | 10/1998 | Chen et al. | |
| 5,849,288 A | 12/1998 | Reisner | |
| 6,451,558 B1 * | 9/2002 | Cooke et al. | 435/69.1 |
| 7,135,287 B1 | 11/2006 | Lonberg et al. | |
| 7,311,920 B1 | 12/2007 | Devico et al. | |
| 7,582,745 B2 | 9/2009 | Sah et al. | |
| 7,767,453 B2 | 8/2010 | Zhang et al. | |
| 8,784,825 B2 | 7/2014 | Refaeli et al. | |
| 8,828,723 B2 | 9/2014 | Refaeli et al. | |
| 2001/0049393 A1 | 12/2001 | Coller et al. | |
| 2002/0098166 A1 | 7/2002 | Havemann et al. | |
| 2003/0072794 A1 | 4/2003 | Boulikas | |
| 2003/0138859 A1 | 7/2003 | Barbera-Guillem et al. | |
| 2003/0220286 A1 | 11/2003 | Abruzzese et al. | |
| 2005/0220705 A1 | 10/2005 | Brooks et al. | |
| 2005/0281816 A1 | 12/2005 | Lamping et al. | |
| 2006/0115898 A1 | 6/2006 | Zhang et al. | |
| 2006/0154331 A1 | 7/2006 | Avidan et al. | |
| 2006/0156422 A1 | 7/2006 | Dalrymple et al. | |
| 2007/0011753 A1 | 1/2007 | Ito et al. | |
| 2007/0067854 A1 | 3/2007 | Habu et al. | |
| 2007/0093420 A1 | 4/2007 | Yeomans et al. | |
| 2007/0116691 A1 | 5/2007 | Cambier et al. | |
| 2007/0130628 A1 | 6/2007 | Brown | |
| 2007/0248618 A1 | 10/2007 | Cohen | |
| 2009/0291094 A1 | 11/2009 | Refaeli et al. | |
| 2010/0047217 A1 | 2/2010 | Refaeli et al. | |
| 2010/0055129 A1 | 3/2010 | Refaeli et al. | |
| 2010/0233804 A1 | 9/2010 | Zhou et al. | |
| 2010/0279351 A1 | 11/2010 | Refaeli | |
| 2010/0297763 A1 | 11/2010 | Cambier et al. | |
| 2011/0218210 A1 | 9/2011 | Refaeli et al. | |

FOREIGN PATENT DOCUMENTS

| | | |
|---|---|---|
| EP | 1 103 615 | 5/2001 |
| EP | 1103615 A1 | 5/2001 |
| EP | 1 357 184 | 10/2003 |
| EP | 1 792 627 | 6/2007 |
| GB | 2 387 599 | 10/2003 |
| JP | 2000-189157 | 7/2000 |
| JP | 2003-514565 | 4/2003 |
| JP | 2005-523012 | 8/2005 |
| JP | 2005-525085 | 8/2005 |
| JP | 2005-527211 | 9/2005 |
| JP | 2009-511081 | 3/2009 |
| JP | 2009-511081 A | 3/2009 |

(Continued)

OTHER PUBLICATIONS

Dang, 1999, Molecular and Cellular Biology, 19: 1-11.*
Baum et al., 2007, Current Opinion in Hematology, 14: 337-342.*
Pan et al. Mol Biol Rep 37:2117-2124, 2010.*
Huang et al. Biomaterials 33:5047-5055, 2012.*
Bunting et al., "Restoration of lymphocyte function in Janus kinase 3-deficient mice by retroviral-mediated gene transfer," Nature Medicine 4:58-64 (1998).
Chadwick et al., "Notch Signaling Induces Apoptosis in Primary Human CD34+ Hematopoietic Progenitor Cells," Stem Cells 25:203-210 (2007).

(Continued)

*Primary Examiner* — Marcia S Noble
(74) *Attorney, Agent, or Firm* — Foley & Lardner LLP

(57) ABSTRACT

Disclosed are methods for conditionally immortalizing stem cells, including adult and embryonic stem cells, the cells produced by such methods, therapeutic and laboratory or research methods of using such cells, and methods to identify compounds related to cell differentiation and development or to treat diseases, using such cells. A mouse model of acute myeloid leukemia (AML) and cells and methods related to such mouse model are also described.

9 Claims, 13 Drawing Sheets

(56) References Cited

FOREIGN PATENT DOCUMENTS

| | | |
|---|---|---|
| WO | WO-94/04686 | 3/1994 |
| WO | WO-94/19465 | 9/1994 |
| WO | WO-98/10058 | 3/1998 |
| WO | WO-98-10058 A1 | 3/1998 |
| WO | WO-99/16884 | 4/1999 |
| WO | WO-99/45962 | 9/1999 |
| WO | WO-99/53023 | 10/1999 |
| WO | WO-99-53028 A1 | 10/1999 |
| WO | WO-00/09669 | 2/2000 |
| WO | WO-00-09669 A2 | 2/2000 |
| WO | WO-00/62067 | 10/2000 |
| WO | WO-01/38548 | 5/2001 |
| WO | 2001-518300 | 10/2001 |
| WO | WO-02/057436 | 7/2002 |
| WO | WO-03/038057 | 5/2003 |
| WO | WO-03/089580 | 10/2003 |
| WO | WO 03/089580 A2 | 10/2003 |
| WO | WO-03/089630 | 10/2003 |
| WO | WO-03/097675 | 11/2003 |
| WO | WO-2005/014785 | 2/2005 |
| WO | WO 2005/084158 * | 9/2005 |
| WO | WO-2006-032876 A1 | 3/2006 |
| WO | WO-2006/116512 | 11/2006 |
| WO | WO-2007/047583 | 4/2007 |
| WO | WO-2007/067183 | 6/2007 |
| WO | WO-2008/112922 | 9/2008 |
| WO | WO-2009/059304 | 5/2009 |
| WO | WO-2009/139930 | 11/2009 |
| WO | WO-2010/011644 | 1/2010 |
| WO | WO-2010/025421 | 3/2010 |

OTHER PUBLICATIONS

Cheng et al., "BCL-2, BCL-$X_L$ Sequester BH3 Domain-Only Molecules Preventing BAX- and BAK-Mediated Mitochondrial Apoptosis," Mol Cell 8:705-711 (2001).

Conti, L. et al., "Gene therapy using neural stem cells," Methods Mol. Biol. 198:233-244 (2002).

DeoCAMPO et al., "Cooperation of bcl-2 and myc in the neoplastic transformation of normal rat liver epithelial cells is related to the down-regulation of gap junction-mediated intercellular communication," Carcinogenesis 21(8):1501-1506 (2000).

Eilers, M. et al., "Chimeras of MYC Oncoprotein and Steroid Receptors Cause Hormone-Dependent Transformation of Cells," Nature 340(6228):66-68 (1989).

Eischen et al., "Apoptosis Triggered by Myc-Induced Suppession of Bcl-$X_L$ or Bcl-2 is Bypassed during Lymphomagenesis," Mol Cell Biol 21:5063-5070 (2001).

Esdar, C. et al., "Differentiation-associated apoptosis of neural stem cells is effected by Bcl-2 overexpression: impact on cell lineage determination," Eur. J. Cell Biol. 80(8):539-553 (2001).

Felsher and Bishop, "Reversible Tumorigenesis by *MYC* in Hematopoietic Lineages," Mol Cell 4:199-207 (1999).

Gauss, "DEAE-dextran enhances electroportation of mammalian cells," Nucl Acids Res 20(24):6739-6740 (1992).

Guzman et al., "Preferential induction of apoptosis for primary human leukemic stem cells," PNAS 99(25):16220-16225 (2002).

Hoffman, "Progress in the development of systems in vitro expansion of human hematopoietic stem cells," Curr Op Hematology 6(3):14 pages (1999).

Horton, S.J. et al., "Continuous MLL-ENL expression is necessary to establish a "Hox Code" and maintain immortalization of hematopoietic progenitor cells," Cancer Res. 65(20):9245-9252 (2005).

Hoshimaru, M. et al., "Differentiation of the immortalized adult neuronal progenitor cell line HC2S2 into neurones by regulatable suppression of the V-MYC oncogene," Proceedings of the National Acadamy of Sciences of USA 93(4):1518-1523 (1996).

Howard, M.J. et al., "Transplantation of apoptosis-resistant embryonic stem cells into the injured rat spinal cord," Somatosensory & Motor Research 22(1-2):37-44 (2005).

Korbling et al., "Allogeneic Blood Stem Cell Transplantation: Peripheralization and Yield of Donor-Derived Primitive Hematopoietic Progenitor Cells (CD34+ Thy-$1^{dim}$) and Lymphoid Subsets, and Possible Predictors of Engraftment and Graft-Versus-Host Disease," Blood 86:2842-2848 (1995).

Krosl et al., "In vitro expansion of hematopoietic stem cells by recombinant TAT-HOXB4 protein," Nature Med 9(11):1428-1432 (2003).

McCarthy, "Underground movement," Nature Reviews Cancer 7:1 page (2007).

MacPherson, P. et al., "Activity-dependent gene regulation in conditionally-immortalized muscle precursor cell lines," J. Cell. Biol. 91(4):821-839 (2004).

Melkonyan et al., "Electroporation efficiency in mammalian cells is increased by dimethyl sulfoxide (DMSO)," Nucl. Acids Res. 24:4356-4357 (1996).

Miller et al., "Expansion in vitro of adult murine hemapoietic stem cells with transplantable lympho-myeloid reconstituting ability," PNAS USA 94:13648-13653 (1997).

Mooslehner et al., "Retroviral Integration Sites in Transgenic Mov Mice Frequently Map in the Vicinity of Transcribed DNA Regions," J Virol 64:3056-3058 (1990).

Moore et al., "In Vitro Maintenance of Highly Purified, Transplantable hematopoietic Stem Cells," Blood 89(12):4337-4347 (1997).

Pierelli et al., "Modulation of bcl-2 and p27 in human primitive proliferating hematopoietic progenitors by autocrine TGF-β1 is a cell cycle-independent effect and influences their hematopoietic potential," Blood 95:3001-3010 (2000).

Pinto et al., "Hematopoietic progenitor/stem cells immortalized by Lhx2 generate functional hematopoietic cells in vivo," Blood 99(11):3939-3946 (2002).

Pollock, K. et al., "A conditionally immortal clonal stem cell line from human cortical neuroepithelium for the treatment of ischemic stroke," Exp. Neurology 199(1):143-155 (2006).

Raymon, H.K. et al., "Immortalized human dorsal root ganglion cells differentiate into neurons with nociceptive properties," J. Neuroscience 19(13):5420-5428 (1999).

Richter et al., "Lhx2 expression in hematopoietic progenitor/stem cells in vivo causes a chronic myeloproliferative disorder andaltered globin expression," J Hematology 88(12):1336-1347 (2003).

Rosenwald et al., "Increased expression of eukaryotic translation initiation facots eIF-4E and eIF-2alpha in response to growth induction by c-myc," PNAS USA 90:6175-6178 (1993).

Sauer, "Inducible Gene Targeting in Mice Using the Cre/*lox* System," Methods: A Comparison to Methods in Enzymology 14:381-392 (1998).

Schroy and Todd, "A Simple Method for Freezing and Thawing Cultured Cells," Methods in Cell Science 2:309-310 (1976).

Schwarze et al., "Protein transduction: unrestricted delivery into all cells?" Trends in Cell Biology 10:290-295 (2000).

Sipone, S. et al., "Modeling brain pathologies using neural stem cells," Methods Mol. Biol. 198:245-262 (2002).

Takahashi et al., "Induction of Pluripotent Stem Cells from Mouse Embryonic and Adult Fibroblast Cultures by Defined Factors," Cell 126:663-676 (2006).

Tsai et al., "Lymhohematopoietic progenitors immortalized by a retroviral vector harboring a dominant-negative retinoic acid receptor can recapitulate lymphoid, myeloid, and erythroid development," Genes & Dev. 8:2831-2841 (1994).

Varnum-Finney et al., "Pluripotent, cytokine-dependent, hematopoietic stem cells are immortalized by constitutive Notch 1 signaling," Nature Medicine 6(11):1278-1281 (2000).

Vaux et al., "Bc1-2 gene promotes heamopoietic cell survival and cooperates with c-myc to immortalize pre-B cells," Nature 335:440-442 (1988).

Wang et al., "Primitive Human Hematopoietic Cells are Enriched in Cord Blood Compared With Adult Bone Marrow or Mobilized Peripheral Blood as Measured by the Quantitative In Vivo SCID-Repopulating Cell Assay," Blood 89:3919-3924 (1997).

Wikipedia [online], 2008, [retrieved on Nov. 13, 2008], Retrieved from Internet: URL:http://en.wikipedia.org/wiki/Stem_cell, pp. 1-11.

(56) References Cited

OTHER PUBLICATIONS

Wilson et al., "c-Myc controls the balance between hematopoietic stem cell self-renewal and differentiation," Genes and Development 18:2474-2763 (2007).
Wurm and Bernard, "Large-scale transient expression in mammalian cells for recombinant protein production," Curr Op Biotech 10:156-159 (1999).
Yanai et al., "A novel stromal cell-dependent hematopoietic cell line established from temperature-sensitive SV40 T-antigen transgenic mice," Exp Hematology 27:1087-1096 (1999).
PCT/US06/40379 Search Report dated Apr. 23, 2008.
PCT/US06/40379 Search Report and Written Opinion mailed Sep. 24, 2007.
U.S. Appl. No. 12/467,957 Office Action mailed Feb. 28, 2011.
U.S. Appl. No. 12/467,957 Office Action mailed Oct. 13, 2010.
U.S. Appl. No. 12/048,148 Office Action mailed Jan. 19, 2011.
U.S. Appl. No. 11/583,970 Office Action mailed Nov. 4, 2009.
U.S. Appl. No. 11/583,970 Office Action mailed Mar. 23, 2009.
U.S. Appl. No. 11/583,970 Office Action mailed Nov. 26, 2008.
U.S. Appl. No. 11/583,970 Office Action mailed Mar. 12, 2008.
EP 08743862 Supplementary Search Report dated Feb. 9, 2010.
PCT/US08/56896 Written Opinion dated Jul. 18, 2008.
PCT/US08/56896 Internationl Preliminary Report on Patentability dated Sep. 15, 2009.
EP08743862 Office Action dated May 14, 2010.
Buske et al., "Deregulated expression of HOXB4 enhances the primitive growth activity of human hematopoietic cells," Blood, Aug. 1, 2002, pp. 862-868, vol. 100, No. 3.
Capecchi, Mario, "Altering the genome by homologous recombination," Science, 1989, pp. 1288-1292, vol. 244.
Chin et al., "Essential role of oncogenic Ras in tumour maintenance," Nature, Jul. 29, 1999, pp. 468-472, vol. 400, Macmillan Magazines Ltd.
Choi et al., "Myc protein is stabilized by suppression of a novel E3 ligase complex in cancer cells," Genes & Development, 2010, pp. 1236-1241, vol. 24, downloaded Aug. 10, 2011.
File History, U.S. Appl. No. 11/583,970, filed Oct. 18, 2006.
Hann et al., "Proteins encoded by the human c-*myc* oncogene: Differential expression in neoplastic cells," Molecular and Cellular Biology, Nov. 1984, pp. 2486-2497, vol. 4, No. 11.
Huettner et al., "Reversibility of acute B-cell leukaemia induced by *BCR-ABL1*," Nature Genetics, Jan. 2000, pp. 57-60, vol. 24, Nature America, Inc.
Office Action dated Dec. 31, 2010, received in Chinese Appl. No. 200680045545.8.
Office Action dated May 9, 2011, received in U.S. Appl. No. 11/583,970.
Restriction Requirement dated Nov. 13, 2007, received in U.S. Appl. No. 11/583,970.
Schiedlmeider et al., "High-level ectopic HOXB4 expression confers a profound in vivo competitive growth advantage on human cord blood CD34+ cells, but impairs lymphomyeloid differentiation," Blood, Mar. 1, 2003, pp. 1759-1768, vol. 101, No. 5.
Office Action dated Sep. 20, 2013 in U.S. Appl. No. 11/583,970, filed Oct. 18, 2006.
Australian Search Report and Written Opinion received for Singapore Patent Application No. 201101367-9, mailed on Mar. 23, 2012, 17 pages.
Beerens et al., "Protein Transduction Domains and their Utility in Gene Therapy", Current Gene Therapy, vol. 3, No. 5, 2003, pp. 486-494.
Berkson et al., "Pilot Screening Programme for Small Molecule Activators of p53", International Journal of Cancer, vol. 115, 2005, pp. 701-710.
Caron, et al., "Endosome distruption enhances the functional nuclear delivery of Tat-fusion proteins", Biochem Biophys Res Commun, (2004), vol. 319, pp. 12-20.
Carotta et al., "Directed Differentation and Mass Cultivation of Pure Erythorid Progenitors from Mouse Embryonic Stem Cells", Blood, vol. 104, No. 6, Sep. 15, 2004, pp. 1873-1880.

Chen et al., "Small-Molecule Anthracene-Induced Cytotoxicity and Induction of Apoptosis through Generation of Reactive Oxygen Species", Biological & Pharmaceutical Bulletin, vol. 27, No. 6, Jun. 2004, pp. 838-845.
Coller, et al., "Expression Analysis with Oligonucleotide Microarrays Reveals that MYC Regulates Genes Involved in Growth, Cell Cycle, Signaling, and Adhesion", PNAS, (2000), 97(7):3260-3265.
Dang et al., "Identification of the Human c-myc Protein Nuclear Translocation Signal", Molecular and Cellular Biology, vol. 8, No. 10, Oct. 1998, pp. 4048-4054.
English Translation of Fourth Office Action received for Chinese Patent Application No. 200880015602.7 dated Nov. 11, 2013, 6 pages.
English Translation of Office Action received for Eurasion Patent Application No. 201001762/28, posted Oct. 16, 2013, 1 page.
English translation of Office Action received for Israeli Patent Application No. 190946, dated Apr. 22, 2013, 1 page.
English Translation of Office Action received for Israeli Patent Application No. 209968 dated Jan. 2, 2014, 2 pages.
English translation of Office Action received for Japanese Application No. 2008-536713 dated Aug. 5, 2013, 2 pages.
English Translation of Office Action received for Korean Patent Application No. 10-2008-7011791 dated Jan. 15, 2014, 3 pages.
English Translation of Office Action received for Korean Patent Application No. 10-2013-7028338, dated Jan. 15, 2014, 3 pages.
English Translation of Second Office Action received for Chinese Patent Application No. 200980127166.7, dated Jun. 10, 2013, 1 page.
Extended Eiropean Search Report and Search Opinion received for Patent Application No. 1217097.6, mailed on Mar. 27, 2013, 8 pages.
Extended European Search Report received for European Patent Application No. 09810692.5, mailed on Jul. 11, 2011, 5 pages.
Extended European Search Report received for European Patent Application No. 09747016.5, mailed on May 30, 2012, 8 pages.
Extended European Search Report received for European Patent Application No. 09800871.7, mailed on Jun. 24, 2011, 5 pages.
Extended European Search Report received for European Patent Application No. 12187077.8, mailed on Mar. 25, 2013, 7 pages.
Final Office Action received for Korean Patent Application No. 10-2009-7021320, mailed on May 29, 2013, 6 pages (3 pages of English Translation and 3 pages of Office Action).
Final Office Action received for U.S. Appl. No. 12/048,146, mailed on Feb. 15, 2013, 17 pages.
Final Office Action received for U.S. Appl. No. 12/550,166, mailed on May 11, 2012, 12 pages.
Habib et al., "Myc Stimulates B Lymphocyte Differentiation and Amplifies Calcium Signaling", J.Cell Biol., vol. 179, No. 4, 2007, pp. 717-731.
Hiramatsu et al., "Complete Reconstitution of Human Lymphocytes from Cord Blood CD34 Cells Using the NOD/SCID/ycnull Mice Model", Blood. vol. 102, No. 3, 2003, pp. 873-880.
Huang et al., "Dynamic Regulation of C-Myc Proto-Oncogene Expression during Lymphocyte Development Revealed by GFP-c-Myc Knock-In Mouse", Eur. J. Immunol., vol. 38, No. 2, 2008, pp. 342-349.
International Preliminary Report on Patentability received for PCT Patent Application No. PCT/US2008/082263, issued on May 4, 2010, 6 pages.
International Preliminary Report on Patentability received for PCT Patent Application No. PCT/US2009/003105, issued on Nov. 17, 2010, 6 pages.
International Preliminary Report on Patentability received for PCT Patent Application No. PCT/US2009/051242, issued on Jan. 25, 2011, 6 pages.
International Preliminary Report on Patentability received for PCT Patent Application No. PCT/US2009/055443, issued on Mar. 1, 2011, 6 pages.
International Search Report and Written Opinion received for PCT Patent Application No. PCT/US2008/056896 mailed on Aug. 14, 2008, 5 pages.
International Search Report and Written Opinion received for PCT Patent Application No. PCT/US2008/082263, mailed on Jun. 25, 2009, 8 pages.

(56) References Cited

OTHER PUBLICATIONS

International Search Report and Written Opinion received for PCT Patent Application No. PCT/US2009/003105, mailed on Jan. 15, 2010, 9 pages.
International Search Report and Written Opinion received for PCT Patent Application No. PCT/US2009/051242, mailed on Feb. 19, 2010, 9 pages.
International Search Report and Written Opinion received for PCT Patent Application No. PCT/US2009/055443, mailed on Jun. 30, 2010, 11 pages.
Ju, et al., "Anti-Apoptotic Therapy with a Tal Fusion Protein Protects Against Excitotoxic Insults in Vitro and in Vivo", Experimental Neurology, vol. 210, 2008, pp. 602-607.
Kelso et al., "Survival of the Myeloid Progenitor Cell Line FDC-P1 is Prolonged by Inferon-γ or Interleukin-4", Growth Factors, vol. 6, No. 3, 1992, pp. 233-242.
Li et al., "Reconstitution of Functional Human B Lymphocytes in NOD/SCID Mice Engrafted with ex vivo Expanded CD34 Cord Blood Cells", Experimental Hematology, vol. 30, 2002, pp. 1036-1043.
Littlewood, et al., "A modified oestrogen receptor ligand-binding domain as an improved switch for the regulation of heterologous proteins", Nucleic Acids Research, (1995), vol. 23, No. 10, pp. 1686-1690.
Muchimore et al., "X Ray and NMR Structure of Human Bcl-xL, an Inhibitor of Programmed Cell Death", Nature, vol. 381, May 23, 1996, pp. 335-341.
Non Final Office Action received for U.S. Appl. No. 12/048,148, mailed on Oct. 13, 2011 9 pages.
Non Final Office Action received for U.S. Appl. No. 12/962,197, mailed on Aug. 26, 2011, 11 pages.
Non-Final Office Action received for U.S. Appl. No. 12/048,148, mailed on May 11, 2012, 9 pages.
Non-Final Office Action received for U.S. Appl. No. 12/506,894, mailed on Apr. 27, 2012, 13 pages.
Non Final Office Action received for U.S. Appl. No. 12/550,166 mailed on Jan. 11, 2012, 7 pages.
Notice of Allowance recieved for U.S. Appl. No. 12/550,166, mailed on Nov. 26, 2012, 9 pages.
Office Action received for Australian Patent Aplication No. 2009285547, mailed on Jul. 25, 2011, 2 pages.
Office Action received for Canadian Patent Application No. 2731767, mailed on Jul. 25, 2012, 3 pages.
Office Action received for Canadian Patent Application No. 2735522, mailed on Sep. 10, 2012, 3 pages.
Office action received for Chinese Patent Application No. 200880015602.7, mailed on Jan. 31, 2012, 16 pages (10 pages of English translation and 6 pages of Office Action).
Office Action received for Chinese Patent Application No. 200880015602.7, mailed on May 9, 2013, 13 pages (8 pages of English Translation and 5 pages of Official copy).
Office Action received for Chinese Patent Application No. 200880015602.7, mailed on Oct. 31, 2012, 10 pages (6 pages of English Translation and 4 pages of Chinese Action).
Office Action received for Chinese Patent Application No. 200980126312.4, issued on Aug. 28, 2012, 12 pages (6 pages of English Translation and 6 pages of Office Action).
Office Action received for Chinese Patent Application No. 200980127166.7 mailed on Dec. 5, 2012, 4 pages (1 page of English Translation and 3 pages of Office Action).
Office Action received for Chinese Patent Application No. 200980126312.4, mailed on Jan. 30, 2012, 14 pages (7 pages of English translation and 7 pages of Office Action).
Office Action received for Euopean Patent Application No. 08743852.8, mailed on Sep. 23, 2010, 6 pages.
Office Action received for European Patent Application No. 09747016.5, mailed on Apr. 9, 2013, 6 pages.
Office Action received for European Patent Application No. 09810692.5, mailed on Mar. 28, 2012, 3 pages.

Office Action received for Israel Patent Application No. 200919, mailed on Jan. 17, 2013, 4 pages (2 pages of English Translation and 2 pages of Official Copy).
Office Action received for Israel Patent Application No. 209343, mailed on Aug. 14, 2012, 3 pages (2 pages of English Translation and 1 page of Office Action).
Office Action received for Israel Patent Application No. 209968, mailed on Aug. 21, 2012, 4 pages (2 pages of English Translation and 2 pages of Office Action).
Office Action received for Israel Patent Application No. 200919, mailed on Dec. 5, 2011, 2 pages of English Translation only.
Offiec Action received for Israeli Patent Application No. 208810, mailed on Jan. 2, 2013, 4 pages (English Translation only).
Office Action received for Japanese Application No. 2011-520133, dated Feb. 5, 2014, 4 pages (in Japanese).
Office Action received for Japanese Patent Application No. 2009-553785, mailed on Jun. 19, 2012, 6 pages of English Translation and 4 pages of Office Action).
Office Action received for Korean Patent Application No. 10-2008-7011791, dated May 28, 2013, English translation, 3 pages.
Office Action received for Korean Patent Application No. 10-2009-7021320, mailed on Jul. 29, 2011, 7 pages (3 pages of English Translation and 4 pages of Office Action).
Office Action received for Korean Patent Application No. 10-2009-7021320, mailed on Sep. 18, 2012, 11 pages (7 pages of English Translation and 4 pages of Office Action).
Oral Proceedings Summons received for European Patent Application No. 08743862.8, mailed on May 14, 2012, 6 pages.
Podsypanina, K. et al., "Oncogene cooperation in tumor maintenance and tumor recurrence in mouse mammary tumors induced by MYC and mutant Kras," PNAS 105(13):5242-5247 (2008).
Qin et al., "Nuclear Factor KB Nuclear Translocation Upregulates c-Myc and p53 Expression during NMDA Receptor-Mediated Apoptosis in Rat Striatum", The Journal of Neuroscience, vol. 19, No. 10, May 15, 999, pp. 4023-4033.
Radhakrishnan et al., "A Novel Transcriptional Inhibitor Induces Apoptosis in Tumor Cells and Exhibits Antiangiogenic Activity", Cancer Research, vol. 66, No. 6, Mar. 15, 2006, pp. 3264-3270.
Refaeli, et al., "The protooncogene MYC can break B cell tolerance," PNAS, (2005), 102(11):4097-4102.
Refaeli, Y, "The B-Cell Antigen Receptor and Overexpression of MYC Can Cooperate in the Genesis of B-Cell Lymphomas", PLOS Biology, vol. 6, No. 6, e152, 2008. pp. 1208-1225.
Roh, M. et al., "Transgenic Mice for Cre-Inducible Overexpression of the Oncogenes c-MYC and Pim-1 in Multiple Tissues," Genesis 44:447-453 (2006).
Schmidt, et al., "Transgenic mice bearing the human c-myc gene activated by an immunoglobulin enhancer: A pre-B-cell lymphoma model," PNAS USA. (1988), 85:6047-6051.
Soane,L., et al., "TAT-mediated endocytotic delivery of the loop deletion Bcl-2 protein protects neurons against cell death", Journal of Neurochemistry, (2005), vol. 95, pp. 230-243.
Thomas, et al., "Progress and Problems with the Use of Viral Vectors for Gene Therapy", Nature, (May 2003), vol. 4, pp. 346-358.
Yagihashi, et al., "Detection of Anti-Survivin Antibody in Gastrointestinal Cancer Patients", Clinical Chemistry, (2001), vol. 47, No. 9, pp. 1729-1731.
Young et al., "B-Cell Receptor Signaling in the Genesis and Maintenance of B-Cell Lymphoma", Future Oncology, vol. 4, No. 5, 2008, pp. 591-594.
Zhang et al., "Cytokines Regulating Hematopoietic Stem Cell Function", Current Opinion Hematology, vol. 15, No. 4, Jul. 2008, pp. 307-311.
Patent Examination Report dated Jul. 16, 2012, issued in connection with Australian Patent Application No. 2006304392.
Decision of Rejection dated Jul. 3, 2012, issued in connection with Chinese Patent Application No. 200680045545.8.
English translation of Decision of Rejection dated Jul. 3, 2012, issued in connection in connection with Chinese Patent Application No. 200680045545.8.
Office Action dated Jul. 3, 2012, issued in connection with Japanese Patent Application No. 2008-536713.
Office Action received in CN 200680045545.8.

(56) References Cited

OTHER PUBLICATIONS

English translation of Office Action received in CN 20060045545.8.
Notification of Defects dated Jul. 3, 2012, issued in connection with Israeli Patent Application No. 190946.
Office Action dated Apr. 17, 2013 received in Cambodian Application 2,626,525.
Office Action dated May 28, 2013 in Korean Patent Application No. 10-2008-7011791 (with English translation).
Decision of Rejection dated Aug. 5, 2013 for Japanese Patent Application 2008-536713 (with English translation).
First Examination Report dated Aug. 23, 2013 for Indian Patent Application 3332/DELNP/2008.
Response to Office Action filed Feb. 16, 2012, in U.S. Appl. No. 11/583,970.
Aubry et al., "N-Myc Shares Cellular Functions with c-Myc," DNA and Cell Biology, 19:353-364 (2000).
Merino, et al., "Development Regulation of the Bcl-2 Protein and Susceptibility to Cell Death in B Lymphocytes," EMBO J. 13:683-91 (1994).
Office Action dated Sep. 1, 2009, received in EP Appl. No. 6826025 (Publ. No. 1942739).
Office Action dated Sep. 22, 2009, received in EP Appl. No. 6826025 (Publ. No. 1942739).
Office Action dated Nov. 17, 2011, received in U.S. App. No. 11/583,970.
Supplementary European Search Report dated Aug. 13, 2009, EP Appl. No. 6826025.
Choi, et al., "Status Epilepticus-Induced Somatostatinergic Hilar Interneuron Degeneration is Regulated by Striatal Enriched Protein Tyrosine Phosphatase", Journal of Neuroscience, (2007), vol. 27, No. 11, pp. 2999-3009.
English Translation of Office Action received for Chinese Patent Application No. 200980126312.4 dated Jan. 22, 2014, 3 pages.
English Translation of Office Action received for Japanese Patent Application No. 2011-525258 dated Feb. 17, 2014, 4 pages.
Ho, et al., "Synthetic Protein Transduction Domains: Enhanced Transduction Potential in Vitro and in Vivo", Cancer Research, (2001), vol. 61, pp. 474-477.
Iritani, et al., "c-Myc enhances protein synthesis and cell size during B lymphocyte development", PNAS, (1999), vol. 96, No. 23, pp. 13180-13185.
Jadlowsky, et al., "Dominant negative mutant Cyclin T1 proteins inhibit HIV transcription by specifically degrading Tat", Retrovirology, (2008), vol. 5, Article 63, 12 pages.
Kashio, et al., "A Protein Derived From the Fusion of TAT Peptide and FNK, a Bcl-xL Derivative, Prevents Cochlear Hair Cell Death From Aminoglycoside Ototoxicity In Vivo", Journal of Neuroscience Research, (2007), vol. 85, No. 7, pp. 1403-1412.
Kitada, et al., "Reversal of Chemoresistance of Lymphoma Cells by Antisense-Mediated Reduction of bcl-2 Gene Expression", Antisense Research and Development, (1994), vol. 4, pp. 71-79.
Non-final Office Action on U.S. Appl. No. 12/467,957 dated Apr. 4, 2014, 14 pages.
Non-final Office Action on U.S. Appl. No. 13/795,659 dated Mar. 10, 2014, 11 pages.
Non-final Office Action on U.S. Appl. No. 13/797,648 dated Apr. 3, 2014, 13 pages.
Office Action received for Australian Patent Application No. 2009246876 dated Jan. 17, 2014, 6 pages.
Office Action received for European Application No. 09810692.5 dated Feb. 25, 2014, 3 pages.
Rabbitts, et al., "Metabolism of c-myc gene products: c-myc mRNA and protein expression in the cell cycle", EMBO Journal, (1985), vol. 4, No. 8, pp. 2009-2015.
Snyder, et al., "Regulation of NMDA receptor trafficking by amyloid-3B2", Nature Neuroscience, (2005), vol. 8, No. 8, pp. 1051-1058.

Theis, et al., "Expression of the myc/His-Tagged Human Peptide Transporter hPEPT1 in Yeast for Protein Purification and Functional Analysis", Protein Expression and Purification, (2001), vol. 22, pp. 436-442.
Vaux, et al., "Immunologic competence of B cells subjected to constituive c-myc oncogene expression in immunoglobulin heavy chain enhancer myc transgenic mice", J. Immunol., (1987), vol. 139, No. 11, pp. 3854-3860.
Deocampo, et al., "Cooperation of BCL-2 and MYC in the Neoplastic Transformation of Normal Rat Liver Epithelial Cells is Related to the Down-Regulation of Gap Junction-Mediated Intercellular Communication", Carcinogenesis, vol. 21, No. 8, pp. 1501-1506, (2000).
English Translation of Notification of Reasons of Refusal for Japanese Patent Application No. 2012-221023 dated Jun. 24, 2014, 2 pages.
English Translation of Office Action on Chinese Application No. 200980127166.7 dated Apr. 11, 2014, 3 pages.
English Translation of Office Action on Japanese Patent Application No. 2012-221023 dated Apr. 22, 2014, 3 pages.
English Translation of Third Office Action on Japanese Patent Application No. 2009-553785 dated Apr. 22, 2014, 3 pages.
Examination Report for Indian Patent Application No. 3332/DELNP/2008 dated Aug. 23, 2013, 6 pages.
Examination Report on Australian Patent Application No. 2012216462 dated Mar. 6, 2014, 3 pages.
Final Office Action on U.S. Appl. No. 11/583,970 dated Apr. 9, 2014, 20 pages.
Gauss et al., "DEAE-Dextran Enhances Electroportation of Mammalian Cells", Nucleic Acids Research, vol. 20, No. 4, pp. 6739-6740 (1992).
Jayapal et al., "Down-regulation of Myc is Essential for Terminal Erythroid Maturation" The Journal of Biological Chemistry, vol. 285, No. 51, pp. 40252-40265, Dec. 17, 2010.
Notice of Allowance on U.S. Appl. No. 12/550,166 dated Apr. 28, 2014, 4 pages.
Notification prior to Allowance of Israeli Patent Application No. 209343 dated Apr. 7, 2014, 2 pages.
Office Action on Canadian Application No. 262,525 dated Apr. 8, 2014, 4 pages.
Office Action on Canadian Patent Application No. 2,680,613 dated Nov. 21, 2013, 3 pages.
Rosenwald, et al., "Increased Expression of Eukaryotic Translation Inhibition Factors eIF-4E and eIF-2alpha in Response to Growth Induction by C-MYC", Proc. Natl. Acad. Sci. USA. vol. 90, pp. 6175-6178, (1993).
Wilson, et al., "c-MYC Controls the Balance Between Hematopoletic Stem Cell Self-Renewal and Differentiation" Genesand Development. vol. 18, pp. 2747-2763 (2007).
Dvorak et al., "Cytochemical Localization of Peroxidase Activity in the Developing Erythrocyte," Am. J. Pathol, 1972, 67(2), pp. 303-326.
Examination Report on Australian Application 2009274172, mailed Jul. 24, 2014.
International Search Report and Written Opinion for International Application No. PCT/US2014/022971 dated Aug. 13, 2014, 12 pages.
International Search Report and Written Opinion on PCT/US2014/022977, mailed Aug. 28, 2014.
Notice of Allowance on U.S. Appl. No. 11/853,970, mailed Aug. 29, 2014.
Xi et al., "In Vitro Large Scale Production of Human Mature Red Blood Cells From Hematopoietic Stem Cells by Coculturing with Human Fetal Liver Stromal Cells," Biomed. Res. Int. Epub Jan. 30, 2013, 2013:807863, 12 pages.
Dang et al., "Nuclear and Nucleolar Targeting Sequences of c-erb-A, c-myb, N-myc, p53, HSP70 and HIV tat Proteins", Journal of Biological Chemistry, vol. 264, No. 30, pp. 18019-18023 (1989).
English Translation of Office Action on Israeli Patent Appliction No. 200919 dated May 19, 2014, 3 pages.
Extended European Search Report for EP Patent Application No. 13188850.0, dated May 27, 2014, 8 pages.

(56) References Cited

OTHER PUBLICATIONS

English Translation of Office Action on Korean Patent Application No. 10-2013-7020078 dated Sep. 17, 2014, 5 pages.
Examination Report on Canadian Application 2,731,767, mailed Sep. 5, 2014, 2 pages.
Final Office Action on U.S. Appl. No. 12/467,957, mailed Sep. 17, 2014, 9 pages.
Final Office Action on U.S. Appl. No. 12/506,894 dated Oct. 9, 2014, 15 pages.
Miharada et al., "Efficient enucleation of erythroblasts differentiated in vitro from hematopoietic stem and progenitor cells", Nature Biotechnology, 24(10): 1255-1256, 2006.
Examination Report on Canadian Application No. 2,735,522 dated Oct. 2, 2014, 2 pages.
Dang et al., "Nuclear and Nucleolar Targeting Sequences of c-erb-A, c-myc, N-myc, p53, HSP70 and HIV tat Proteins", Journal of Biological Chemistry, vol. 264, No. 30, pp. 18019-18023 (1989).
English Translation of Office Action on Israeli Patent Application No. 200919 dated May 19, 2014, 3 pages.
Extended European Search Report for EP Patent Application No. 1318850.0, dated May 27, 2014, 8 pages.
Final Office Action on U.S. Appl. No. 13/795,659 dated Jul. 11, 2014, 16 pages.
Notice of Allowance on U.S. Appl. No. 13/777,967 dated Jul. 14, 2014, 56 pages.
International Search Report and Written Opinion for International Application No. PCT/US2013/051384, mail date Nov. 13, 2013, 15 pages.
Johnson, N.A. et al., "Lymphomas with concurrent BCL2 and MYC translocations: the critical factors associated with survival", Blood, 2009, vol. 114, No. 11, pp. 2273-2279.
Levesque, J-P et al., "The endosteal 'osteoblastic' niche and its role in hematopoietic stem cell homing and mobilization", Leukemia, 2010, vol. 24, pp. 1979-1992.
Wilson A., et al., c-Myc controls the balance between hematopoietic stem cell self-renewal and differentiation. Genes Dev. 18:2747-63 (2004).
Official Action on European Application No. 09810692.5 dated Oct. 22, 2014, 3 pages.
Notice of Allowance on U.S. Appl. No. 12/467,957, mailed Nov. 26, 2014, 7 pages.
English Translation of Decision of Rejection on Japanese Application No. 2011-520133, mail date Nov. 26, 2014, 6 pages.
Non-Final Office Action on U.S. Appl. No. 13/795,659 dated Nov. 26, 2014, 13 pages.
Examiner's Report on Canadian Application No. 2680613 dated Nov. 28, 2014, 4 pages.
English Translation of Decision of Rejection on Japanese Application No. 2011-525258, mail date Dec. 3, 2014, 11 pages.
Examiner's Reort on European Application No. 12187097.6 dated Jan. 22, 2015, 6 pages.
International Preliminary Report on Patentability for International Application No. PCT/US2013/051384, mail date Jan. 29, 2015, 12 pages.
English Translation of Office action on Israeli Application No. 208810 dated Jan. 13, 2015, 3 pages.
English Translation of the Third Office Action on Chinese Patent Application No. 200680045545.8 dated Feb. 15, 2015, 4 pages.
Bouchard et al., "Control of cell proliferation by Myc", Trends in Cell Biology, vol. 8, pp. 202-206, (1998).
English Translation of Office Action on Israeli Application No. 232432 dated Mar. 8, 2015, 3 pages.
Examination Report on European Application No. 09747016.5 dated Mar. 19, 2015, 5 pages.
Final Office Action on U.S. Appl. No. 13/795,659 dated Mar. 26, 2015, 18 pages.
Final Office Action on U.S. Appl. No. 13/797,648 dated Apr. 1, 2015, 12 pages.
Non-Final Office Action on U.S. Appl. No. 12/506,894 dated Apr. 3, 2015, 16 pages.
Notice of Acceptance of Australian Application No. 2009246876 dated Apr. 2, 2015, 3 pages.
Wechsler et al., "MXI1, a Putative Tumor Suppressor Gene, Supresses Growth of Human Glioblastoma Cells", Cancer Research 57, pp. 4405-4912, (1997).

\* cited by examiner

CONDITIONALLY IMMORTALIZED LONG-TERM STEM CELLS AND METHODS OF MAKING AND USING SUCH CELLS

RELATED APPLICATIONS

This application is a continuation of U.S. patent application Ser. No. 11/583,970, entitled "CONDITIONALLY IMMORTALIZED LONG-TERM STEM CELLS AND METHODS OF MAKING AND USING SUCH CELLS" filed Oct. 18, 2006, which is herein incorporated by reference in its entirety.

CROSS-REFERENCE TO RELATED APPLICATIONS

This application claims the benefit of priority under 35 U.S.C.§119(e) from U.S. Provisional Patent Application No. 60/728,131, filed Oct. 18, 2005, and from U.S. Provisional Application No. 60/765,993, filed Feb. 6, 2006. The entire disclosure of each of U.S. Provisional Patent Application No. 60/728,131 and U.S. Provisional Patent Application No. 60/765,993 is incorporated herein by reference.

SEQUENCE LISTING

The instant application contains a Sequence Listing which has been submitted via EFS-Web and is hereby incorporated by reference in its entirety. Said ASCII copy, created on May 10, 2010, is named 36824701.txt, and is 121,120 bytes in size.

FIELD OF THE INVENTION

The present invention generally relates to conditionally immortalized long term stem cells, to methods of producing such cells, and to methods of using such cells, including therapeutic methods and drug discovery methods.

BACKGROUND OF THE INVENTION

The ability to manipulate the bone marrow output of various blood cells has become an important tool in the management of several diseases. Some of the best new therapies for hematological malignancies are based on the development of compounds that push leukemic cells to differentiate into lineages to which they are committed prior to the transforming event. One such example is the case of acute promyelocytic leukemia. Upon treatment of patients with Arsenic Trioxide, the malignant cells are pushed along the myelomonocytic pathway leading to remission of those tumors. Another example lies in promotion of successful engraftment of transplanted bone marrow stem cells (long term reconstituting hematopoietic stem cells, or lt-HSC) in irradiated individuals. The appearance of differentiated blood cells can be accelerated by the systemic administration of cytokines that are known to specifically induce red blood cell development (erythropoietin, or Epo), or myeloid cell development (granulocyte-macrophage colony-stimulating factor, or GM-CSF). Finally, harvesting of lt-HSC from donors has been greatly simplified by the process of "mobilization" wherein these cells are induced to move from the bone marrow sites where they normally reside into peripheral blood by systemic administration of a cytokine called G-CSF. Stem cells can then by harvested from peripheral blood obviating the painful and elaborate collection of bone marrow biopsies. All of these processes rely on the ability to program and control the biological behavior of lt-HSC.

Accordingly, bone marrow (stem cell) transplantation is an invaluable therapeutic tool for hematologic and immune reconstitution of individuals who have undergone radiation and/or chemotherapy (e.g. cancer patients, or have been exposed to high-level radiation), and is also a critical modality for treatment of immune deficiency and hematological malignancies. In addition, bone marrow transplantation would be a highly useful therapy to combat the negative effects of aging on the immune system, as well as on other cells and tissues. It is estimated that stem cell transplantation could benefit more than 35,000 children and adults per year.

The operative principle behind bone marrow transplantation is replacement of radiation sensitive lt-HSC that give rise to all blood cell types. Recent studies indicate that bone marrow transplantation may have value in the treatment of heart disease. Although the basis of this affect is unknown, it, and other findings, raise the possibility that hematopoietic stem cells (lt-HSC) may be reprogrammed to give rise to other tissues. If this is true, lt-HSC may have much broader utility and provide an alternative to controversial embryonic stem cell therapy.

The major obstacles confronting clinical application of bone marrow transplantation lie first in identification of an appropriately histocompatible marrow donor. This is usually accomplished using registries that have enrolled more than 6 million potential donors. The selected donor must undergo a grueling ordeal of induced mobilization stem cell into the blood followed by 4-5 days of leukapheresis to isolate rare lt-HSC. Transplantation of these cells must be followed by careful monitoring and treatment of the recipient to minimize graft versus host reactions caused by passenger lymphocytes.

Elucidation of the molecular basis of the impairment in hematopoietic lineage development has been complicated historically by the low frequency of relevant cell populations, which prevents biochemical analysis of signaling and downstream responses. In fact, this has been a major limiting factor in all studies of hematopoiesis. In addition, the limited availability of long-term hematopoietic stem cells (LT-HSCs) has also been a major obstacle in the treatment of many types of cancer as well as several kinds of immune deficiencies in humans. To the best of the present inventors' knowledge, there are currently no available cell lines that arose spontaneously that resemble lt-HSCs and can differentiate into normal lineages in vitro, or that can reconstitute lethally irradiated mice or sub-lethally irradiated humans, nor have any methods been described to deliberately generate such cell lines. Moreover, there are currently no viable technologies to continuously expand lt-HSCs, such that these cells need to be obtained from a donor every time they are needed.

There is also a dire need for additional modalities to treat hematological malignancies and immune deficiency, and novel cytokines to increase the output of transplanted lt-HSC. In addition, an appropriate platform for target identification and drug discovery does not currently exist. The missing elements are cell lines that represent different developmental stages in hematopoietic lineages. Optimally, such cells should retain the ability to undergo further differentiation in a specific lineage. Such cell lines are essential for identification of gene products, and thus new drugable targets, involved in regulation of cell development, proliferation and survival. In addition, such cell lines are essential for the screening of small molecule and shRNA libraries for loss-of function studies, as well as cDNA libraries for gain of function studies, in search of novel drugs.

Barriers to current drug discovery in this area include: (a) isolation of a sufficient number of cells from a particular developmental stage; (b) propagation of the cells in vitro for a sufficient length of time; and (c) ability to use conditional oncogenes to screen for drugs that could affect leukemic cells, and not normal HSCs or progenitors.

Therefore, there is a great need in the art for a method to generate lt-HSC cell lines that can be expanded extensively, frozen, and used again whenever they are required, in the absence of subsequent harvests from the donor.

SUMMARY OF THE INVENTION

One embodiment of the present invention relates to a method to produce conditionally immortalized adult stem cells. The method includes the steps of: (a) obtaining an expanded population of adult stem cells; (b) transfecting the stem cells with a nucleic acid molecule comprising a protooncogene or biologically active fragment or homologue thereof that promotes cell survival and proliferation, wherein the protooncogene is inducible; (c) transfecting the stem cells with a nucleic acid molecule encoding a protein that inhibits apoptosis of the cell; and (d) expanding the transfected cells in the presence of a combination of stem cell growth factors under conditions whereby the protooncogene is active, to produce conditionally immortalized adult stem cells. In one aspect of this embodiment, the nucleic acid molecule of (b) and/or (c) is contained in an integrating vector. In one aspect, the nucleic acid molecule of (b) and/or (c) is transfected into the cells using a virus or viral vector selected from: retroviral vectors, lentivirus vectors, parvovirus, vaccinia virus, coronavirus, calicivirus, papilloma virus, flavivirus, orthomixovirus, togavirus, picornavirus, adenoviral vectors, modified and attenuated herpesviruses. In one aspect, the nucleic acid molecule of (b) and/or (c) is transfected into the cells using direct electroporation. In one aspect, the nucleic acid molecule or (b) and/or (c) is contained in a vector comprising a nucleic acid sequence encoding a drug-sensitivity protein. In one aspect, the nucleic acid molecule or (b) and/or (c) is contained in a vector comprising nucleic acid sequences encoding recognition substrate sequences for a recombinase flanking the nucleic acid molecule of (b) or (c).

In one aspect, this embodiment includes the additional steps of: (e) removing the conditions of (d) whereby the protooncogene is active; and (f) culturing the cells of (e) in media comprising growth factors that induce differentiation of the cells. This method can further include: (g) adding to the cells of (f), the conditions of (d) whereby the protooncogene is active, to produce conditionally immortalized cells in an intermediate stage of cell differentiation.

Another embodiment of the present invention relates to a method to produce conditionally immortalized adult stem cells, comprising: (a) obtaining an expanded population of adult stem cells; (b) culturing the stem cells in the presence of: (1) a combination of stem cell growth factors; (2) a first Tat-fusion protein, wherein Tat is fused to a protein encoded by a protooncogene or biologically active fragment or homologue thereof that promotes cell survival and proliferation; and (3) a second Tat-fusion protein, wherein Tat is fused to a protein that inhibits apoptosis in the stem cells.

Yet another embodiment of the present invention relates to method to produce conditionally immortalized embryonic stem cells, comprising: (a) obtaining an expanded population of embryonic stem cells; (b) transfecting the stem cells with a nucleic acid molecule comprising a protooncogene or biologically active fragment or homologue thereof that promotes cell survival and proliferation, wherein the protooncogene is inducible; (c) transfecting the stem cells with a nucleic acid molecule encoding a protein that inhibits apoptosis of the cell; and (d) expanding the transfected cells in the presence of a combination of stem cell growth factors under conditions whereby the protooncogene is active, to produce conditionally immortalized embryonic stem cells.

Another embodiment of the present invention relates to method to produce conditionally immortalized stem cells, comprising: (a) obtaining an expanded population of stem cells; (b) culturing the stem cells in the presence of: (1) a combination of stem cell growth factors; (2) a protein encoded by a protooncogene or biologically active fragment or homologue thereof that promotes cell survival and proliferation; and; (3) a protein that inhibits apoptosis in the stem cells. The protein of (2) and (3) are delivered into the stem cells using any suitable delivery system, including, but not limited to, Tat fusion, aptamers technology, or CHARIOT™ technology.

Yet another embodiment of the present invention relates to a method to produce conditionally immortalized stem cells, comprising: (a) obtaining an expanded population of stem cells; (b) delivering into the cells a protein encoded by a protooncogene or biologically active fragment or homologue thereof that promotes cell survival and proliferation, or a nucleic acid molecule encoding the same, wherein the protooncogene is inducible; (c) inhibiting apoptosis in the stem cells by delivering into the cells a protein that inhibits apoptosis of the cell, a nucleic acid molecule encoding the protein that inhibits apoptosis of the cell, or a nucleic acid molecule or protein that inhibits a proapoptotic protein in the cells; and (d) expanding the cells in the presence of a combination of stem cell growth factors under conditions whereby the protooncogene is active, to produce conditionally immortalized adult stem cells.

In any of the embodiments described above, the protooncogene can be selected from, but is not limited to: MYC-ER and ICN-1-ER. In any of the embodiments described above, the protein that inhibits apoptosis can be selected from, but is not limited to a member of the Bcl-2 family that inhibits apoptosis, such as Bcl-2, Bcl-X, Bcl-w, BclXL, Mel-1, Dad-1, or hTERT. When the protooncogene is MYC-ER or ICN-1-ER, the conditions under which the protooncogene is active can include the presence of tamoxifen or an agonist thereof. In one aspect the cells are transfected with or are delivered (as a protein) MYC-ER and Bcl-2; MYC-ER and hTERT; ICN-1-ER and Bcl-2; ICN-1-ER and hTERT; or MYC-ER and ICN-1-ER.

In any of the embodiments described above, the step of expanding can be conducted in a medium including, but not limited to, (1) interleukin-6 (IL-6), IL-3 and stem cell factor (SCF); (2) a serum-free medium comprising stem cell factor (SCF), thrombopoietin (TPO), insulin-like Growth Factor 2 (IGF-2) and fibroblast Growth Factor 1 (FGF-1).

In any of the embodiments described above, the adult stem cells can include, but are not limited to: hematopoietic stem cells, intestinal stem cells, osteoblastic stem cells, mesenchymal stem cells, neural stem cells, epithelial stem cells, cardiac myocyte progenitor stem cells, skin stem cells, skeletal muscle stem cells, and liver stem cells. In one aspect, the mesenchymal stem cells are selected from lung mesenchymal stem cells and bone marrow stromal cells. In one aspect, the epithelial stem cells are selected from the group consisting of lung epithelial stem cells, breast epithelial stem cells, vascular epithelial stem cells and intestinal epithelial stem cells. In one aspect, the skin stem cells are selected from the group consisting of epidermal stem cells and follicular stem cells (hair follicle stem cells). In one aspect, the neural cells are selected from neuronal dopaminergic stem cells and motor-neuronal stem cells. In one aspect, the stem cells are from fresh or cryopreserved cord blood. In one aspect, the stem cells are hematopoietic progenitor cells obtained from the peripheral blood of normal or granulocyte colony-stimulating factor (G-CSF) treated patients.

In any of the embodiments described above, the method can further include genetically modifying the stem cells to correct a genetic defect in the cells, genetically modifying the stem cells to silence the expression of a gene, and/or genetically modifying the stem cells to overexpress a gene.

In any of the embodiments described above, the method can further include storing the cells. In one aspect, the method further includes retrieving the cells from storage and culturing the cells.

Another embodiment of the present invention relates to cells produced by any method described above or elsewhere herein.

Yet another embodiment of the present invention relates to a method to provide adult stem cells, or cells differentiated therefrom, to an individual comprising: (a) providing a source of conditionally immortalized adult stem cells produced by any method described above or elsewhere herein; (b) removing the conditions under which the stem cells of (a) are conditionally immortalized; and (c) administering the stem cells or cells differentiated therefrom to the individual. In one aspect, the cells were previously obtained from the individual in (c). In one aspect, the cells were obtained from a previously frozen stock of said cells. In one aspect, the cells are freshly obtained from the individual and conditionally immortalized by any method described above or elsewhere herein. In one aspect, the individual has cancer. In another aspect, the individual has leukemia. In another aspect, the individual has an immune deficiency disorder. In another aspect, the individual has an anemia disorder. In another aspect, the individual is undergoing reconstructive surgery. In another aspect, the individual is undergoing elective cosmetic surgery. In another aspect, the individual is undergoing transplantation surgery. In one aspect, the individual is in need of stem cells, or cells differentiated therefrom, selected from: hematopoietic stem cells, intestinal stem cells, osteoblastic stem cells, mesenchymal stem cells, neural stem cells, epithelial stem cells, cardiac myocyte progenitor stem cells, skin stem cells, skeletal muscle stem cells, and liver stem cells. In another aspect, the individual is in need of improved immune cell function. In another aspect, the individual has a genetic defect that is corrected by the stem cell.

Yet another embodiment of the present invention relates to a method to identify compounds that regulate lineage commitment and/or cell differentiation and development, comprising: (a) contacting adult stem cells produced by any method described above or elsewhere herein; and (b) detecting at least one genotypic or phenotypic characteristic in the stem cells of (a), as compared to the stem cells in the absence of the compound, wherein detection of a difference in the characteristic in the presence of the compound indicates that the compound affects the characteristic in the stem cell.

Another embodiment of the present invention relates to a method to study lineage commitment and/or cell differentiation and development, comprising evaluating adult stem cells produced by any method described above or elsewhere herein, or cells differentiated therefrom, to detect at least one genotypic or phenotypic characteristic of the cells.

Yet another embodiment of the present invention relates to the use of the cells produced by any method described above or elsewhere herein in a medicament for treating a condition or disease in which transplantation of stem cells is beneficial.

Another embodiment of the present invention relates to a mouse model of acute myeloid leukemia (AML), comprising a mouse produced by a method comprising: (a) lethally irradiating a mouse; (b) transferring conditionally immortalized long-term stem cells produced by any method described above or elsewhere herein and whole bone marrow cells from a $Rag^{-/-}$ mouse into the mouse; and (c) injecting periodic doses of tamoxifen or an agonist thereof into the mouse until the mouse develops clinical signs of AML. In one aspect, the cells are transfected with or are delivered (as a protein) MYC-ER and Bcl-2.

Another embodiment of the invention relates to tumor cells obtained from the mouse model of AML described above.

Yet another embodiment of the invention relates to the use of the mouse model of AML for preclinical testing of drug candidates specific for human proteins; to identify, develop, and/or test a compound for use in the diagnosis of, study of, or treatment of AML; or to identify, develop, and/or test a target for use in the diagnosis of, study of, or treatment of AML.

BRIEF DESCRIPTION OF THE DRAWINGS OF THE INVENTION

FIG. 1 is a graph showing mortality curves following bone marrow transplantation of transduced cells and activation of MYC function with 4OHT, in vivo.

FIG. 2 is a scatter plot showing scatter characteristics and GFP expression levels of HSCs derived from young and aged mice, following in vitro transduction. The dot plots represent the flow cytometric data for the forward (FSC) and side (SSC) scatter characteristics of the HSCs after three days in culture with IL-3, IL-6 and SCF. These two criteria correlate with cell size (FSC) and granularity (SSC).

FIG. 3 is a scatter plot showing the phenotypic comparison of cell lines derived from irradiated recipients reconstituted using BCL-2, MYC-ER and EGFP-transduced hematopoietic stem cells from aged (>60% $ID^-$ repertoire) and young 3-83μδ transgenic mice. Shown is the phenotype of representative clones 3 (young) and 3 (aged) months after initiation of culture.

Figure 8:
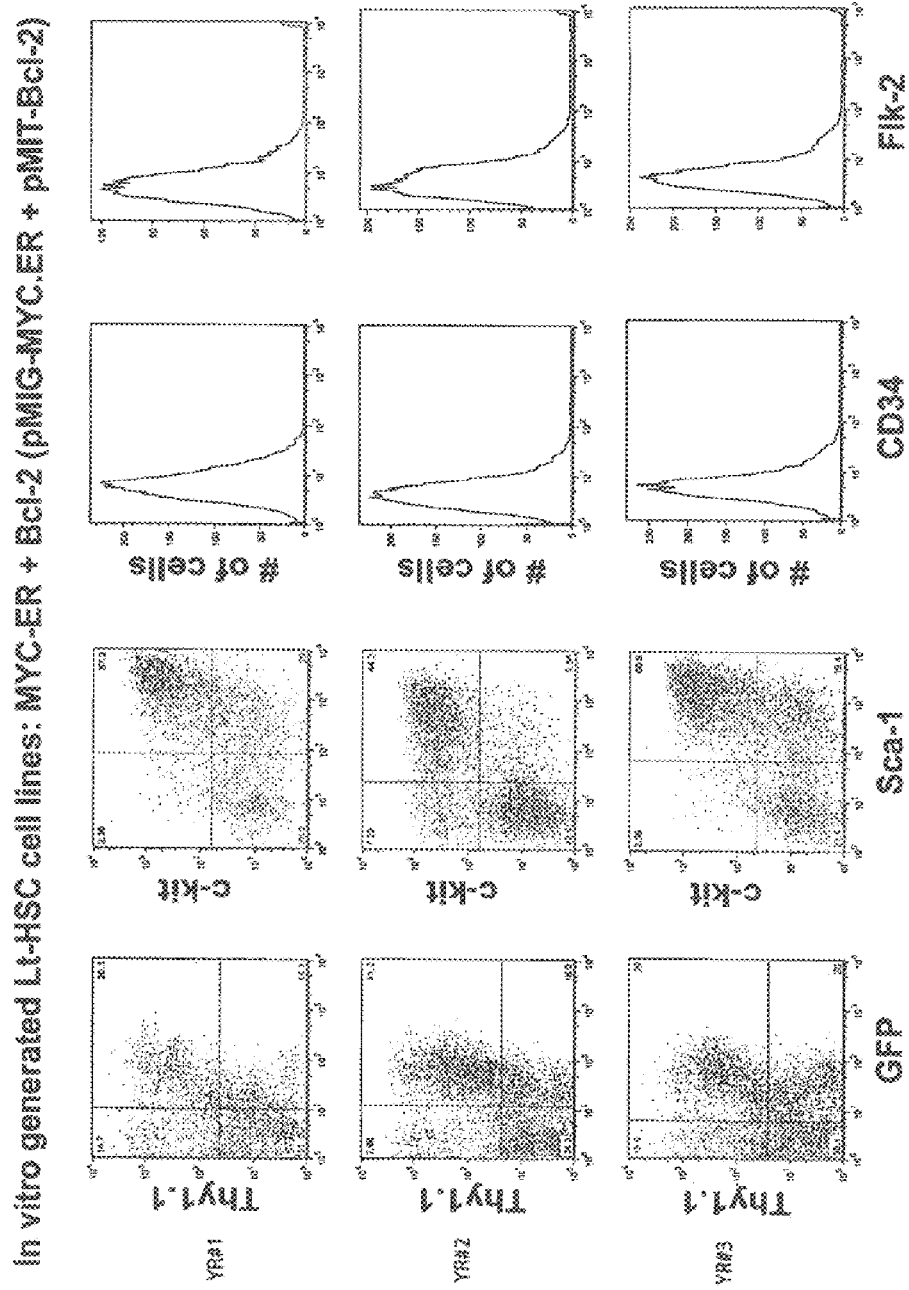

FIG. 8 is a scatter plot and graph showing the phenotypic comparison of cell lines derived from HSCs obtained from young C57/BL6 mice that were retrovirally transduced with BCL-2 and MYC-ER and maintained in continuous in vitro culture for >90 days. The panels represent the results of the flow cytometric analysis for expression of the viral expression markers (GFP and Thy1.1), as well as four markers required to define long-term HSCs in mice, Sca-1, c-kit, CD34 and Flk-2. The four cell lines contained subpopulations that retained the phenotypes of lt-HSCs (Sca-1+, c-kit+, CD34−, flk-2−).

Figure 9:
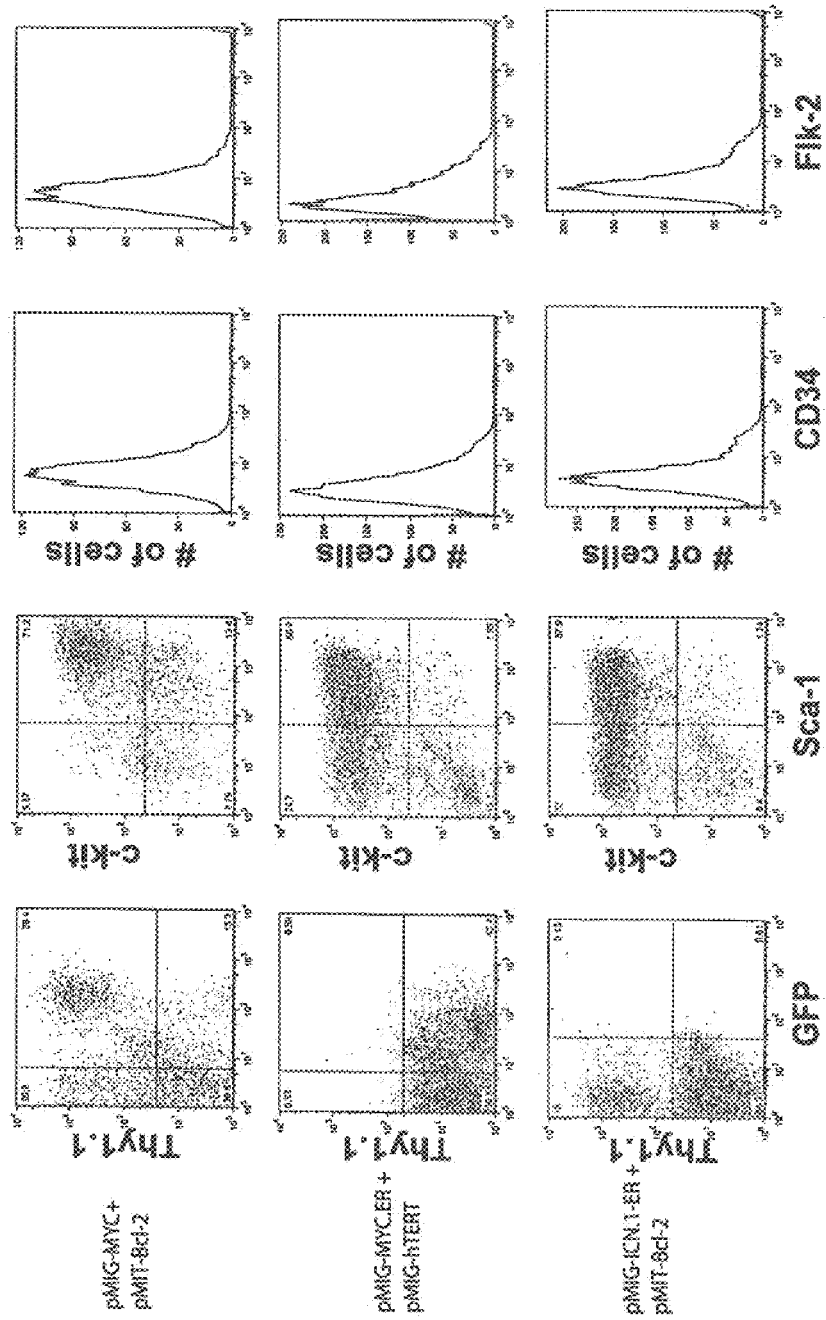

FIG. 9 is a scatter plot and graph showing a phenotypic comparison of cell lines derived from HSCs obtained from young C57/BL6 mice that were retrovirally transduced with different combinations of oncogenes and maintained in, continuous in vitro culture for >90 days (pMIG-MYC and pMIT-Bcl-2 (top panels), pMIG-MYC.ER and pMIG-hTERT (middle panels), or pMIG-ICN.1.ER and pMIT-Bcl-2 (bottom panels)).

Figure 10:
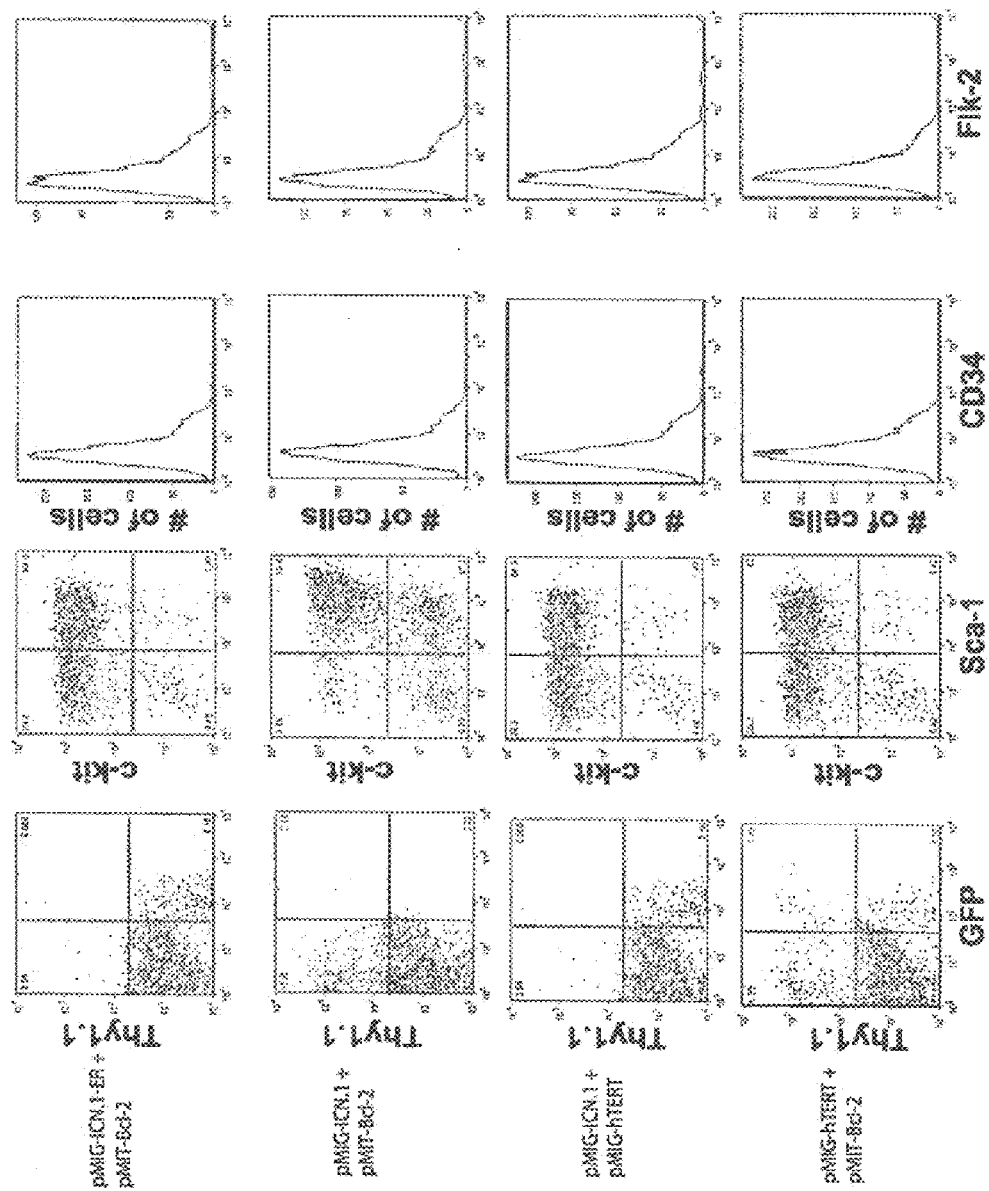

FIG. 10 is a scatter plot and graph showing a phenotypic comparison of cell lines derived from HSCs obtained from young C57/BL6 mice that were retrovirally transduced with different combinations of oncogenes and maintained in continuous in vitro culture for >90 days (pMIG-ICN.1.ER and pMIT-Bcl-2 (top panels), pMIG-ICN.1 and pMIT-Bcl-2 (second row panels), or pMIG-ICN.1 and pMIG-Bcl-2 (third row panels), or pMIG-hTERT and pMIT-Bcl-2 (bottom panels)).

Figure 11:
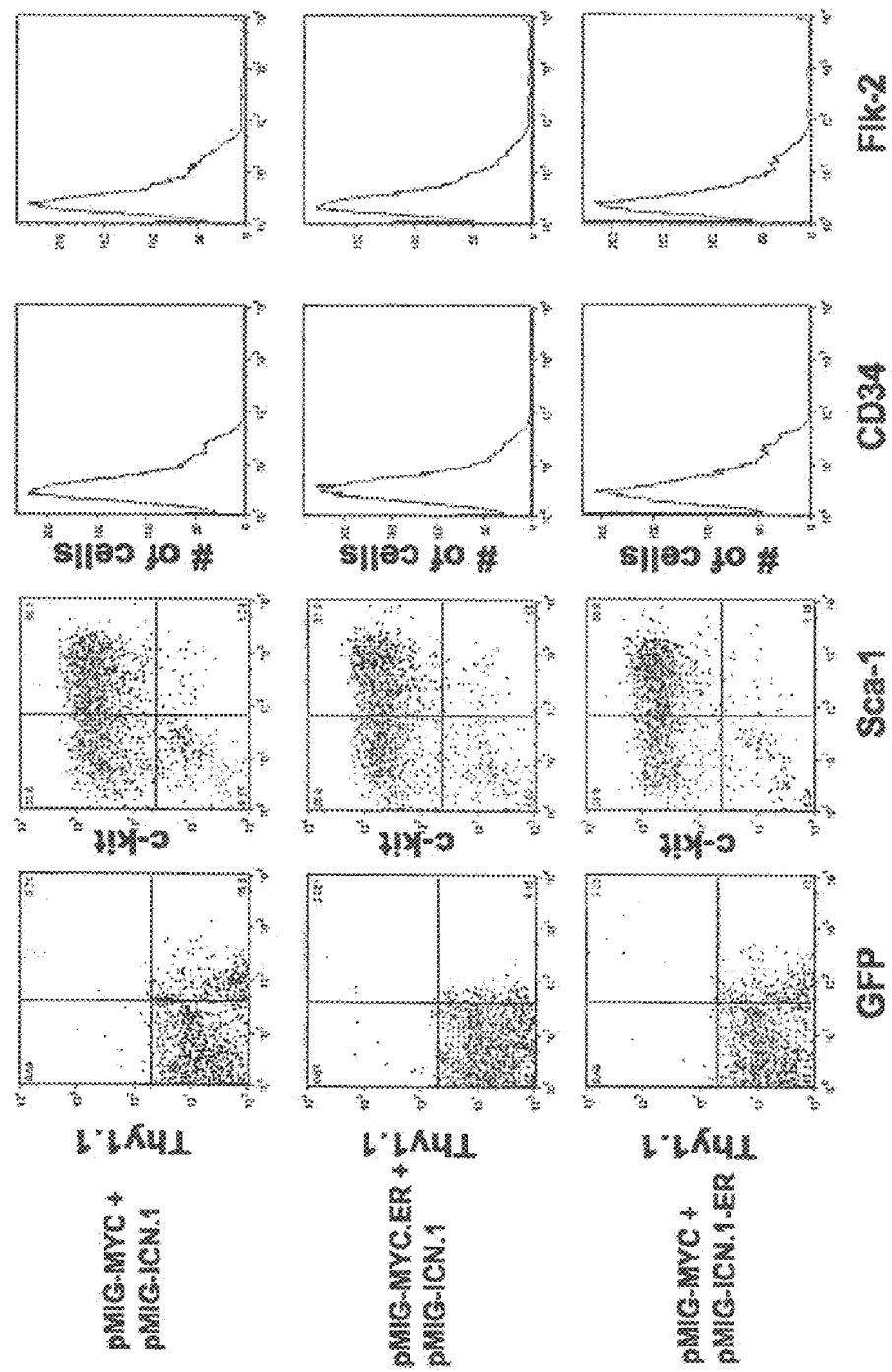

FIG. 11 is a scatter plot and graph showing a phenotypic comparison of cell lines derived from HSCs obtained from young C57/BL6 mice that were retrovirally transduced with different combinations of oncogenes and maintained in continuous in vitro culture for >90 days (pMIG-MYC and pMIG-ICN.1 (top panels), pMIG-MYC.ER and pMIG-ICN.1 (middle panels), or pMIG-ICN.1.ER and pMIG-MYC (bottom panels)).

Figure 12:
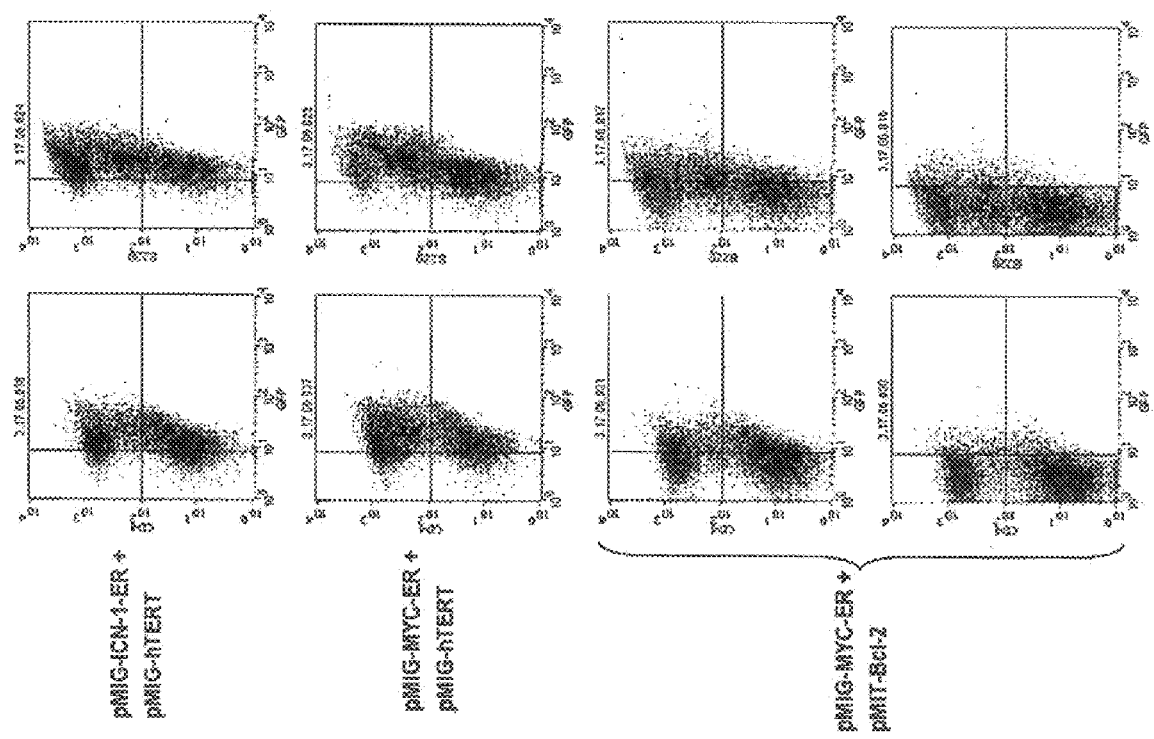

FIG. 12 is a scatter plot showing the in vivo reconstitution of T cell and 13 cell compartments from cell lines derived from HSCs obtained from young C57/BL6 mice that were retrovirally transduced with different combinations of oncogenes and maintained in continuous in vitro culture for >90 days.

Figure 13:
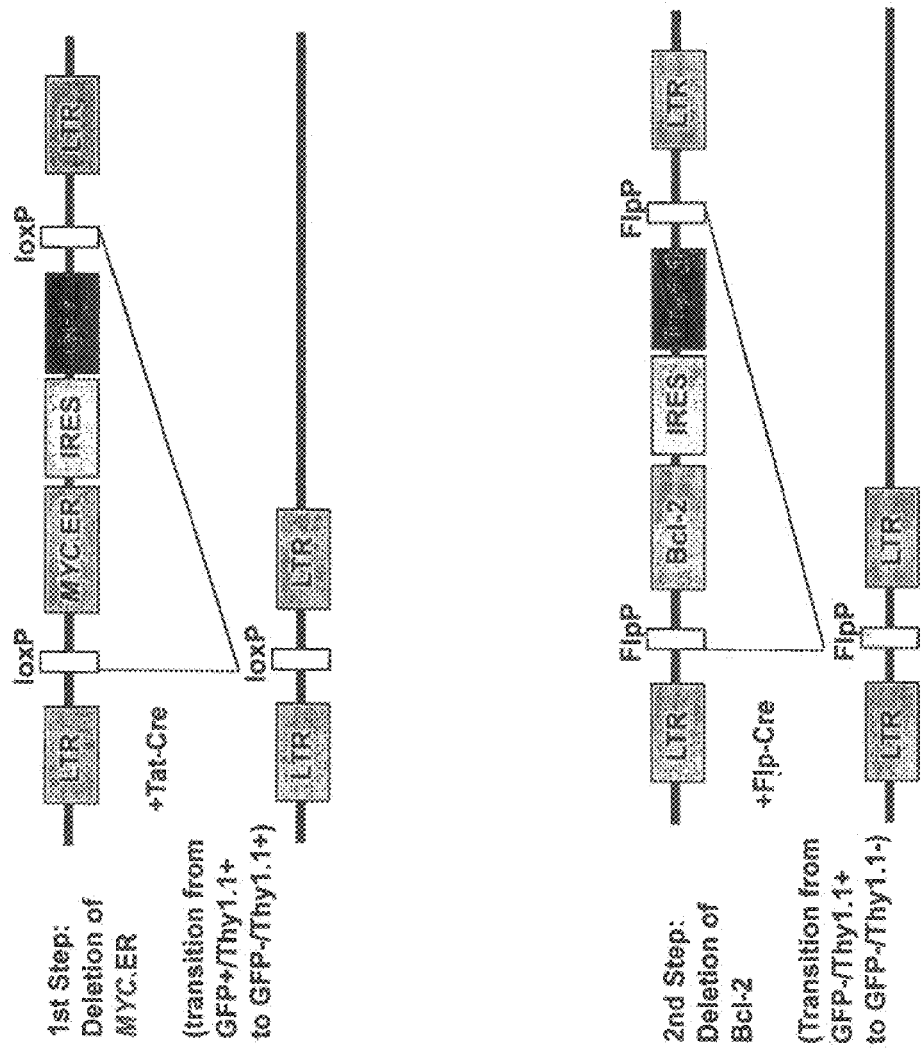

FIG. 13 is a schematic drawing showing the use of recognition substrate sequences (RSS's) for recombinases in order to ensure the excision of recombinant DNA from conditionally immortalized long-term stem cells of the invention prior to transplantation.

Figure 14:
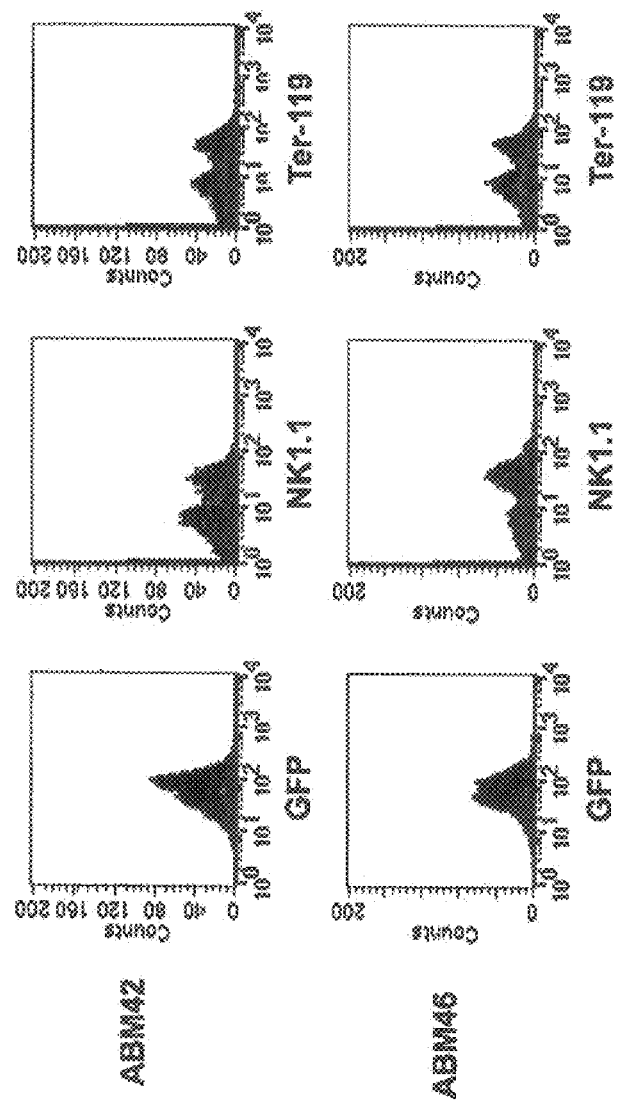

FIG. 14 is a graph showing the detection of cells of the NK and erythroid lineage differentiated from conditionally immortalized long-term stem cells of the invention.

DETAILED DESCRIPTION OF THE INVENTION

The present invention provides a solution to the problem of being able to generate, maintain and manipulate stable cell lines derived from long-term stem cells, and particularly, long-term hematopoietic stem cells (lt-HSCs), that can give rise to all cell lineages that would normally arise from such cells when placed under the appropriate conditions. The present invention generally relates to methods to produce conditionally immortalized, long-term stem cells, to the stem cells produced by such methods, and to methods of using such stem cells. More specifically, using long-term hematopoietic stem cells as an exemplary stem cell population, the present inventors have established a powerful method to produce stem cells that are conditionally immortalized (e.g., reversibly immortalized or immortalized under specified conditions which is reversible when such conditions are removed), such stem cells being capable differentiating into normal cell lineages in vitro and in vivo, and being capable of reconstituting subjects in need of such cells. Indeed, the present invention can eliminate the need for a bone marrow donor, since the invention provides for the ability to harvest stem cells from a patient prior to a procedure (e.g., chemotherapy, radiation, etc.), to expand such cells, and return them to the patient. Moreover, such stem cells can be expanded extensively, stored (e.g., frozen), and then retrieved and expanded again, manipulated, and/or used repeatedly as required or desired. Such stem cells can be manipulated, for example, to correct a genetic defect or provide a benefit to a subject (therapeutic or preventative), or differentiated into a desired cell type. Finally, such cells can be used in a variety of assays for the identification of new targets involved in regulation of cell development, proliferation and survival, and the identification and development of drugs useful in ameliorating or treating diseases and conditions that would benefit from the regulation of cell development, proliferation and/or survival.

The present inventors have developed novel technology that allows the conditional immortalization of long-term stem cells, exemplified herein by long-term hematopoietic stem cells (lt-HSCs). The resulting cell lines can be expanded (propagated) indefinitely and exponentially in vitro and/or cryopreserved (stored), and have the ability to rescue lethally irradiated mice and to reconstitute all blood cell lineages in such animals. Furthermore, the inventors have been able to generate differentiated blood cells in vitro by extinguishing the function of the transforming oncogene. Such cells and the methods of producing them as described herein will allow the generation of transplantable human stem cells that carry no recombinant DNA, and thus pose no long term risk to the recipient. These conditionally immortalized lt-HSC's of the invention can be stabilized in their mature phenotypes and cell lines established in which the mature phenotype is preserved after reactivation of the oncogene. For example, the inventors have been able to develop $CD4^+$ $\alpha\beta^+$ T cells, as well as dendritic cell lines.

Applied in the clinical setting, this technology has the following advantages over bone marrow transplantation:

1. Very few lt-HSC are needed to establish clones;
2. Clones represent a renewable resource that can be stored indefinitely and accessed quickly;
3. The cost of this therapy should be much less than conventional bone marrow transplantation;
4. Use of lt-HSC clones should mitigate the threat of graft-versus-host disease, and associated costs;
5. This technology can, at least in some cases, mitigate the need for a bone marrow donor.

In addition, the present invention provides for the use of the conditionally transformed long-term stem cells, such as the lt-HSC cells, to generate cells representing differentiated lineages (e.g., differentiated hematopoietic lineages, including intermediate stages of development of hematopoietic lineages). For example, in addition to countless therapeutic and preventative applications, these cell lines will allow the identification of novel compounds that can induce differentiation of malignant cells, arrest their growth, or induce apoptosis. These cells will also permit screening for novel cytokines and growth factors that direct the differentiation of stem cells in a particular pathway. Such cell lines simply do not exist and will be essential for drug discovery.

More specifically, in an effort to overcome the limitations in the art with regard to the provision and use of long term populations of adult-derived stem cells (although the invention is not limited to adult-derived stem cells, as discussed below), the present inventors have developed novel methods of producing of conditionally transformed cell lines representing early hematopoietic stem cell progenitors. In a specific, non-limiting example of the technology described and exemplified herein, the strategy involved the transfection (e.g., by retroviral transduction) of bone marrow stem cells from 5-fluorouracil (5-FU)-treated 3-83μδ mice. The inventors utilized the pMSCV bisistronic retroviral vector with inserts encoding Bcl-2 and green fluorescent protein (GFP)

(as a reporter gene), and MYC-ER and GFP (again as a reporter gene). MYC was selected because of its ability to substitute for cytokine-derived survival and proliferative signals in lymphocytes. By restricting the target cell, the inventors hypothesized that stem cell tumors would form. Importantly, MYC-ER function is tamoxifen dependent in this setting, allowing for the termination of MYC function and transformation by withdrawing tamoxifen from the animal or cultures. In cells transduced with MYC-ER, the fusion protein is produced, but is retained in the cytoplasm until exposed to tamoxifen. Bcl-2 was selected because of its ability to inhibit apoptosis of cells that would normally occur as a result of exposure to the MYC signals and more particularly, when MYC is "inactivated" or removed by withdrawal of the tamoxifen from the cells. This novel combination of gene types (i.e., the invention is not limited to these specific genes, as discussed in more detail below) is partly responsible for the successful production of conditionally immortalized stem cells according to the present invention, and can readily be extended to other similar combinations of genes, as discussed in detail below.

Recipients of the transduced stem cells described above produced tumors (in the presence of 4OHT), and tumor cells from the bone marrow, spleen and lymph node were harvested and placed in culture with tamoxifen and a stem cell growth factor cocktail. The present inventors have discovered that, in the absence of an appropriate combination of stem cell growth factors, the stem cells produced by the present method will stop growing and die within a short period of time. Therefore, the use of a stem cell growth factor "cocktail" (i.e., combination of appropriate or suitable growth factors for stem cells) after transfection of the cells with the combination of genes discussed above is a second important aspect of the method of the present invention. This cocktail, while having the general characteristic of promoting and maintaining the growth of the stem cells, is not limited to a particular combination of growth factors, and parameters for selection of such factors are discussed in detail below.

The stem cells generated by the method of the present invention could be expanded in culture and were homogeneously positive for, e.g., Sca1, positive for Endoglin and ckit, and negative for CD34, Flt3, B220, CD19 and mIgM, which are indicative of the phenotype of lt-HSC, which is well-characterized in the art. These cells could be frozen (cryopreserved, or stored), and then easily recovered and cultured after freezing. Importantly, the recovered cells were homogenous in phenotype and exhibited the phenotype of lt-1-ISC (e.g., again, uniformly GFP bright cells were positive for Sca1, Endoglin and ckit, and negative for CD34, Flt3, B220, CD19 and mIgM). This phenotype corresponds perfectly with the published characteristics of long term repopulating pluripotent stem cells (Reya et al., 2003, Nature 423: 409-14) that provide all long-term reconstitution in mice.

The inventors have further developed this method so that it can be performed completely in vitro (i.e., the initial procedure was conducted partly in vivo as described above). The inventors have also demonstrated that other combinations of genes having similar characteristics as those described above also result in the conditional immortalization of lt-HSCs. Furthermore, the cell lines can be differentiated in vitro into hematopoietic lineages by removing the tamoxifen and providing the appropriate growth factors, and will differentiate in vivo into all hematopoietic lineages in recipient animals in which tamoxifen is withheld. In addition, the cells can be differentiated into intermediate levels of development that have a stable phenotype and retain their ability to further differentiate along their committed pathway upon application or removal of the appropriate signal (described herein). Such cells are invaluable for various therapeutic applications. All of these experiments are described in detail below and in the Examples.

The methods and cell lines of the present invention provide a unique opportunity not only to study in detail the molecular, biochemical and cellular events that are associated with the commitment of adult stem cells toward various cell lineages and to study the differentiation and development of stem cells into various cell lineages, but also provide unique therapeutic and drug discovery tools.

For example, the stem cell lines of the present invention provide a unique source of expandable stem cells for use in a variety of transplantation, therapeutic and preventative strategies, including the treatment of cancer, and particularly, cancer that is treated by radiation. In current therapy for leukemia, for example, limited access to bone marrow donors and finite supplies of stem cells from such donors severely limit the options for reconstitution of a patient after radiation therapy. The present invention solves this problem by providing a means to generate a continuously expandable and renewable supply of autologous stem cells or histocompatible stem cells that can be stored and recovered as needed. Such technology could ultimately ablate the need for bone marrow donors altogether. In addition, a variety of immune deficiency disorders and anemia disorders (e.g., aplastic anemia or hemolytic anemia) will also benefit greatly from this technology, since the present invention provides the ability to repopulate hematopoietic cells of an individual as needed by the individual. Furthermore, the aging process is associated with several important changes in the hematopoietic compartment, including the increasing inability to mount a productive immune response, among others. Hematopoietic stem cells from aged mice have been shown to contain a higher level of mRNAs for DNA-repair problems. This may ultimately affect their ability to self-renew, undergo differentiation, undergo proliferation, and survive in response to bone marrow cytokines. Therefore, an aging individual can also benefit from the present invention in that a continuous supply of healthy hematopoietic cells can be provided to correct or ameliorate such deficiencies.

The technology of the present invention is not limited to bone marrow stem cells, but can be applied to virtually any type of stem cell, and can be extended beyond adult-derived cells to embryonic stem cells.

In one example, another application of the present invention relates to the generation of continuously expandable and renewable hair follicle stem cells. The development of conditionally immortalized stem cells from this lineage can be use in the context of reconstructive surgery for burn victims, for any individual that undergoes chemotherapy and/or radiation therapy resulting in the irreversible loss of hair growth, as well as patients following any surgical procedure affecting the skull. Furthermore, such cells could be used for elective procedures that involve the induction of hair growth in individuals affected by hereditary pattern baldness. Similarly, application of the present invention to stem cells of the skin will be invaluable for use in wound healing and treatment of burn victims, as well as plastic reconstructive surgery for trauma and other patients, as well as elective surgeries, including, but not limited to, cosmetic surgery. Such cells can be additionally genetically manipulated to correct inborn or acquired genetic defects in young and aged individuals. One of skill in the art will understand based on this disclosure that benefits can be derived from the use of the present invention on various other stem cell populations, including, but not limited to, stem cells derived from lung, breast, and intestinal epithelium and stem cells derived from neural and cardiac tissue, to name just a few. Other stem cell types are referenced elsewhere herein.

In addition, the present invention provides the unique opportunity for an individual to have access to expandable supplies of autologous stem cells and cells differentiated therefrom as needed throughout the life of the individual. For example, as the body ages, it is known that immune function and immune memory deteriorates. However, using the technology provided by the present invention, it will be possible to repopulate an individual with new, autologous stem cells that are capable of differentiation into all of the cells of the hematopoietic lineage, thus providing the aged individual with a "young" immune system. In addition, stem cells generated by the present method can be stored and used as part of therapeutic protocols during the lifetime of the individual, should they be needed (e.g., in the event the individual develops a cancer or immune deficiency disease or has another need for newly generated, autologous cells of virtually any type).

The present invention also provides unique opportunities for gene therapy. Specifically, genetic defects can now be corrected or beneficial gene modifications can be introduced into somatic cells by manipulating autologous stem cells obtained from an individual that have been conditionally immortalized and expanded using the method of the present invention. The stem cells can then be reintroduced into the individual from which they were obtained.

The stem cells produced by the method of the invention can also be used in a variety of drug discovery assays. Since one can now produce virtually unlimited supplies of homogeneous stem cells that can readily be stored, recovered, expanded and manipulated, such stem cells can be used as stem cells or differentiated into various cell lineages and used in assays to test various compounds for effects on cell differentiation, gene expression, and cell processes. The cells can be manipulated prior to contact with the compounds, such as by genetic manipulation. Stem cells from individuals with genetic defects can be evaluated in such assays in order to identify therapeutic compounds (e.g., cancer therapeutics) and evaluate gene replacement therapies. Indeed, the technology of the present invention provides an opportunity to target the cells of a specific individual to identify drug candidates and therapeutic candidates and strategies that are "tailored" to the cells of an individual. An example of such an assay is described in detail below.

With regard to research and discovery in the area of lineage commitment and cell differentiation and development, prior to the present invention, such studies were severely hampered by the lack of access to and the inability to generate sufficient numbers of the desired cell population to perform desired experiments. For example, in order to identify or screen for intermediates in the differentiation of a particular progenitor cell line, a sufficient number of cells must be obtained to provide meaningful and reproducible results. The progenitor cell line should also retain the ability to further differentiate in the lineage to which it has already committed, hence making these novel tools that do not currently exits, nor are there other descriptions of technology needed to generate those cells. Using technologies available at the time of the invention, this was not possible. The present invention solves the problem by providing expandable and essentially unlimited supplies of homogeneous stem cells that can be used in a variety of experiments. This technology will greatly enhance research capabilities in the area of cell differentiation and discovery.

As discussed above, the method for conditionally immortalizing lt-HSCs of the present invention can be adapted for additional stem cells derived from other tissues. For example, by adapting the gene delivery and growth factors, if needed, the present invention can be applied to a variety of different stem cells as described below. Such cells can also be expanded in vitro, and proceed to differentiate upon inactivation of the oncogenes, as described herein for hematopoietic stem cells. These cells can then be used for therapeutic applications that include tissue repair and tissue regeneration/engineering. Accordingly, the MYC-ER and Bcl-2 combination of genes, or any of the other combinations described herein, can be transfected by any method described herein or deemed suitable by one of skill in the art given this disclosure (including by a variety of viral-mediated methods), into cells including, but not limited to, mesenchymal stem cells (including, but not limited to, lung mesenchymal stem cells, bone marrow stromal cells), neural stem cells (including, but not limited to, neuronal dopaminergic stem cells and motor-neuronal stem cells), epithelial stem cells (including, but not limited to, lung epithelial stem cells, breast epithelial stem cells, and intestinal epithelial stem cells), cardiac myocyte progenitor stem cells, skin stem cells (including, but not limited to, epidermal stem cells and follicular stem cells), skeletal muscle stem cells, endothelial stem cells (e.g., lung endothelial stem cells), and liver stem cells, to generate conditionally immortalized cell lines that can be expanded in vitro and proceed to differentiate upon inactivation of the oncogenes. In addition to the therapeutic potential of such cell lines, these lines can be further modified in vitro (or ex vivo) in order to correct inborn genetic defects, and used for studying the molecular basis of early lineage commitment and differentiation. While these cells may be a novel source of potentially relevant therapeutic targets, these cell lines will also be useful for the screening of small molecules that either prevent or induce differentiation, and for the identification of novel compounds and molecular targets for various therapies, including, but not limited to, cancer therapy and immune deficiency therapy.

General Definitions

In accordance with the present invention, reference to an isolated nucleic acid molecule herein is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene. An isolated nucleic acid molecule that includes a gene is not a fragment of a chromosome that includes such gene, but rather includes the coding region and regulatory regions associated with the gene, but no additional genes that are naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA, siRNA, shRNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein or domain of a protein.

Preferably, an isolated nucleic acid molecule of the present invention is produced using recombinant DNA technology (e.g., polymerase chain reaction (PCR) amplification, cloning) or chemical synthesis. Isolated nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications provide the desired effect (e.g., provision of an inducible protooncogene, as described herein).

A nucleic acid molecule homologue can be produced using a number of methods known to those skilled in the art (see, for example, Sambrook et al., Molecular Cloning: A Laboratory Manual, Cold Spring Harbor Labs Press (1989)). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid and/or by hybridization with a wild-type gene.

The minimum size of a nucleic acid molecule or polynucleotide of the present invention is a size sufficient to encode a protein useful in the present invention, such as a protein encoded by a protooncogene or functional portion thereof (i.e., a portion that has the biological activity of the full-length protein and that is sufficient for use in the method of the invention), or an anti-apoptotic protein or a functional portion thereof (i.e., a portion that has the biological activity of the full-length protein and that is sufficient for use in the method of the invention). Other nucleic acid molecules that may be useful in the present invention can include nucleic acid molecules of a minimum size sufficient to form a probe or oligonucleotide primer that is capable of forming a stable hybrid with the complementary sequence of a nucleic acid molecule encoding the natural protein (e.g., under moderate, high or very high stringency conditions), which is typically at least 5 nucleotides in length, and preferably ranges from about 5 to about 50 or about 500 nucleotides or greater, including any length in between, in whole number increments (i.e., 5, 6, 7, 8, 9, 10, . . . 33, 34, . . . 256, 257, . . . 500). There is no limit, other than a practical limit, on the maximal size of a nucleic acid molecule of the present invention, in that the nucleic acid molecule can include a sequence or sequences sufficient to be useful in any of the embodiments of the invention described herein.

As used herein, stringent hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety.

More particularly, moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M $Na^+$) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6×SSC (0.9 M $Na^+$) at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C.' below the calculated $T_m$ of a particular hybrid, and wash conditions typically include a combination of salt and temperature conditions that are approximately 12-20° C. below the calculated $T_m$ of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×-0.5×SSC, followed by at least one wash at about 68° C. in about 0.1×-0.5×SSC).

In one embodiment of the present invention, any amino acid sequence described herein, including truncated forms (fragments or portions) and homologues of such sequences, can be produced with from at least one, and up to about 20, additional heterologous amino acids flanking each of the C- and/or N-terminal end of the given amino acid sequence. The resulting protein or polypeptide can be referred to as "consisting essentially of" a given amino acid sequence. According to the present invention, the heterologous amino acids are a sequence of amino acids that are not naturally found (i.e., not found in nature, in vivo) flanking the given amino acid sequence or which would not be encoded by the nucleotides that flank the naturally occurring nucleic acid sequence encoding the given amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a given amino acid sequence that can be flanked by from at least one, and up to as many as about 60, additional heterologous nucleotides at each of the 5' and/or the 3' end of the nucleic acid sequence encoding the given amino acid sequence. The heterologous nucleotides are not naturally found (i.e., not found in nature, in vivo) flanking the nucleic acid sequence encoding the given amino acid sequence as it occurs in the natural gene.

According to the present invention, a recombinant vector (also referred to generally as a recombinant nucleic acid molecule, particularly when it contains a nucleic acid sequence of interest according to the invention) is an engineered (i.e., artificially produced) nucleic acid molecule that is used as a tool for manipulating a nucleic acid sequence of choice and for introducing such a nucleic acid sequence into a host cell. The recombinant vector is therefore suitable for use in cloning, sequencing, and/or otherwise manipulating the nucleic acid sequence of choice, such as by expressing and/or delivering the nucleic acid sequence of choice into a host cell. Such a vector typically contains heterologous nucleic acid sequences, i.e., nucleic acid sequences that are not naturally or usually found adjacent to a nucleic acid sequence to be cloned or delivered, although the vector can also contain regulatory nucleic acid sequences (e.g., promoters, untranslated regions) which are naturally found adjacent to nucleic acid molecules of the present invention, or which are useful for expression of the nucleic acid molecules of the present invention (discussed in detail below). A vector can be either RNA or DNA, either prokaryotic or eukaryotic, and typically is a plasmid or a viral vector. The vector can be maintained as an extrachromosomal element (e.g., a plasmid) or it can be integrated into the chromosome of a host cell. The entire vector can remain in place within a host cell, or under certain conditions, the plasmid DNA can be deleted, leaving behind the nucleic acid molecule of the present invention. Under other conditions, the vector is designed to be excised (removed) from the genome of the host cell at a selected time (described in more detail below). The integrated nucleic acid molecule can be under chromosomal promoter control, under native or plasmid promoter control, or under a combination of several promoter controls. Single or multiple copies of the nucleic acid molecule can be integrated into the chromosome. A recombinant vector of the present invention can contain at least one selectable marker.

According to the present invention, the phrase "operatively linked" refers to linking a nucleic acid molecule to an expression control sequence (e.g., a transcription control sequence and/or a translation control sequence) in a manner such that the molecule can be expressed when transfected (i.e., transformed, transduced, transfected, conjugated or conduced) into a host cell. Transcription control sequences are sequences that control the initiation, elongation, or termination of transcription. Particularly important transcription control sequences are those that control transcription initiation, such as promoter, enhancer, operator and repressor sequences. Suitable transcription control sequences include any transcription control sequence that can function in a host cell or organism into which the recombinant nucleic acid molecule is to be introduced.

According to the present invention, the term "transfection" is used to refer to any method by which an exogenous nucleic acid molecule (i.e., a recombinant nucleic acid molecule) can be inserted into a cell. The term "transduction" is a specific type of transfection in which genetic material is transferred from one source to another, such as by a virus (e.g., a retrovirus) or a transducing bacteriophage. The term "transformation" can be used interchangeably with the term "transfection" when such term is used to refer to the introduction of nucleic acid molecules into microbial cells, such as bacteria and yeast. In microbial systems, the term "transformation" is used to describe an inherited change due to the acquisition of exogenous nucleic acids by the microorganism and is essentially synonymous with the term "transfection." However, in animal cells, transformation has acquired a second meaning that can refer to changes in the growth properties of cells in culture after they become cancerous, for example. Therefore, to avoid confusion, the term "transfection" is preferably used herein with regard to the introduction of exogenous nucleic acids into animal cells. Therefore, the term "transfection" will be used herein to generally encompass transfection or transduction of animal cells, and transformation or transduction of microbial cells, to the extent that the terms pertain to the introduction of exogenous nucleic acids into a cell. Transfection techniques include, but are not limited to, transformation, transduction, particle bombardment, diffusion, active transport, bath sonication, electroporation, microinjection, lipofection, adsorption, infection and protoplast fusion.

As used herein, reference to an isolated protein or polypeptide in the present invention includes full-length proteins, fusion proteins, chimeric proteins, or any fragment (truncated form, portion) or homologue of such a protein. More specifically, an isolated protein according to the present invention, is a protein (including a polypeptide or peptide) that has been removed from its natural milieu (i.e., that has been subject to human manipulation), and can include, but is not limited to, purified proteins, partially purified proteins, recombinantly produced proteins, membrane bound proteins, proteins complexed with lipids, soluble proteins, synthetically produced proteins, and isolated proteins associated with other proteins. As such, "isolated" does not reflect the extent to which the protein has been purified. Preferably, an isolated protein of the present invention is produced recombinantly. In addition, and again by way of example with respect to the naming of a particular protein (Bcl-2), a "human Bcl-2 protein" or a protein "derived from" a human Bcl-2 protein refers to a Bcl-2 protein (including a homologue or portion of a naturally occurring Bcl-2 protein) from a human (*Homo sapiens*) or to a Bcl-2 protein that has been otherwise produced from the knowledge of the structure (e.g., sequence) and perhaps the function of a naturally occurring Bcl-2 protein from *Homo sapiens*. In other words, a human Bcl-2 protein includes any Bcl-2 protein that has substantially similar structure and function of a naturally occurring Bcl-2 protein from *Homo sapiens* or that is a biologically active (i.e., has biological activity) homologue of a naturally occurring Bcl-2 protein from *Homo sapiens* as described in detail herein. As such, a human Bcl-2 protein can include purified, partially purified, recombinant, mutated/modified and synthetic proteins. According to the present invention, the terms "modification" and "mutation" can be used interchangeably, particularly with regard to the modifications/mutations to the amino acid sequence of a protein (or nucleic acid sequences) described herein.

As used herein, the term "homologue" is used to refer to a protein or peptide which differs from a naturally occurring protein or peptide (i.e., the "prototype" or "wild-type" protein) by modifications, including minor modifications, to the naturally occurring protein or peptide, but which maintains the basic protein and side chain structure of the naturally occurring form: Such changes include, but are not limited to: changes in one or a few (i.e., 1, 2, 3, 4, 5, 6, 7, 8, 9 or 10) amino acid side chains; changes one or a few amino acids, including deletions (e.g., a protein or truncated form of the protein or peptide), insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have either enhanced, decreased, or substantially similar properties as compared to the naturally occurring protein or peptide. A homologue can include an agonist of a protein or an antagonist of a protein.

Homologues can be the result of natural allelic variation or natural mutation. A naturally occurring allelic variant of a nucleic acid encoding a protein is a gene that occurs at essentially the same locus (or loci) in the genome as the gene which encodes such protein, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

In one embodiment, a homologue of a given protein comprises, consists essentially of, or consists of, an amino acid sequence that is at least about 45%, or at least about 50%, or at least about 55%, or at least about 60%, or at least about 65%, or at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 45% and 99%, in whole integer increments), to the amino acid sequence of the reference protein. In one embodiment, the homologue comprises, consists essentially of, or consists of, an amino acid sequence that is less than 100% identical, less than about 99% identical, less than about 98% identical, less than about 97% identical, less than about 96% identical, less than about 95% identical, and so on, in increments of 1%, to less than about 70% identical to the naturally occurring amino acid sequence of the reference protein.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174: 247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
Reward for match=1
Penalty for mismatch=−2
Open gap (5) and extension gap (2) penalties
gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

According to the present invention, an isolated protein, including a biologically active homologue or fragment thereof, has at least one characteristic of biological activity of activity the wild-type, or natural (native) protein. In general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions). Modifications, activities or interactions which result in a decrease in protein expression or a decrease in the activity of the protein, can be referred to as inactivation (complete or partial), down-regulation, reduced action, or decreased action or activity of a protein. Similarly, modifications, activities or interactions that result in an increase in protein expression or an increase in the activity of the protein, can be referred to as amplification, overproduction, activation, enhancement, up-regulation or increased action of a protein.

Method of Conditional Immortalization of the Invention

One embodiment of the present invention relates to a method to produce conditionally immortalized, adult stem cells, and preferably long-term stem cells. The method generally includes the following steps: (a) obtaining an expanded population of adult stem cells; (b) transfecting (transducing) the stem cells with a vector comprising a protooncogene that promotes cell survival and proliferation, wherein the protooncogene is regulatable (inducible, controllable), (c) transfecting (transducing) the stem cells with a vector encoding a protein that inhibits apoptosis of the cell; and (d) expanding the transfected cells in the presence of a combination of stem cell growth factors under conditions whereby the protooncogene is active. In one embodiment, the vector is an integrating vector. Cells produced by this method can be cultured, expanded, stored, recovered, used in therapeutic methods, used in research and discovery methods, genetically manipulated, induced to differentiate by removing the conditions whereby the protooncogene is active, and/or used in any other method described herein or apparent to one of skill in the art given this disclosure. Steps (b) and (c) can be performed in any order.

According to the present invention, the phrase "conditionally immortalized" refers to cells that are immortalized (e.g., capable of indefinite growth without differentiation in a cytokine dependent fashion, while maintaining their ability and potential to differentiate into a number of different lineages under the appropriate conditions) in a reversible manner, such that the cells are immortalized under a specific set of conditions, and when the conditions are removed or changed (or other conditions added), the cells are no longer immortalized and may differentiate into other cell types. The phrase "conditionally immortalized" can be used interchangeably with the phrase "reversibly immortalized". For example, referring to the method of the present invention, the presence of the regulatable protooncogene that promotes cell survival and proliferation causes the cells to retain an immortalized phenotype when the stem cell is placed under conditions that allow the protooncogene to be activated (e.g., tamoxifen or an agonist thereof in the case of MYC-ER). In other words, the cells grow and expand indefinitely in culture, and are maintained in an undifferentiated state under these specific conditions. When these conditions are removed (e.g., the tamoxifen is removed with respect to MYC-ER), the stem cells are no longer immortalized and can differentiate into various cell lineages given the appropriate environment (e.g., the appropriate combination of growth factors).

Reference to "stem cells", as used herein, refers to the term as it is generally understood in the art. For example, stem cells, regardless of their source, are cells that are capable of dividing and renewing themselves for long periods, are unspecialized (undifferentiated), and can give rise to (differentiate into) specialized cell types (i.e., they are progenitor or precursor cells for a variety of different, specialized cell types). "Long-term", when used in connection with stem cells, refers to the ability of stem cells to renew themselves by dividing into the same non-specialized cell type over long periods (e.g., many months, such as at least 3 months, to years) depending on the specific type of stem cell. As discussed herein, phenotypic characteristics of various long-term stem cells from different animal species, such as long-term hematopoietic stem cells (lt-HSC) are known in the art. For example, murine lt-HSC can be identified by the presence of the following cell surface marker phenotype: c-kit+, Sca-1+, CD34−, flk2− (see Examples). Adult stem cells include stem cells that can be obtained from any non-embryonic tissue or source, and typically generate the cell types of the tissue in which they reside. The term "adult stem cell" may be used interchangeably with the term "somatic stem cell". Embryonic stem cells are stem cells obtained from any embryonic tissue or source.

In one embodiment of the invention, the stem cells used in the present invention can include any adult stem cells obtained from any source. In another embodiment of the invention, stem cells can include embryonic stem cells. Stem cells useful in the present invention include, but are not limited to, hematopoietic stem cells, mesenchymal stem cells (including, but not limited to, lung mesenchymal stem cells, bone marrow stromal cells), neural stem cells, epithelial stem cells (including, but not limited to, lung epithelial stem cells, breast epithelial stem cells, vascular epithelial stem cells, and intestinal epithelial stem cells), intestinal stem cells, cardiac myocyte progenitor stem cells, skin stem cells (including, but not limited to, epidermal stem cells and follicular stem cells (hair follicle stem cells)), skeletal muscle stem cells, osteoblastic precursor stem cells, and liver stem cells.

Hematopoietic stem cells give rise to all of the types of blood cells, including but not limited to, red blood cells (erythrocytes), B lymphocytes, T lymphocytes, natural killer cells, neutrophils, basophils, eosinophils, monocytes, macrophages, and platelets.

Mesenchymal stem cells (including bone marrow stromal cells) give rise to a variety of cell types, including, but not limited to bone cells (osteocytes), cartilage cells (chondrocytes), fat cells (adipocytes), lung cells, and other kinds of connective tissue cells such as those in tendons.

Neural stem cells in the brain give rise to its three major cell types: nerve cells (neurons) and two categories of non-neuronal cells, astrocytes and oligodendrocytes.

Epithelial stem cells in the lining of various tissues give rise to several cell types that form the epithelium in tissues.

Skin stem cells occur in the basal layer of the epidermis and at the base of hair follicles. The epidermal stem cells give rise to keratinocytes, which migrate to the surface of the skin and form a protective layer, and the follicular stem cells can give rise to both the hair follicle and to the epidermis. Other sources of adult stem cells will be known to those of skill in the art.

Embryonic stem cells can give rise to all tissues and cells of the body.

Methods for obtaining such stem cells and providing initial culture conditions, such as a liquid culture or semi-solid culture medium, are known in the art. The cells are initially expanded in vivo or in vitro, by contacting the source of the stem cells with a suitable reagent that expands or enriches such cells in the tissue source or in culture. For example, in the case of hematopoietic stem cells, the donor individual can be treated with an agent that enriches for hematopoietic stem cells and encourages such cells to proliferate without differentiation, such as 5-fluorouracil. Other suitable agents for expansion of a desired stem cell type will be known to those of skill in the art. Alternatively, and preferably, adult stem cells are isolated from a tissue source and then expanded or enriched in vitro by exposure to a suitable agent. For example, with regard to hematopoietic stem cells, a method for producing an expanded culture of adult hematopoietic progenitors is described in Van Parijs et al., (1999; Immunity, 11, 763-70). Cells are obtained from an individual by any suitable method for obtaining a cell sample from an animal, including, but not limited, to, collection of bone marrow collection of a bodily fluid (e.g., blood), collection of umbilical cord blood, tissue punch, and tissue dissection, including particularly, but not limited to, any biopsies of skin, intestine, cornea, spinal cord, brain tissue, scalp, stomach, breast, lung (e.g., including lavage and bronchioschopy), fine needle aspirates of the bone marrow, amniotic fluid, placenta and yolk sac.

In one embodiment, cells useful in the invention can also be obtained from fresh, or cryopreserved (stored) cord blood, hematopoietic progenitor populations that can be derived from the directed differentiation of embryonic stem (ES) cells in vitro, hematopoietic stem cells (HSCs) obtained from the peripheral blood of normal or granulocyte colony-stimulating factor (G-CSF)-treated patients who have been induced to mobilize their lt-HSCs to the peripheral circulation.

Once an expanded population of stem cells is obtained (made available, provided, or produced), the cells are transfected, either sequentially (in any order) or simultaneously, with: (1) a vector comprising a protooncogene that promotes cell survival and proliferation, wherein the protooncogene is regulatable (inducible, controllable), and (2) a vector encoding a protein that inhibits apoptosis of the cell. Preferably, the vector is an integrating vector, defined herein as any vector that has the ability to integrate into the genome of a cell (e.g., a retroviral vector). Various vectors and methods of transfection are described in detail below. The protooncogene is regulatable (inducible or controllable), so that the protooncogene can be activated and deactivated (i.e., turned on or turned off) as desired to either maintain the stem cell in an immortalized state or to allow it to differentiate into a desired cell type. Protooncogenes can be selected, or designed, to be regulated by any suitable method, including in response to any condition, such as the presence or absence of a compound or agent, temperature, or any other suitable condition. By way of example, the protooncogenes MYC-ER (the estrogen receptor (ER)-regulated MYC) and ICN-1-ER (the ER-regulated intracellular portion of Notch-1) described herein are both inducible in the presence of tamoxifen. It is noted that such genes can also be engineered to be responsive to other dimerizing drugs, such as FK1012, altered forms of Rapamycin, or could be expressed from vectors that contain a tetracycline responsive element. The latter scenario regulates expression of the protein, not the function of a polypeptide present in the cell. Other similar modifications of this platform technology will be apparent to those of skill in the art.

The protooncogene useful in the method of the present invention is any protooncogene that promotes cell survival and proliferation. Preferred protooncogenes to use in the method of the invention include, but are not limited to MYC, ICN-1, hTERT (reverse transcriptase component of the human telomerase), NMYC, S-MYC, L-MYC, Akt, (myrystylated). In addition, other suitable genes to use or methods of the invention or ways to modify genes to achieve the desired result include, but are not limited to use of downstream signaling effectors such as pyruvate dehydrogenase kinase 1 (PDK-1); mammalian target of Rapamycin (mTOR); loss of phosphatase and tensin homologue (PTEN) by shRNA; Bcl-3, Cyclin D1, Cyclin D3, Bcl-10, Bcl-6, BCR-ABL (breakpoint cluster region fusion with ABL) and its various mutant forms, constitutively active forms of Stat5 and Stat3, AML1-ETO (fusion of acute myelogenous leukemia 1 and runt-related transcription factor 1), MLL-ENL (mixed lineage leukemia and eleven nineteen leukemia), Hox genes, activated forms of the interleukin-3 (IL-3) receptor β chain, and other cytokine receptor chains (epidermal growth factor receptor (EGFR), c-kit, platelet-derived growth factor receptor (PDGFR), etc.), as well as wnt (all mammalian forms), β-catenin, sonic hedgehog (shh-1 and all mammalian forms), bmi-1 and c-jun (all mammalian forms). Also, the present invention includes inducing the loss (or inhibition) of cyclin kinase inhibitors by shRNA, including, but not limited to, p16, p19, p21 and p27. In one embodiment, the present invention includes the use of regulatable homologues of any or such protooncogenes (e.g., MYC-ER or ICN-1-ER) or other genes. The Examples describe the use of both MYC-ER or ICN-1-ER to successfully produce conditionally immortalized lt-HSC using the method of present invention.

The nucleic acid sequence encoding human MYC is represented herein as SEQ ID NO:1, which encodes an amino acid sequence represented herein as SEQ ID NO:2. The nucleic acid sequence encoding hTERT is represented herein as SEQ ID NO:3, which encodes an amino acid sequence represented herein as SEQ ID NO:4. The nucleic acid sequence encoding human ICN-1 is represented herein as SEQ ID NO:11, which encodes an amino acid sequence represented herein as SEQ ID NO:12. ICN-1 a portion of Notch-1, and specifically, amino acids 1757-2555 from Notch-1 (see Aster et al., *Mol Cell Biol.* 2000 Oct.; 20(20):7505-15, incorporated herein by reference in its entirety). The nucleotide and amino acid sequence for MYC-ER are known in the art and the MYC-ER protein is described in Soloman et al., *Oncogene.* 1995 Nov. 2; 11(9):1893-7, incorporated herein by reference in its entirety. ICN-1-ER was created by the present inventors and the nucleic acid sequence encoding this protein is represented herein as SEQ ID NO:13, which encodes an amino acid sequence represented by SEQ ID NO:14.

Similarly, a preferred anti-apoptosis gene is Bcl-2, although other genes that encode proteins that inhibit apoptosis and particularly, maintain cell survival when the protooncogene is inactivated in the stem cell, are included in the present invention. The nucleic acid sequence encoding Bcl-2 alpha is represented herein as SEQ ID NO:5, which encodes an amino acid sequence of SEQ ID NO:6. Bcl-2 beta is represented herein as SEQ ID NO:7, which encodes an amino acid sequence of SEQ ID NO:8. An "anti-apoptosis" gene is defined herein as any gene that encodes a protein that can inhibit (reduce, prevent, decrease) a process associated with apoptosis in a cell or promote (enhance, increase, stimulate, allow) cell survival, even in the presence of conditions that could induce apoptosis. Proteins associated with apoptosis, and the genes encoding such proteins, are well-known in the art. Such other genes include, but are not limited to, any genes in the Bcl-2 family that will likely be important in the setting of conditional transformation of adult stem cells (i.e., not just hematopoietic stem cells). These genes include, but are not limited to, other pro-survival members of the Bcl-2 family, such as Bcl-X, Bcl-w, BclXL, Mcl-1, Dad-1, or hTERT (reverse transcriptase component of the human telomerase, which has been shown to inhibit proliferation). Such genes are ectopically overexpressed in the presence of the regulated oncogene, as described with Bcl-2 in the working examples herein. In addition, this aspect of the present invention includes using shRNA mediated gene knockdown (or disruption or inhibition by any other method) for BH3-only members of the bcl-2 family that are proapoptotic (e.g., Bim, PUMA, NOXA, Bax, Bak, BclXS, Bad, Bar, and others), as well as disruption of Caspases 3, 9, 10, MLL-1 (and all mammalian forms), Enl-1 (Endospermless-1) and all mammalian forms, Apaf-1 and other elements that form part of the apoptosome.

The nucleic acid sequence for each of these genes described above or the coding region thereof is known in the art and is publicly available, including for humans. Similarly, the amino acid sequence for proteins encoded by these genes is known in the art and is publicly available.

The present inventors have produced several different long-term, conditionally immortalized stem cells using the method of the present invention and using different combinations of protooncogenes and anti-apoptotic genes, including the following combinations: MYC-ER and Bcl-2; MYC- ER and hTERT (reverse transcriptase component of the human telomerase); ICN-1-ER and Bcl-2; ICN-1-ER and hTERT; and MYC-ER and ICN-1-ER.

It is noted that with regard to either of the protooncogene or the gene encoding an anti-apoptosis protein used in the present method, it is not required that the entire gene be used in the constructs described herein, since any portion of the gene or a nucleic acid sequence (e.g., cDNA) that encodes the desired functional protein product, a functional portion thereof, or a functional homologue thereof is encompassed by the invention. Accordingly, reference generally herein to the genes or transgenes used to transfect stem cells is to be understood to be exemplary and to include the use of any nucleic acid molecules encoding the entire gene, the entire coding region of the gene, or portions of the genes or homologues thereof, as long as such nucleic acid sequences encode functional proteins suitable for use in the present invention.

In one embodiment of the present invention, the present method additional includes the use of shRNAs or siRNAs that are directed against RNAs encoding proapoptotic proteins, such as the pro-apoptotic members of the Bcl-2 family, namely those of the BH3-only type (Bim, Bax, Bak, Puma, Noxa, etc.). The disruption of a pro-apoptotic gene in the context of a regulated oncogene is expected to result in a more efficient immortalization of certain stem cell populations. RNA interference (RNAi) is a process whereby double stranded RNA, and in mammalian systems, short interfering RNA (siRNA) or short hairpin RNA (shRNA), is used to inhibit or silence expression of complementary genes. In the target cell, siRNA are unwound and associate with an RNA induced silencing complex (RISC), which is then guided to the mRNA sequences that are complementary to the siRNA, whereby the RISC cleaves the mRNA. shRNA is transfected into a target cell in a vector where it is transcribed, and then processed by DICER enzymes to form siRNA-like molecules that activate RISC, which, as with siRNA, is then guided to the mRNA sequences that are complementary to the siRNA, whereby the RISC cleaves the mRNA.

The stem cells can be transfected with the vectors comprising the protooncogene and encoding the anti-apoptosis protein using any suitable method of transfecting cells, and particularly mammalian cells, including by using combinations of techniques. The present inventors have discovered that it is the particular coordination between the genes (or constructs) that are expressed that have resulted in the generation of conditionally immortalized, long term stem cells as described herein. The Examples have demonstrated the use of retroviral vectors, but other methods include, but are not limited to, the use of other viruses and viral vectors derived therefrom, including, but not limited to, lentivirus vectors, parvovirus, vaccinia virus, coronavirus, calicivirus, papilloma virus, flavivirus, orthomixovirus, togavirus, picornavirus, adenoviral vectors, modified and attenuated herpesviruses. Any such virus can further be modified with specific surface expressed molecules that target these to HSCs or other stem cells, such as membrane bound SCF, or other stem-cell specific growth factor ligands. Other methods of transfection of mammalian cells include, but are not limited to, direct electroporation of mammalian expression vectors, such as by using NUCLEO-FECTOR™ technology (AMAXA Biosystems). This technology is a highly efficient non-viral gene transfer method for most primary cells and for hard-to-transfect cell lines, which is an improvement on the long-known method of electroporation, based on the use of cell-type specific combinations of electrical current and solutions to transfer polyanionic macromolecules directly into the nucleus. Additionally, suitable methods of transfection can include any bacterial, yeast or other artificial methods of gene delivery that are known in the art.

The step of expanding the transfected stem cells or culturing the stem cells and exogenous fusion proteins (e.g., the Tat-fusion proteins described in the variations of this method described below) in the presence of suitable growth factors can include the use of any suitable culture conditions, including those specifically described herein. The combination of suitable stem cell growth factors can include any stem cell factors that allow transfected (e.g., transduced) cells of the invention to grow, survive and proliferate in culture. While specific combinations are described herein, and while this is an important step of the present method, this step can be simply described as providing any combination of growth factors that are suitable for the growth, proliferation and survival of stem cells, and include any combinations that are known in the art. Accordingly, the invention is not limited to a particular combination. One preferred combination of growth factors includes: interleukin-6 (IL-6), IL-3 and stem cell factor (SCF). Another preferred combination of growth factors includes stem cell factor (SCF), thrombopoietin (TPO), insulin-like Growth Factor 2 (IGF-2) and fibroblast Growth Factor 1 (FGF-1), in serum-free media. This latter combination was recently described in Zhang and Lodich (2005; Murine hematopoietic stem cells change their surface phenotype during ex vivo expansion, *Blood* 105, 4314-20). The stem cells transfected with nucleic acid molecules encoding the combinations proteins described herein (e.g., MYC-ER and Bcl-2 as described in the examples) are expected to also become conditionally immortalized in this cocktail of growth factors, as with the cocktail described in the Examples above (using IL-3, IL-6 and SCF). Other growth factors for use in the invention include, but are not limited to, angiopoietin-like proteins (e.g., Agptl2, Angptl3, Angptl5, Angptl7, etc.), proliferin-2 (PLF2), glycogen synthase kinase-3 inhibitors, inducers of the wnt and Notch signaling pathways, Flt3L and related cytokines, fibroblast growth factor 2 (FGF2) and related cytokines, writ-1 and other activators of the Wnt pathway, Sonic hedgehog (shh-1) and other activators of that pathway. Other suitable combinations of growth factors will be applicable to the method of the present invention and will be apparent to those of skill in the art. Indeed, the cell lines generated using the method of the present invention can readily be used to screen for additional cytokines and growth factors that could be used for expanding long-term stem cells, or any of their derived progenitors, in vitro under neutral or directed conditions.

According to the present invention, a medium suitable for culture of animal cells can include any available medium which has been developed for culture of animal cells and particularly, mammalian cells, or which can be prepared in the laboratory with the appropriate components necessary for animal cell growth, such as assimilable carbon, nitrogen and micronutrients. Such a medium comprises a base medium, which is any base medium suitable for animal cell growth, including, but not limited to, Iscove's Modified Dulbecco's Medium (IMDM), Dulbecco's modified Eagles medium (DMEM), alpha MEM (Gibco), RPMI 1640, or any other suitable commercially available media. To the base medium, assimilable sources of carbon, nitrogen and micro-nutrients are added including, but not limited to, a serum source, growth factors, amino acids, antibiotics, vitamins, reducing agents, and/or sugar sources. It is noted that completed mediums comprising a base medium and many of the additional components necessary for animal cell growth are commercially available, and some media are available for particular types of cell culture. In addition, many serum-free media are available and may be particularly suited for the culture of stem cells according to the invention.

Cells and Compositions

Another embodiment of the present invention relates to a cell, cell line, or population of cells produced according to the method of the present invention as described herein. Also included in the invention are compositions comprising such cells, cell lines or populations of cells. For therapeutic methods, such compositions can include a pharmaceutically acceptable carrier, which includes pharmaceutically acceptable excipients and/or delivery vehicles, for delivering the cells, cell lines, or cell populations to a patient. As used herein, a pharmaceutically acceptable carrier refers to any substance suitable for delivering a therapeutic composition useful in the method of the present invention to a suitable in vivo site.

Adaptation of the Method of the Invention to Produce Cell Lineages at Intermediate Stages of Development Another embodiment of the present invention relates to adaptations of the novel methods described herein to generate cell lines that capture intermediate stages of development for the hematopoietic lineages. According to the present invention, an "intermediate" stage of development or differentiation refers to a pluripotent stage of cell development or differentiation that is downstream of the stage of development or differentiation of the stem cell from which the "intermediate" cell was derived, but is upstream of the final, or terminal, point of differentiation of a cell. For example, a pre-B cell is an intermediate stage of a hematopoietic stem cell, which can still differentiate into a mature B cell. Intermediate stages of development or differentiation will be understood by those of skill in the art.

More particularly, for many therapeutic and discovery or research applications, as well as for storage of cells lines, it is desirable that the cell lines have a stable phenotype and retain their ability to further differentiate along their committed pathway once the active oncogene with which the cell has been transfected is turned off. Accordingly, the present invention encompasses additional steps of producing cells that have not fully differentiated (are not terminally differentiated), but rather, are at an intermediate stage of differentiation. In one non-limiting example of this embodiment, long-term stem cells-produced using the method described above are randomly differentiated in vitro following withdrawal of the conditions that maintain the activity of the protooncogene or other gene that promotes cell survival and proliferation (e.g., 4-OHT in the case of the tamoxifen-dependent protooncogenes), or by applying the appropriate conditions that turn off (inactivate) the protooncogene/oncogene. This step can be performed while maintaining the culture in neutral cytokine growth conditions (e.g., IL-3, IL-6 and SCF), or by replacing those cytokines which could specifically direct differentiation towards a certain lineage (e.g., IL-7 and Notch ligands for lymphoid lineages, GM-CSF and IL-4 for dendritic cells, G-CSF for myelomonocytic cells, etc.) with cytokines that are neutral for differentiation (do not direct or drive differentiation of the cells). Once the cultures begin to display differentiation markers consistent with a specific lineage, the culture media is again supplemented with the conditions that activate the protooncogene (e.g., 4-OHT) or exposed to the conditions that otherwise reactivating the protooncogene, in order to stabilize the phenotype and generate cell lines having a stable, intermediate differentiation phenotype.

By way of exemplification of this method, the inventors have generated CD4+, αβ+ T cells in vitro from ABM42 cells (lt-HSC produced by the method of the invention; see Examples) by withdrawal of 4-OHT from the media, and re-addition of 4OHT after differentiation. The inventors have also generated dendritic cell lines by incubating ABM46 cells (see Examples) in GM-CSF, IL-4 and FLT3L and then placing the cultures back in the presence of 4-OHT after differentiation.

Another approach for creating such cell lines involves introducing the ctlt-HSC cells into mice to allow for differentiation, and arresting, or stabilizing the phenotypes in vivo after injections of 4-OHT. This method is described in detail in Example 8. Briefly, and by way of example, lt-HSC generated by the present method are injected into immuno-compromised animals (e.g., immuno-compromised mice). The oncogene in the lt-HSCs is reactivated using injections of the activating agent (e.g., 4-OHT), cells are later collected, and then the cells can be cultured in vitro to differentiate the cells, and then stored or used as desired. This approach, and the other described above, can be used for both murine and human ctlt-HSC cell lines, such as by using either NOD/SCID mice as the recipients, or neonatal Rag-1$^{-/-}$ mice, which will be given intrahepatic injections.

Application of the Method of the Invention to Embryonic Stem Cells

Another embodiment of the invention relates to the application of the method of conditionally immortalizing stem cells to embryonic stem (ES) cells. Such methods will be useful for generating cell lines that are more readily derived from ES cells, such as cells of the neuronal linage, including neuronal stem cells.

In this embodiment, the method of the present invention, comprising the transduction of cells (in this case, ES cells) with a protooncogene and a gene that inhibits apoptosis (e.g., MYC-ER and Bcl-2) can be applied to ES cells to further control the directed differentiation of these cells. In this embodiment, such cells can be used to generate transgenic mice, for example, and in addition, any ES cell and relevant progenitor cell population derived therefrom can be subjected to the activation of the protooncogene by exposure to the activating agent, hence allowing for the generation of novel conditionally transformed stem cell lines (different tissue types), or mature cell lines for the tissue type of interest. In addition, the directed differentiation of transduced ES cells in vitro can also be used to capture intermediate states of differentiation by as described above. The use of ES cells or ES-derived cells in this manner provides a novel platform for drug discovery and target identification in the setting of different diseases.

For example, neuronal stem cells can be employed in this embodiment of the invention, as well as the directed differentiation of ES cells into the neuronal pathway using the method of the invention. The isolation and transduction of neuronal stem cells from the hippocampus has been previously described for mice. The culture conditions for neurospheres would enable the proliferation of those cells, rendering them susceptible to viral-mediated transduction of the genes of the invention (e.g., MYC-ER and Bcl-2), in order to generate conditionally transformed neuronal stem cell lines. Their differentiation in vitro as well as in vivo following implantation can be monitored by virtue of the virally encoded reporter genes as well as previously defined markers of neuronal differentiation. In addition, the administration of the activating agent (e.g., 4-OHT) to the mice following transplantation of the conditionally transformed neuronal stem cell lines may lead to the development of a neurological malignancy (neuroblastoma, glioblastoma, etc.). Those tumors would provide a novel model for preclinical studies and target identification.

The directed differentiation of ES cells that had been transduced with, for example, MYC-ER and Bcl-2, can be carried out in the presence of a previously defined growth medium, as well as cytokines. The addition of the activating agent (e.g., 4-OHT) at any time during the culture will enable the stabilization of the cells at an intermediate phenotype, and leads to the generation of cell lines that still retain the capacity to undergo further differentiation. For instance, the generation of dopaminergic neurons from ES cells is normally done by the addition of Retinoic acid and FGF8. This type of neuron would be ideal for repairing brain lesions observed in Alzheimer's patients. However, the transplantation of fully differentiated neuronal cells may preclude their successful implantation and engraftment. A conditionally transformed cell line that was committed to the dopaminergic neuronal pathway, but still retained its ability to further differentiate after transplant, as envisioned herein, is expected to greatly increase the chances of implantation and successful engraftment. A similar scenario can be proposed for the generation of motor neurons from ES cells, by adding Retinoic acid and a sonic hedgehog agonist to the cultures. Those neuronal cells could help repair spinal cord injuries. Once again, fully differentiated cells would not be used in this embodiment, but rather, the committed progenitor cells that retain the capacity to differentiate (produced by the method of the invention) would be employed.

Variations or Modifications of the Method of Conditional Immortalization for the Removal of the Transgene In one embodiment of the invention, in order to avoid taking the risk of introducing stem cells that harbor transgenes such as those described herein (e.g., MYC-ER) into humans and/or mice, the recombinant constructs are designed so that these DNA fragments will be excised. This embodiment can be achieved using any suitable method of first establishing the long-term stem cells according to the method of the invention, and then exposing the cells (or a patient) to conditions under which the recombinant DNA will be removed, excised or completely silenced.

For example, in one aspect of the invention, a bacterial recombinase approach is used. In this aspect of the invention, preferably, two different recombinases are used in order to allow control over which one of the two genes is excised at any one point in time. Two examples of such recombinases are the Cre and Flp recombinases, which are well-known in the art. Briefly, the recognition substrate sequences (RSS's) for one of the recombinases is introduced into the retroviral constructs such that they flank the open reading frame of the oncogene, as well as the reporter gene (e.g., GFP or Thy1.1). In this case, the cells are incubated in media containing a Tat-Cre fusion protein (i.e., HIV or other retroviral Tat protein fused to Cre). This recombinant protein has been previously described and shown to be able to passively enter cells, and mediate loxP site-dependent recombination of genomic DNA. Other methods of gene (nucleic acid molecule) excision are known to those of skill in the art and could readily be applied to the present invention. Examples 5 and 13 exemplify this embodiment of the invention.

In another embodiment of the invention, to provide another method of avoiding the risk of introducing stem cells that harbor transgenes such as those described herein into humans and/or other animals (e.g., mice), instead of transfecting the stem cells with the combination of the recombinant constructs for the protooncogene or the anti-apoptosis protein, the invention is performed by making use of Tat-fusion proteins as a method to allow the proteins access to the inside of the cell without having to introduce transgenes into the cell. For example, recombinant constructs that encode tat-protooncogene or tat-anti-apoptosis genes (e.g., Tat-MYC-ER or Tat-Bcl-2) may be used to conditionally immortalize stem cells. In this embodiment of the invention, the target stem cells will be cultured under suitable culture conditions, in media that contains purified recombinant Tat-fusion proteins encoded by the specific gene combination selected (e.g., MYC-ER and Bcl-2). In this embodiment of the invention, the protooncogene product or similar gene product can be inducible, as in the embodiments above. Alternatively, or in addition, the action of this protein can be regulated simply by providing or removing the protein from the culture. While the cell lines that are generated with this approach will be continuously dependent upon the addition of the exogenous Tat-fusion proteins, they will not have a specific exogenous nucleotide sequence introduced into them. The absence of foreign oncogene sequences is expected to improve the clinical deployment of the method of the present invention. Human immunodeficiency virus-1 (HIV-1) Tat, is one exemplary Tat protein, although other retroviral Tat proteins are known in the art. As a non-limiting example, the nucleic acid sequence encoding HIV-1 Tat is represented herein as SEQ ID NO:9, which encodes an amino acid sequence represented herein by SEQ ID NO:10.

In another embodiment, to provide another method of avoiding the risk of introducing stem cells that harbor transgenes such as those described herein into humans and/or other animals (e.g., mice), instead of transfecting the stem cells with the combination of the recombinant constructs for the protooncogene or the anti-apoptosis protein, the invention is performed by introducing proteins (e.g., MYC and Bcl-2) into a cell using aptamer technology. Aptamers are short strands of synthetic nucleic acids (usually RNA but also DNA) selected from randomized combinatorial nucleic acid libraries by virtue of their ability to bind to a predetermined specific target molecule with high affinity and specificity. Aptamers assume a defined three-dimensional structure and are capable of discriminating between compounds with very small differences in structure. Accordingly aptamers can be conjugated with the proteins used in the invention or with non-integrating cDNA encoding the proteins, for example, and used to deliver the proteins or DNA to the cells. In addition, aptamers can readily be used to deliver siRNA to cells, for example, when one disrupts proapoptotic proteins according to the present invention. Aptamer technology is discussed, for example, in Davidson, 2006, *Nature Biotechnol.* 24(8):951-952; and McNamara et al., 2006, *Nature Biotechnol.* 24(8):1005-1015). Again, the absence of foreign oncogene sequences is expected to improve the clinical deployment of the method of the present invention.

In another embodiment, to provide another method of avoiding the risk of introducing stem cells that harbor transgenes such as those described herein into humans and/or other animals (e.g., mice), instead of transfecting the stem cells with the combination of the recombinant constructs for the protooncogene or the anti-apoptosis protein, the invention is performed by introducing the protooncogene and/or anti-apoptosis protein into a cell using CHARIOT™ technology (Krackeler Scientific, Inc, Albany, N.Y.). With this technology, a non-covalent bond is formed between a CHARIOT™ peptide and the protein of interest. This protects the protein from degradation and preserves its natural characteristics during the transfection process. Upon delivery to a cell, the complex dissociates and CHARIOT™ is transported to the nucleus, while the delivered protein is biologically active and free to proceed to its cellular target. Efficient delivery can occur in the presence or absence of serum, and is independent of the endosomal pathway, which can modify macromolecules during internalization. This delivery system also bypasses the transcription-translation process. Accordingly, the proteins useful in the present invention can be delivered to a cell and released to conditionally immortalize the cell, without the need for the introduction of a protooncogene or oncogenes to the cell. As above, the absence of foreign oncogene sequences is expected to improve the clinical deployment of the method of the present invention.

As yet another alternative (or additional) means to control for the possibility of an insertion of a protooncogene into the host cell genome by the various viral approaches described herein, and thereby avoid a transforming event, a drug sensitivity (drug susceptibility) cassette can be introduced into the viral constructs to be used such that it will be expressed in every transduced cell and its differentiated progeny. A drug sensitivity cassette or a drug susceptibility cassette is a nucleic acid sequence encoding a protein that renders a cell susceptible or sensitive to the presence of a particular drug, so that upon exposure to the drug, the cell activity is inhibited and preferably, undergoes apoptosis. Those patients in which the levels of a particular blood cell population increases without apparent cause (e.g., infection, trauma, stress, etc.), can be given a course of the drug to which sensitivity has been introduced in order to ablate those cells and mitigate any possible additional complications involving cells in which the genetic insertions may have inadvertently caused an oncogenic mutation. Accordingly, as a non-limiting example, one could introduce into a construct used in the method of the invention a cassette that encodes the cDNA for HPRT in order to render the transduced cells susceptible to 6-thioguanine. Another non-limiting example is the introduction of the thymidine kinase cDNA from a Herpes-simplex virus family member (HSV-TK), in order to render the transduced cells susceptible to relevant inhibitors such as Ganciclovir, Acyclovir, and any relevant derivatives. In addition, any other such drug sensitivity cassettes and their relevant agonists would work in this context.

Other methods of introducing nucleic acids or proteins according to the present invention into a cell will be apparent to those of skill in the art. Those that minimize or eliminate the risk of introducing recombinant DNA into a host cell genome are preferred by the invention, many such examples being described above.

Methods of Use for Conditionally Immortalized Cells of the Invention

Another embodiment of the present invention includes any of the stem cell populations, including mixed and clonal populations, that are produced by the method of the invention, as well as the use of the stem cells of the invention in any of the methods described herein, including differentiation into a desired cell type, and any method of transplantation, cell replacement, disease therapy, genetic engineering, drug discovery, and investigation of cell development and differentiation as described herein.

Since one can now produce virtually unlimited supplies of homogeneous stem cells that can readily be stored, recovered, expanded and manipulated, such stem cells can be used as stem cells or differentiated into various cell lineages and used in assays to test various compounds for effects on cell differentiation, gene expression, and cell processes. Therefore, one embodiment of the invention relates to a method to identify compounds that effect cell differentiation, gene expression, and/or cell processes. The method generally includes the steps of contacting stem cells produced by the method of the present invention with a compound to be tested, and measuring a particular result, and particularly a desired result, such as gene expression, a biological activity, cell differentiation, cell growth, cell proliferation, etc. (see below), as compared to in the absence of the compound, to determine whether or not the test compound had the desired effect on the stem cell. This method can be used to test for virtually any aspect of cell differentiation, cell activity or gene expression. In one aspect, the stem cells are manipulated prior to contact with the compounds, such as by genetic manipulation. Stem cells from individuals with genetic defects can be evaluated in such assays in order to identify therapeutic compounds (e.g., cancer therapeutics) and to evaluate gene replacement therapies, for example. Indeed, the technology of the present invention provides an opportunity to target the cells of a specific individual to identify drug candidates and therapeutic candidates and strategies that are "tailored" to the cells of an individual. Furthermore, as discussed above, such assays can also be used to identify other growth factors or culture conditions that are suitable for maintaining the stem cells of the invention in culture. An example of such an assay is described in detail below in Example 7, although the invention is not limited to this assay.

Another embodiment of the invention relates to a method to study cell lineage commitment and/or differentiation and development of cells from a stem cell, which generally comprises culturing the conditionally immortalized stem cells of the present invention and evaluating such cells for genetic and biological markers related to cell development and differentiation under various conditions and in the presence and absence of compounds or agents that may affect cell lineage commitment or differentiation. As discussed above, prior to the present invention, such studies were severely hampered by the lack of access to and the inability to generate sufficient numbers of the desired cell population to perform desired experiments. For example, in order to identify or screen for intermediates in the differentiation of a particular progenitor cell line, a sufficient number of cells must be obtained to provide meaningful and reproducible results. Using technologies available at the time of the invention, this was not possible. However, the present invention solves the problem by providing expandable and essentially unlimited supplies of homogeneous stem cells that can be used in a variety of experiments. This technology will greatly enhance research capabilities in the area of cell differentiation and discovery. In one aspect, conditionally immortalized stem cells of the invention are expanded, and then a subset are cultured in the absence of the conditions that maintain the cells in the conditionally immortalized state (e.g., in the absence of tamoxifen, according to the exemplary method illustrated herein). The cells can be evaluated for changes in gene expression, cell surface markers, secretion of biomolecules, or any other genotypic or phenotypic marker, to study the process of cell differentiation and lineage commitment. Growth factors or other factors can be added to the cultures, for example to drive differentiation down a particular cell lineage pathway, and the changes in the cells can be evaluated in the presence or absence of such factors. Furthermore, the cells can be used to evaluate culture conditions, in vivo conditions, factors, and agents that influence (regulate) cell differentiation and development.

Various methods of detection of changes in genotypic or phenotypic characteristics of cells in any of the assays of the invention are known in the art. Examples of methods that can be used to measure or detect gene sequence or expression include, but are not limited to, polymerase chain reaction (PCR), reverse transcriptase-PCR (RT-PCR), in situ PCR, quantitative PCR (q-PCR), in situ hybridization, Southern blot, Northern blot, sequence analysis, microarray analysis, detection of a reporter gene, or other DNA/RNA hybridization platforms. Methods to measure protein levels, include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), flow cytometry, and assays based on a property of the protein including but not limited to DNA binding, ligand binding, interaction with other protein partners, cell signal transduction, enzyme activity, and secretion of soluble factors or proteins.

In drug screening assays, the term "test compound", "putative inhibitory compound" or "putative regulatory compound" refers to compounds having an unknown or previously unappreciated regulatory activity in a particular process. As such, the term "identify" with regard to methods to identify compounds is intended to include all compounds, the usefulness of which as a compound for a particular purpose (e.g., regulation of cell differentiation) is determined by a method of the present invention, preferably in the presence and absence of such a compound. Compounds to be screened in the methods of the invention include known organic compounds such as antibodies, products of peptide libraries, and products of chemical combinatorial libraries. Compounds may also be identified using rational drug design. Such methods are known to those of skill in the art and can involve the use of three-dimensional imaging software programs. For example, various methods of drug design, useful to design or select mimetics or other therapeutic compounds useful in the present invention are disclosed in Maulik et al., 1997, *Molecular Biotechnology: Therapeutic Applications and Strategies*, Wiley-Liss, Inc., which is incorporated herein by reference in its entirety.

In any of the above-described assays, the conditions under which a cell, cell lysate, nucleic acid molecule or protein of the present invention is exposed to or contacted with a putative regulatory compound, such as by mixing, are any suitable culture or assay conditions, which can include the use of an effective medium in which the cell can be cultured (e.g., as described above) or in which the cell lysate can be evaluated in the presence and absence of a putative regulatory compound. Cells of the present invention can be cultured in a variety of containers including, but not limited to, tissue culture flasks, test tubes, microtiter dishes, and petri plates. Culturing is carried out at a temperature, pH and carbon dioxide content appropriate for the cell. Such culturing conditions are also within the skill in the art, and particularly suitable conditions for culturing conditionally immortalized stem cells of the present invention are described in detail elsewhere herein. Cells are contacted with a putative regulatory compound under conditions which take into account the number of cells per container contacted, the concentration of putative regulatory compound(s) administered to a cell, the incubation time of the putative regulatory compound with the cell, and the concentration of compound administered to a cell. Determination of effective protocols can be accomplished by those skilled in the art based on variables such as the size of the container, the volume of liquid in the container, conditions known to be suitable for the culture of the particular cell type used in the assay, and the chemical composition of the putative regulatory compound (i.e., size, charge etc.) being tested.

In one embodiment of the invention, the cells and methods of the invention are useful for methods directed at evaluating pluripotency of ctlt-HSCs derived from human cord blood, CD34+ cells, or adult CD34+ cells isolated from peripheral blood. Such a method is described in Example 11.

Yet another embodiment of the invention relates to the use of tilt-HSC cell lines as a platform to generate novel models of Acute Myeloid Leukemia (AML). More particularly, the present inventors have generated a mouse model of acute myeloid leukemia using the ctlt-HSCs of the invention. These are leukemias composed of cells that resemble HSCs, based on their surface marker expression. In order to generate ctlt-HSCs to promote leukemia in mice, $10^3$-$10^5$ ctlt-HSCs are transferred along with $10^5$ Rag-$1^{-/-}$ whole bone marrow cells into lethally irradiated recipient mice. The mice are given weekly doses of 4-OHT in order to maintain oncogene activity, and monitored for clinical signs associated with leukemia, as known in the art. Tumors have been recovered from these animals and they can be propagated in culture in the absence of 4-OHT. Those cells retain their HSC-like phenotype, indicating that they are no longer exquisitely dependent upon MYC hyperactivity in order for proliferation, survival and arrested differentiation. The leukemic cell lines can also confer the disease upon secondary transplantation to irradiated recipient mice. These tools provide a novel platform for studying the biology and exporting new therapeutic avenues for AML and related diseases. Furthermore, the introduction of ctlt-HSC cell lines into mice that are treated with 4-OHT will provide a good built-in positive control for therapy: the withdrawal of 4-OHT. The secondary cell lines that arose after the establishment of tumors in vivo can also be used to understand the relevant therapeutic targets for drug resistant forms of AML.

Other embodiments of the present invention relate to the use of the stem cells generated by the method of the present invention, as well as cells differentiated from those stem cells, in a variety of therapeutic and health-related methods. These methods generally include the steps of obtaining a population, culture or line of conditionally immortalized stem cells produced by the method of the present invention, removing the conditions under which such cells are conditionally immortalized, and then using the cells in a therapeutic protocol. For example, the cells can be administered directly to an individual in need of the cells or the cells can be differentiated into a desired cell type in vitro and then administered to an individual. In addition, prior to or just after the removal of the conditions under which the cells are immortalized, the cells can be genetically modified in vitro to express or silence a gene or genes, as a novel method of gene therapy under a controlled environment. The cells can then be administered to an individual as stem cells or first differentiated in vitro to a desired cell lineage.

To obtain the stem cells, in one embodiment, stem cells are obtained from the individual to be treated, and are then conditionally immortalized according to the method of the invention. These cells can be expanded extensively, stored (e.g., frozen or cryopreserved), and then retrieved and expanded again, manipulated, and/or used repeatedly as required. In another embodiment, one obtains the stem cells by accessing a previously stored source of conditionally immortalized stem cells from the individual to be treated. In yet another embodiment, the stem cells are obtained from a panel of human stem cell lines that were previously generated and which cover a significant percentage of the population according to the current criteria used to identify "matching" donors. In one embodiment, the cells are obtained from fresh, or cryopreserved cord blood, hematopoietic progenitor populations that can be derived from the directed differentiation of ES cells in vitro, HSCs obtained from the peripheral blood of normal, or G-CSF treated patients who have been induced to mobilize their lt-HSCs to the peripheral circulation. Other sources of stem cells will be apparent to those of skill in the art. The cells are cultured according to the methods described previously herein and the conditions controlling immortalization can be removed at the appropriate time. In addition, prior to administration of the cells to an individual, the cells can be manipulated to excise the genes or constructs that are responsible for the conditional immortalization (i.e., the protooncogene and/or the anti-apoptosis encoding gene), or if the cells are maintained through the use of soluble fusion proteins in the culture medium, as described above for the Tat-fusions, these soluble proteins can be removed from the culture gradually or immediately.

Therefore, the present invention includes the delivery of stem cells produced by the method of the invention (including compositions comprising such stem cells), or cells differentiated from these cells, to an individual (which can include any animal). Since the stem cells used in these methods are produced in vitro, even if stem cells were initially isolated from the patient, the entire administration process of the cells is essentially an ex vivo administration protocol. Ex vivo administration refers to performing part of the regulatory step outside of the patient, such producing the conditionally immortalized stem cells that were removed from an individual (which can include producing genetically modified stem cells in addition to essentially normal stem cells), and returning the cells, or cells differentiated from these cells, to the patient. The stem cells produced according to the present invention or cells differentiated therefrom can be returned to an individual, or administered to an individual, by any suitable mode of administration. Such administration can be systemic, mucosal and/or proximal to the location of a target site. The preferred routes of administration will be apparent to those of skill in the art, depending on the type of condition to be prevented or treated or the reason for administration. Preferred methods of administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, subcutaneous administration, intraarticular administration, intraventricular administration, intraspinal, pulmonary administration, impregnation of a catheter, and direct injection into a tissue (e.g., such as cannulation of the liver, for example).

The cells can be administered with carriers or pharmaceutically acceptable excipients. Carriers are typically compounds that increase the half-life of a therapeutic composition in the treated individual. Suitable carriers include, but are not limited to, polymeric controlled release formulations, biodegradable implants, liposomes, oils, esters, and glycols. As used herein, a pharmaceutically acceptable excipient refers to any substance suitable for delivering cells produced by the method of the present invention to a suitable in vivo site. Preferred pharmaceutically acceptable excipients are capable of maintaining a cells in a form that, upon arrival of the cells at a target tissue or site in the body, the cells are capable of functioning in a manner that is beneficial to the individual.

According to the present invention, an effective administration protocol comprises suitable dose parameters and modes of administration that result in delivery of a useful number of functional cells to a patient in order to provide a transient or long-term benefit to the patient. Effective dose parameters can be determined using methods standard in the art for a particular condition or disease. Such methods include, for example, determination of survival rates, side effects (i.e., toxicity) and progression or regression of disease.

A suitable single dose of stem cells or cells differentiated therefrom according to the present invention is a dose that is capable of providing a beneficial number of cells to a patient, when administered one or more times over a suitable time period. For example, a preferred single dose of stem cells according to the present invention is from about $0.5 \times 10^4$ to about $5.5 \times 10^8$, or from about $0.5 \times 10^5$ to about $5.5 \times 10^7$, or from about $0.5 \times 10^6$ to about $5.5 \times 10^{10}$ stem cells per individual per administration, with doses from about $1 \times 10^8$ to about $5.5 \times 10^{10}$ being even more preferred. Any dose in between $0.5 \times 10^4$ and about $5.5 \times 10^{10}$ is encompassed by the invention, in increments of $10^2$ cells. Higher or lower doses will be known to those of skill in the art depending on the type of stem cell or differentiated cell to be administered, and also depending on the route of administration. It will be obvious to one of skill in the art that the number of doses administered to an animal is dependent upon the extent of the condition or disease and the response of an individual patient to the treatment. Thus, it is within the scope of the present invention that a suitable number of doses includes any number required to treat a given disease.

As used herein, the phrase "protected from a disease" refers to reducing the symptoms of the disease; reducing the occurrence of the disease, and/or reducing the severity of the disease. Protecting an animal (an individual, a subject) can refer to the ability of cells produced according to the present invention, when administered to an animal, to prevent a disease from occurring and/or to cure or to alleviate disease symptoms, signs or causes. As such, to protect an animal from a disease includes both preventing disease occurrence (prophylactic treatment) and treating an animal that has a disease or that is experiencing initial symptoms of a disease (therapeutic treatment). The term, "disease" refers to any deviation from the normal health of a mammal and includes a state when disease symptoms are present, as well as conditions in which a deviation (e.g., infection, gene mutation, genetic defect, etc.) has occurred, but symptoms are not yet manifested.

As discussed above, the stem cells of the present invention can be administered to an individual to treat or prevent a variety of conditions. For example, the stem cell lines of the present invention provide a unique source of expandable stem cells for use in a variety of transplantation and therapeutic strategies, including the treatment of cancer, and particularly, cancer that is treated by radiation. In addition, a variety of immune deficiency disorders and anemia disorders (e.g., aplastic anemia or hemolytic anemia) will also benefit greatly from this technology, since the present invention provides the ability to repopulate hematopoietic cells of an individual as needed by the individual. Another application of the present invention relates to the generation of continuously expandable and renewable hair follicle stem cells, for use, for example in the context of reconstructive surgery for burn victims, for any individual that undergoes chemotherapy and/or radiation therapy resulting in the irreversible loss of hair growth, as well as patients following any surgical procedure affecting the skull or in elective procedures that involve the induction of hair growth in individuals affected by hereditary pattern baldness. Similarly, application of the present invention to stem cells of the skin will be invaluable for use in wound healing and treatment of burn victims, as well as plastic reconstructive surgery for trauma and other patients, as well as elective surgeries, including, but not limited to, cosmetic surgery. Such cells can be additionally genetically manipulated to correct inborn or acquired genetic defects in young and aged individuals. One of skill in the art will understand based on this disclosure that benefits can be derived from the use of the present invention on various other stem cell populations, including, but not limited to, stem cells derived from lung, breast, and intestinal epithelium and stem cells derived from neural and cardiac tissue, to name just a few.

In addition, as discussed above, the present invention provides the unique opportunity for an individual to have access to expandable supplies of autologous stem cells and cells differentiated therefrom as needed throughout the life of the individual. Such stem cells generated by the present method can be stored and used as part of therapeutic protocols during the lifetime of the individual, should they be needed (e.g., in the event the individual develops a cancer or immune deficiency disease).

Genetic defects can now be corrected or beneficial gene modifications can be introduced into somatic cells by manipulating autologous stem cells obtained from an individual that have been conditionally immortalized and expanded using the method of the present invention. The stem cells can then be reintroduced into the individual from whom they were obtained.

Additional applications of the present invention include the use of stem cell lines to repair lung injury that occurs as a result of COPD, IPF, emphysema, asthma and smoking. In addition, such cells could be used to treat blood vessel damage in the heart, and help in autoimmune diseases after lethal irradiation (e.g., SLE, diabetes, RA).

In the method of the present invention, cells produced according to the method of the invention and compositions comprising the cells can be administered to any animal, including any member of the Vertebrate class, Mammalia, including, without limitation, primates, rodents, livestock and domestic pets. A preferred mammal to treat is a human.

Various aspects of the present invention are described in more detail in the following Examples and the attached figures. However, the present invention is not limited to these examples and illustrations of the invention.

EXAMPLES

Example 1

The following example describes the development of a method to reversibly immortalize long-term hematopoietic stem cells (lt-HSCs).

Elucidation of the molecular basis of the impairment in hematopoietic lineage development has been complicated historically by the low frequency of relevant cell populations, which prevents biochemical analysis of signaling and downstream responses. In fact, this has been a major limiting factor in all studies of hematopoiesis. In addition, the limited availability of LT-HSCs has also been a major obstacle in the treatment of many types of cancer as well as several kinds of immune deficiencies in humans.

In an effort to overcome this limitation, the present inventors developed a method to produce conditionally transformed cell lines representing early hematopoietic stem cell progenitors. The initial strategy involved retroviral transduction of bone marrow stem cells from 5FU treated young and immunologically aged 3-83 mice. The inventors utilized the pMSCV bisistronic retroviral vector with inserts encoding Bcl-2 and GFP, and MYC-ER and GFP [Van Parijs, L., Y. Refaeli, A. K. Abbas, and D. Baltimore. (1999) Autoimmunity as a consequence of retrovirus-mediated expression of C-FLIP in lymphocytes. Immunity, 11, 763-70]. These genes were selected because the present inventors knew that MYC has the ability to replace cytokine derived survival and proliferative signals in lymphocytes. By restricting the target cell, the inventors hypothesized that stem cell tumors might form. Importantly, MYC-ER function is tamoxifen dependent in this setting, allowing the termination of MYC function and transformation by withdrawing tamoxifen from the animal or cultures. In cells transduced with MYC-ER, the fusion protein is produced, but is retained in the cytoplasm until exposed to tamoxifen.

Figure 1:
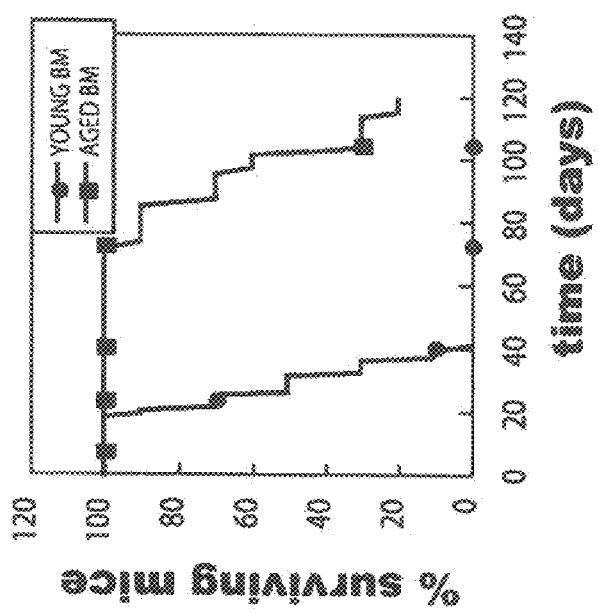

More specifically, stem cell populations from 5FU treated mice were transduced with both retroviruses (encoding MYC-ER and Bcl-2) and transferred into lethally irradiated recipient mice (1200 rads). Ten days later, weekly intraperitoneal injections of 1 mg/mouse of 4-hydroxytamoxifen (4OHT) emulsified in oil were initiated to activate MYC function (FIG. 1). Within four weeks, recipients of young (but not old) transduced stem cells developed tumors. The tumors were harvested from bone marrow, spleen and lymph nodes and cultured in vitro with tamoxifen, but without added cytokines. These cells grew for about 10 days, but then growth stopped and the cells eventually died, the inventors suspected that the cells were differentiating and considered that this might have been due to requirements for cytokines for growth of the cells. Referring to FIG. 1, the curves represent the kinetics of mortality after transplantation and activation of MYC function in vivo. The mice uniformly succumbed to leukemias. While the overexpression of MYC can replace the cytokine-dependent proliferation and survival function, it does not seem to be involved in the cytokine-derived differentiation signals.

Figure 2:
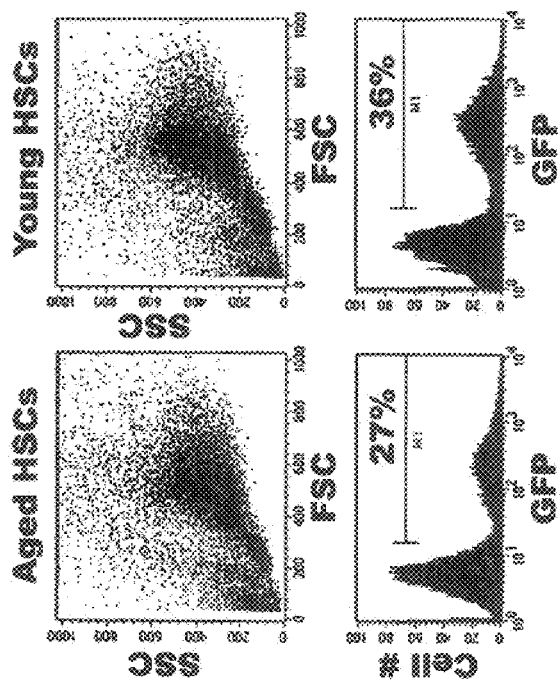

When ill, the mice were euthanized. Bone marrow, spleen and lymph node cells were harvested and placed in culture with tamoxifen and a stem cell growth factor cocktail (IL-6, IL-3 and stem cell factor (SCF)). In parallel, cells were analyzed by flow cytometry (FIG. 2). Referring to FIG. 2, the dot plots represent the flow cytometric data for the forward (FSC) and side (SSC) scatter characteristics of the HSCs after three days in culture with IL-3, IL-6 and SCF. These two criteria correlate with cell size (FSC) and granularity (SSC). The two populations have similar profiles. The histograms represent the levels of GFP expressed in each cell population. This reflects the efficiency of retroviral transduction in vitro with retroviruses that encode cDNAs for MYC-ER and Bcl-2.

Figure 3:
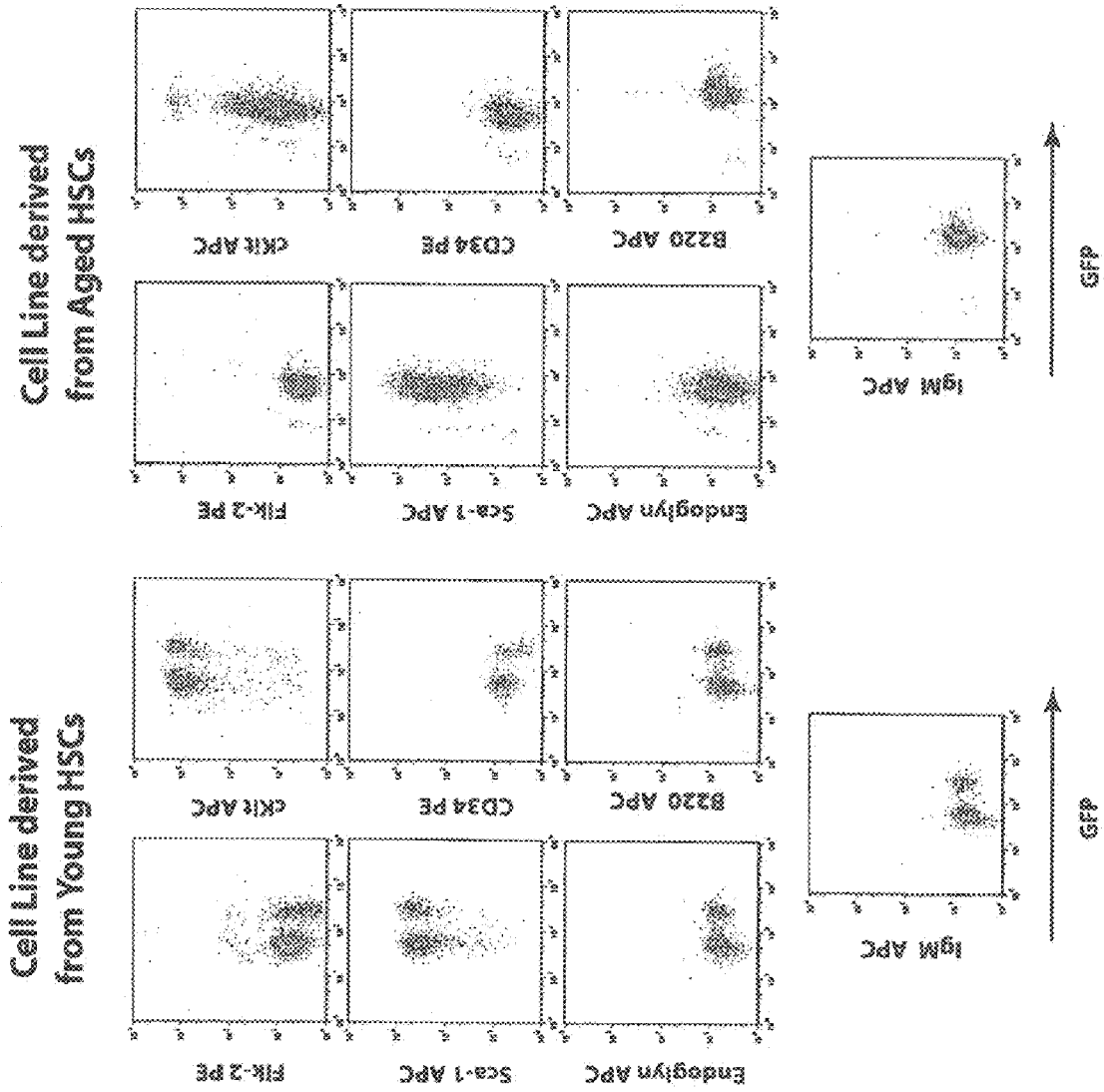

In all cases, ex vivo GFP cells were >90% Sca-1$^+$ and Lineage marker negative. After a few days in culture, cells began to grow and approximately 400 lines were frozen for later study. After propagation, these cells retained expression of EGFP and were homogeneously positive for SCA1 and negative for CD34, Flk2 and lineage markers (FIG. 3). The only difference in marker expression between young mouse-derived and aged mouse-derived markers was increased expression of c-kit in young. Without being bound by theory, the present inventors believe that this may have resulted from longer culture (3 months vs. 3 weeks) of aged lines in c-kit ligand before markers were analyzed. Finally, the inventors discovered that these lines can be recovered easily after freezing and retained their original phenotype. Importantly, these cell lines are homogenous in phenotype and exhibit the phenotype of lt-HSC that provide all long term reconstitution in mice (Reya, T., Duncan, A. W., Ailles, L., Domen, J., Scherer, D. C., Willert, K., Hintz, L., Nusse, R., and Weissman, I. L. (2003). A role for Wnt signaling in self-renewal of hematopoietic stem cells. Nature 423, 409-14).

Recently, the inventors thawed 10 bone marrow derived lines produced as described above, and were able to recover 9 our of 10 of these lines easily by culture in the cytokine cocktail and 4OHT. The inventors phenotyped these tumors, and the results were extremely promising. Specifically, each line contained two distinct cell populations based on forward and 90° light scatter. The nine lines differed only in the proportionality of these populations. The larger of these populations in cell size were uniformly GFP bright and positive for Sca1, Endoglin and ckit but negative for Flt3, B220, CD19 and mIgM. CD34⁻ also appeared to be negative, although this required confirmation (FIG. 3). This phenotype corresponds perfectly with the published characteristics of long term repopulating pluripotent stem cells (Reya et al., supra). The inventors observed the same initial phenotype on the cell lines that they recently obtained from leukemias that developed from transduced HSCs obtained from young donor mice (FIG. 3).

Figure 4:
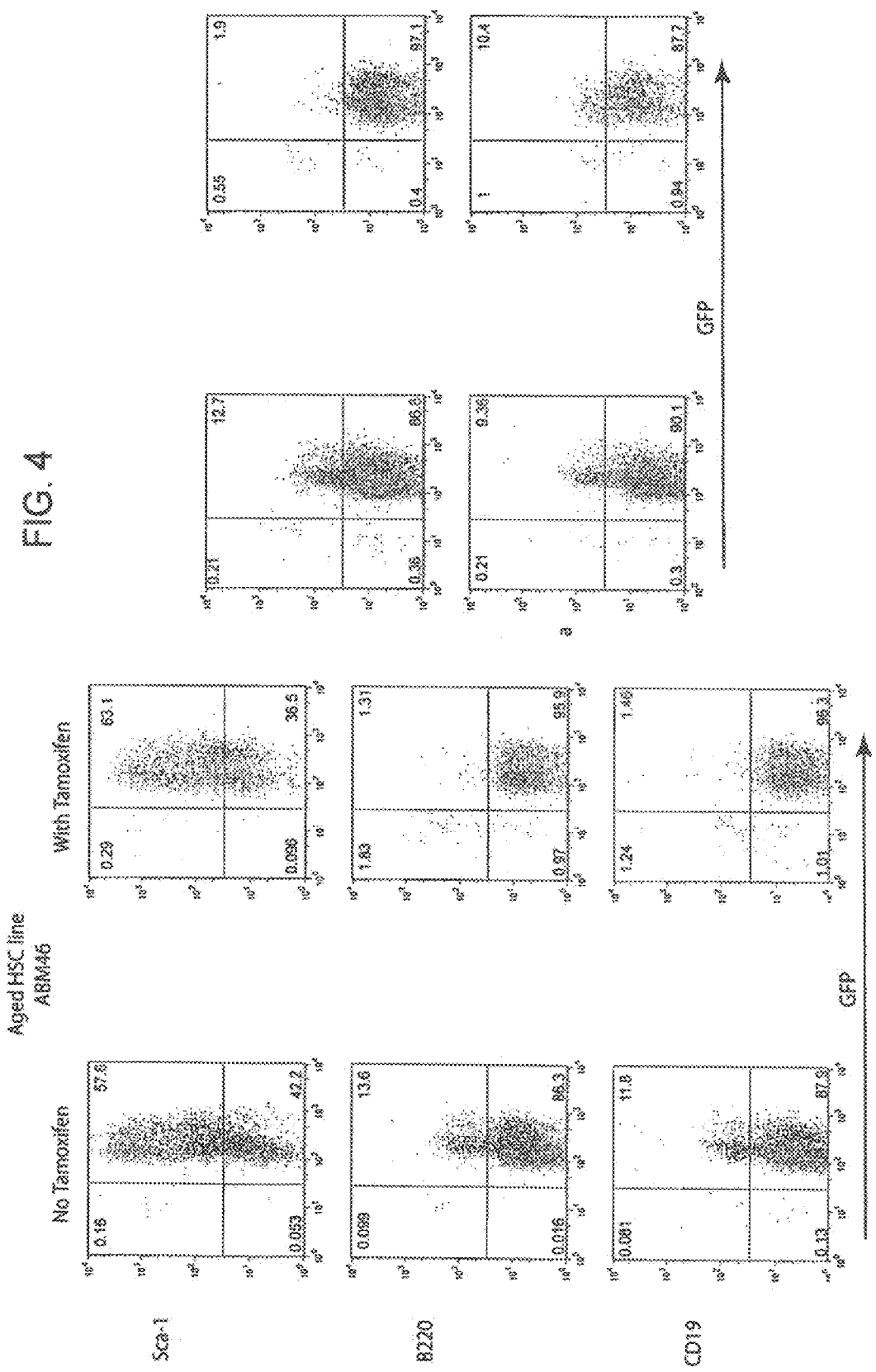
FIG. 4 is a scatter plot showing the spontaneous differentiation of the aged LT-HSC line (ABM46) in vitro following withdrawal of tamoxifen (stem cell and B lineage marker expression are analyzed by flow cytometry).

To test the ability of these cells to differentiate, representative lines were cultured with and without tamoxifen and in the presence of IL-3, IL-6 and SCF to terminate MYC-ER function for 7 days before analyzing phenotypic markers. As shown in FIG. 4, a significant proportion of cells acquired B lineage markers including B220 (~12%), CD19 (~10%) and mIgM (~10%). In addition, the inventors have been able to generate the following lineages in vitro by withdrawal of 4OHT from the cultures: CD4+ ab T-cells, myeloid cells (Mac-1+), ter-119+ erythroid progenitor cells, NK1.1 expressing cells, neutrophils (Gr-1+ cells). Further experiments will assess the ability of these cells to give rise to other lineages, as well as the effect of altering the cytokine regimen on differentiation. Although the comparison has not been performed, the present inventors expect differentiation from young animals, as compared to aged animals to be much more efficient in B cell production. To the best of the present inventors' knowledge, this is the first example of a conditionally immortal hematopoietic stem cell line that can be induced to differentiate in vitro.

Example 2

The following example describes the results of adoptive transfer of LT-HSC lines into lethally irradiated recipients.

If the HSC lines described in Example 1 are to be appropriate subjects for analysis of the basis of defective B cell lymphopoiesis in aged animals, they should recapitulate the defect in vivo. The inventors have begun to address this question by adoptive transfer of LT-HSC lines into lethally irradiated recipients. In initial experiments, lines from aged animals (>60% ID⁻) were transferred along with RAG2⁻/⁻ bone marrow, and recipients were not treated with tamoxifen in order to silence MYC-ER. Six weeks later recipient bone marrow and spleen cells were harvested and the recovery and phenotype of GFP⁺ cells (GFP marks cells derived from HSC lines) was analyzed (FIG. 5).

Figure 5:
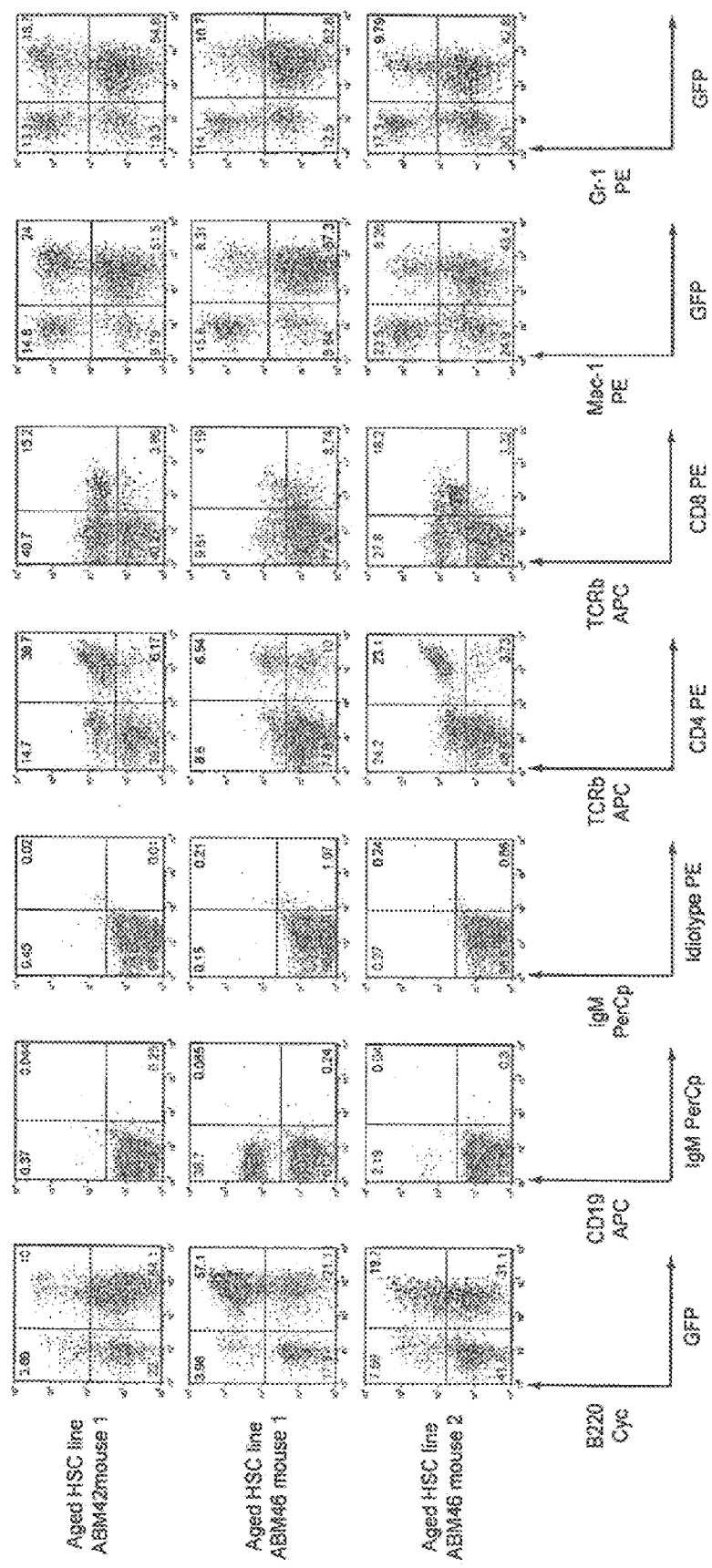
FIG. 5 is a scatter plot showing the analysis of hematopoietic cell compartments derived from LT-HSC lines 6 weeks after adoptive transfer into irradiated young recipients. Data from three mice are presented in this figure, one mouse received the aged HSC line ABM42, and two mice received aged HSC line ABM46.
Figure 6:
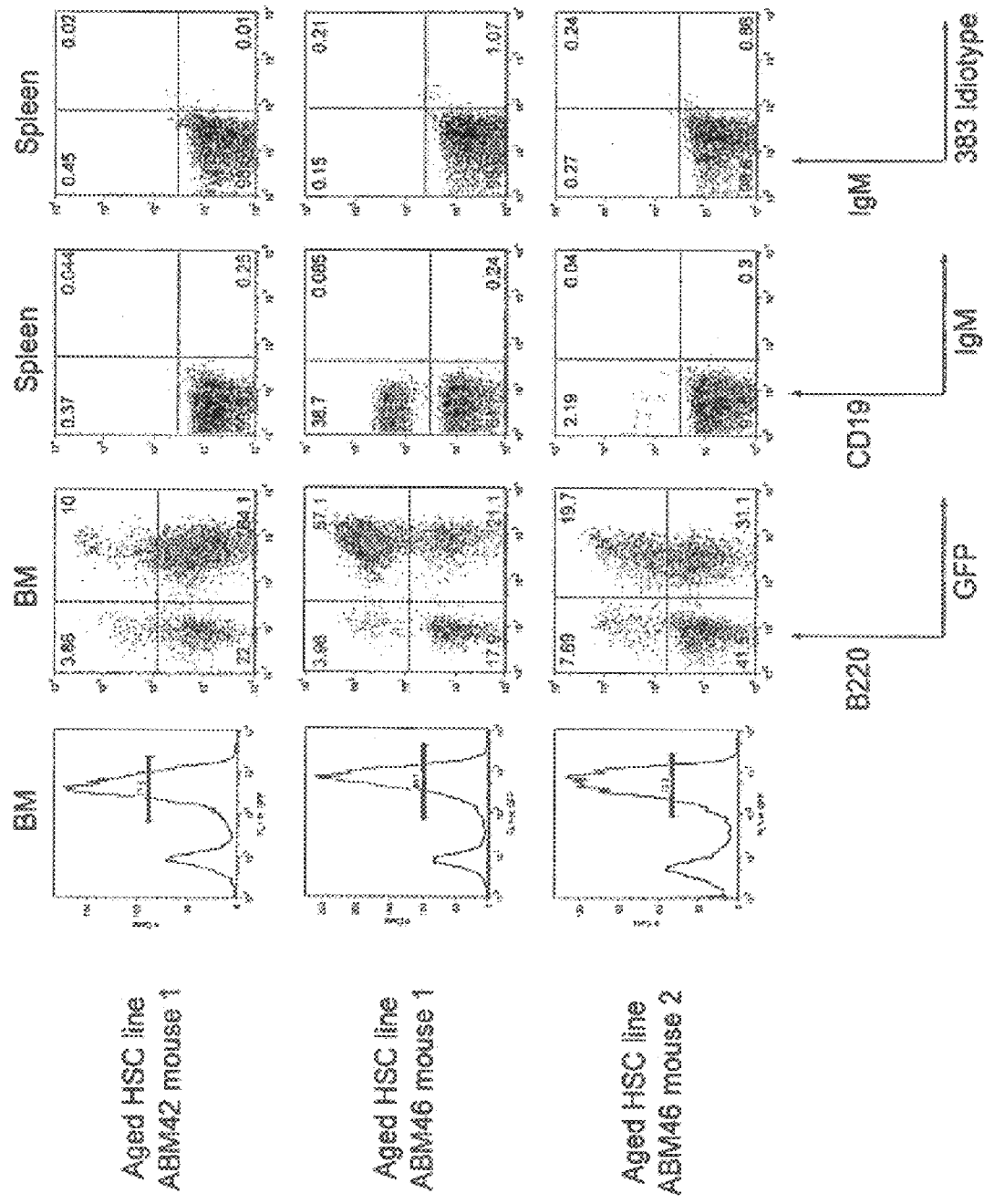
FIG. 6 is a scatter plot showing that the development of the B-cell compartment is compromised in mice reconstituted with ABM42 and ABM46 cell lines. Data from three mice are presented in this figure, one mouse received the aged HSC line ABM42, and two mice received aged HSC line ABM46.
Figure 7:
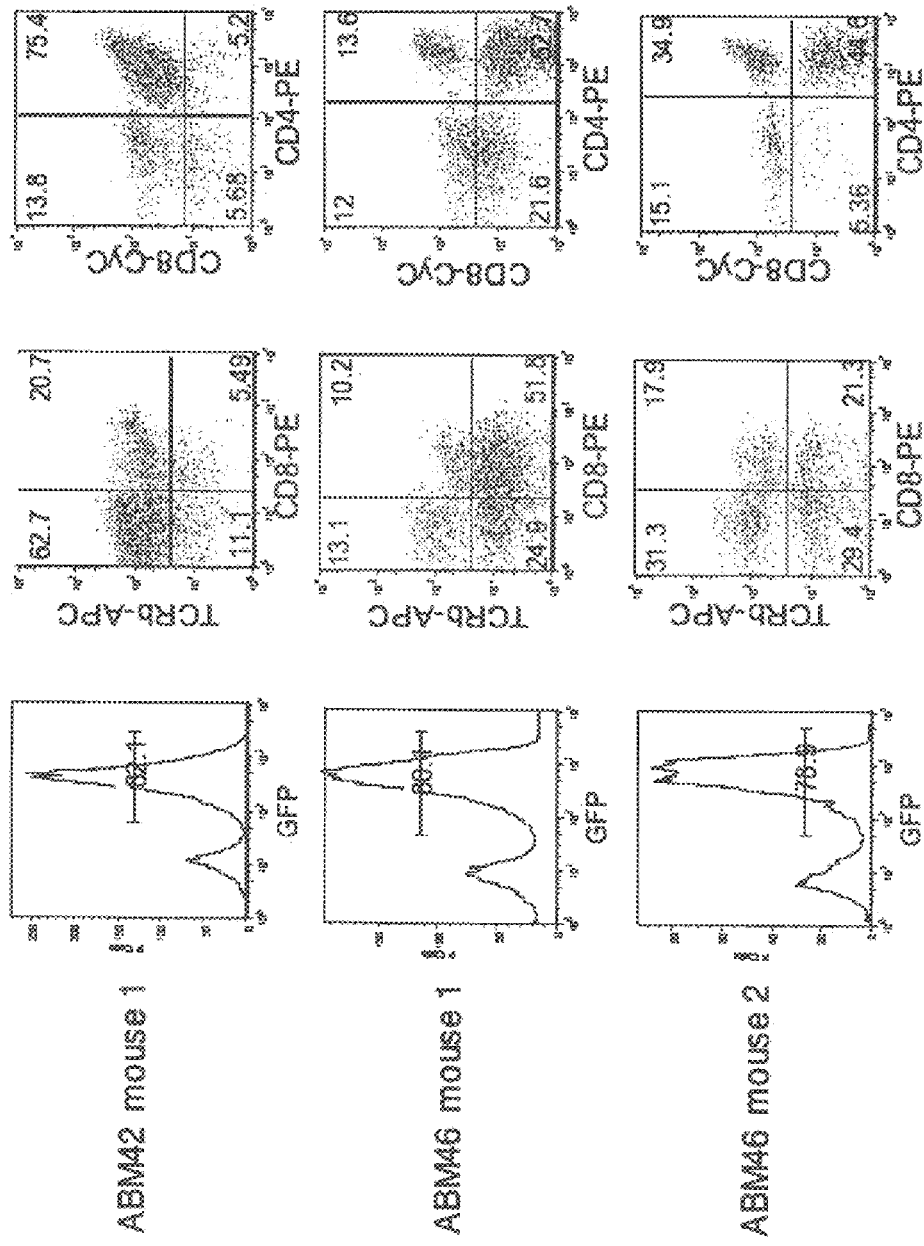
FIG. 7 is a scatter plot showing T-cell development in mice that were reconstituted with ABM42 and ABM46 cell lines. Data from three mice are presented in this figure, one mouse received the aged HSC line ABM42, and two mice received aged HSC line ABM46.

In the data from three mice presented in FIG. 5, one mouse received the aged HSC line ABM42, and two mice received aged HSC line ABM46. Depending upon the line transferred, 30 to 70% of cells in the lymphoid scatter gate were GFP⁺. As shown in FIG. 5, both lines tested (ABM46 and ABM42) gave rise to B (CD19⁺) and T (TCR⁺, CD4⁺, CD8⁺) cells, macrophages (CD11b⁺) and granulocytes (GR1⁺). There was some recipient to recipient variation in the proportionality of these lineages. However, importantly, while both lines tested gave rise to mature CD4 and CD8 single positive T cells (FIG. 7), B cell development did not proceed beyond the progenitor stage (FIG. 6). While B220⁺, CD19⁺ cells developed, they did not progress to the mIg⁺ stage. This is precisely the outcome predicted by results of experiments involving autoreconstitution and adoptive reconstitution using BM HSC from immunologically aged mice (Johnson, S. A., S. J. Rozzo, and J. C. Cambier, Aging-dependent exclusion of antigen-inexperienced cells from the peripheral B cell repertoire. J Immunol, 2002. 168(10): p. 5014-23). In other words, the same developmental arrest is observed when whole bone marrow from immunologically aged mice is used for transplantation.

The inventors have found that this system can be taken a step further, successfully re-establishing LT-HSC lines from bone marrow of adoptive recipients of the original HSC lines (data not shown). This was accomplished simply by culturing bone marrow cells in stem cell cytokines plus tamoxifen to reactivate MYC. These cells are now growing and exhibit the original phenotype.

Example 3

The following example describes a method for reversibly immortalizing HSCs using a method conducted entirely in vitro.

In addition to the method for generating conditionally immortalized long term HSC cell lines described previously herein, the inventors have been able to carry out this procedure completely in vitro. The method described above relies upon introducing the transduced HSC's into mice, and inducing their transformation in vivo. The advantage of carrying this procedure out in vitro is that every aspect of the process is carried out in a controlled environment.

The method first includes the treatment of donor mice with 5-fluorouracil (5-FU) in order to enrich for HSCs and induce these cells to proliferate. 5FU enriched hematopoietic stem cells from the tibia and femurs of mice were collected and then plated in 24 well tissue culture plates in DMEM media containing 15% heat inactivated fetal calf serum and IL-3, IL-6 and SCF, at a density of 1.8-2.0×10⁶ cells per well. The cells were subjected to three rounds of spin infection in order to retrovirally transduce the cells with retroviral vectors encoding MYC-ER and Bcl-2. Briefly, the cells were transfected with pMIG-MYC.ER or pMIT-Bcl2. The virus containing supernatants were collected and supplemented with 4 µg/ml of polybrene and 10 mM HEPES, and passed through a 0.45 µm filter. The two different viral supernatants were mixed at a 1:1 ratio and added to the wells. The cells were then centrifuged at 2000 rpm for one hour. The viral supernatants were replaced at the end of each spin infection. 24 hours after the last round infection, the levels of transduction were determined by flow cytometric analysis in order to determine the transduction efficiency. The transduced cells were then incubated in DMEM medium containing IL-3, IL-6, SCF and 10 nM 4OHT. The medium was replaced every 3 days and special emphasis was placed on ensuring a fresh supply of cytokines and 4OHT. Cells are passed slowly, and as needed.

Using this in vitro approach, the inventors have been able to generate conditionally immortalized cell lines with the following combinations of genes: MYC-ER and Bcl-2; MYC-ER and hTERT (reverse transcriptase component of the human telomerase); ICN-1-ER (ER-regulated active element of the intracellular portion of Notch-1) and Bcl-2; ICN-1-ER and hTERT; and MYC-ER and ICN-1-ER. The data presented in FIGS. 8-11 show the initial characterization of most of these cell lines. They yielded lines composed of c-kit+, Sca-1+, CD34−, flk2− cells, which is a phenotype that is consistent with the one presented by normal long-term hematopoietic stem cells. The data presented in FIGS. 8-11 is derived from the flow cytometric analysis of retrovirally encoded reporter genes (GFP and thy1.1), as well as four markers for stem cells: c-kit, sca-1, CD34 and flk-2. The cell lines shown in FIGS. 8-11 had been in culture for 5 weeks prior to phenotyping. These cells have been expanded and divided in continuous culture for over 35 days to date.

Referring to FIG. 8, this figure shows the phenotypic comparison of cell lines derived from HSCs obtained from young C57/BL6 mice that were retrovirally transduced with BCL-2 and MYC-ER and maintained in continuous in vitro culture for >90 days. Shown is the phenotype of representative clones 3 (young) months after 90 days of continuous of culture.

Referring to FIG. 9, this figure shows the phenotypic comparison of cell lines derived from HSCs obtained from young C57/BL6 mice that were retrovirally transduced with different combinations of oncogenes and maintained in continuous in vitro culture for >90 days. 5FU enriched HSCs were retroviral transduced with pMIG-MYC and pMIT-Bcl-2 (top panels), pMIG-MYC.ER and pMIG-hTERT (middle panels), or pMIG-ICN.1.ER and pMIT-Bcl-2. The cells were maintained in DMEM supplemented with 15% fetal calf serum, and a cocktail of IL-6, IL-3 and SCF. Shown is the phenotype of representative clones 3 (young) months after 90 days of continuous of culture. The panels represent the results of the flow cytometric analysis for expression of the viral expression markers (GFP and Thy1.1), as well as four markers required to define long-term HSCs in mice, Sca-1, c-kit, CD34 and Flk-2. The four cell lines contained subpopulations that retained the phenotypes of lt-HSCs (Sca-1+, c-kit+, CD34−, flk-2−).

Referring to FIG. 10, this figure shows the phenotypic comparison of cell lines derived from HSCs obtained from young C57/BL6 mice that were retrovirally transduced with different combinations of oncogenes and maintained in continuous in vitro culture for >90 days. 5FU enriched HSCs were retroviral transduced with pMIG-ICN.1.ER and pMIT-Bcl-2 (top panels), pMIG-ICN.1 and pMIT-Bcl-2 (second row panels), or pMIG-ICN.1 and pMIG-Bcl-2 (third row panels), or pMIG-hTERT and pMIT-Bcl-2 (bottom panels). The cells were maintained in DMEM supplemented with 15% fetal calf serum, and a cocktail of IL-6, IL-3 and SCF. Shown is the phenotype of representative clones 3 (young) months after 90 days of continuous of culture. The panels represent the results of the flow cytometric analysis for expression of the viral expression markers (GFP and Thy1.1), as well as four markers required to define long-term HSCs in mice, Sca-1, c-kit, CD34 and Flk-2. The four cell lines contained subpopulations that retained the phenotypes of lt-HSCs (Sca-1+, c-kit+, CD34−, flk-2−).

Referring to FIG. 11, this figure shows the phenotypic comparison of cell lines derived from HSCs obtained from young C57/BL6 mice that were retrovirally transduced with different combinations of oncogenes and maintained in continuous in vitro culture for >90 days. 5FU enriched HSCs were retroviral transduced with pMIG-MYC and pMIG-ICN.1 (top panels), pMIG-MYC.ER and pMIG-ICN.1 (middle panels), or pMIG-ICN.1.ER and pMIG-MYC. The cells were maintained in DMEM supplemented with 15% fetal calf serum, and a cocktail of IL-6, IL-3 and SCF. Shown is the phenotype of representative clones 3 (young) months after 90 days of continuous of culture. The panels represent the results of the flow cytometric analysis for expression of the viral expression markers (GFP and Thy1.1), as well as four markers required to define long-term HSCs in mice, Sca-1, c-kit, CD34 and Flk-2. The four cell lines contained subpopulations that retained the phenotypes of lt-HSCs (Sca-1+, c-kit+, CD34−, flk-2−).

These cell lines have also been used to reconstitute cellular compartments in vivo. Referring to FIG. 12, this figures shows the results of in vivo reconstitution of T cell and B cell compartments from cell lines derived from HSCs obtained from young C57/BL6 mice that were retrovirally transduced with different combinations of oncogenes and maintained in continuous in vitro culture for >90 days. Briefly, 5FU enriched HSCs were retroviral transduced with pMIG-ICN.1-ER and pMIG-hTERT (top panels), pMIG-MYC.ER and pMIG-hTERT (middle panels), or pMIG-MYC-ER and pMIT-Bcl-2 (lower panels). The cell lines were maintained in DMEM supplemented with 15% fetal calf serum, and a cocktail of IL-6, IL-3 and SCF. Lethally irradiated young C57/BL6 mice were reconstituted using bone marrow stem cells from Rag2−/− mice and LT-HSC lines generated in vitro. Six weeks later, bone marrow was harvested and stained with a panel of specific lineage markers. The development of mature CD4 and B220 positive/GFP positive cells can readily be observed. Data from four representative mice are presented in this figure. In each group, approximately 30% of the mice retain GFP marker.

Example 4

The following example describes an extension of the method for reversibly immortalizing human cord blood and bone marrow derived HSCs in vitro.

One additional application of this technology is the ability to expand human long-term hematopoietic stem cells in vitro through their conditional immortalization. The inventors have therefore adapted the in vitro method described in the previous examples for human cells with a few changes. First, the retroviruses are packaged preferably with amphotrophic envelopes in order to enable efficient transduction of human cells. In addition, the source of the cells is human cord blood obtained anonymously from the a cord blood bank, following all rules and regulations set forth by the Institutional Review Boards of the inventors' institutions. The resulting cells will express reporter genes that may ultimately be useful for isolating a pure population by high speed cell sorting. The inventors have noticed that many mature cells resulting from the murine lt-HSC cell lines lose expression of the surface markers, potentially due to the methylation of the retroviral genome upon lineage determination and differentiation. The inventors expect to see similar behavior in the human cells, in which case the lt-HSCs and their prevalence in transplant recipients can be monitored by the presence of reporter genes in such cells, in combination with cell surface markers for that population of cells.

Example 5

The following example describes an approach to the sequential excision of the DNA fragments encoding MYC-ER and Bcl-2 from conditionally immortalized HSC cells.

In order to avoid taking the risk of introducing HSCs that harbor transgenes encoding MYC.ER and Bcl-2 into humans and/or mice, these two DNA fragments will be excised using a bacterial recombinase approach. Two different recombinases will be used in order to allow control over which one of the two genes is excised at any one point in time. Two examples of such recombinases are the Cre and Flp recombinases. Briefly, the recognition substrate sequences (RSS's) for one of the recombinases is introduced into the retroviral constructs such that they flank the open reading frame of the oncogene, as well as the reporter gene (GFP or Thy1.1). In this case, the cells are incubated in media containing a Tat-Cre fusion protein. This recombinant protein has been previously described and shown to be able to passively enter cells, and mediate loxP site-dependent recombination of genomic DNA.

This approach will allow the achievement of a number of things in order to enable the generation of many HSCs for differentiation in vitro and in vivo. First, the cells can gradually be weaned from the high levels of proliferative and survival signals they had become accustomed to during the conditional transformation process. Second, the cells can be re-adapted to depend on normal cytokines for their homeostatic functions and differentiation. Third, the sequential loss of reporter expression will allow the definition of the status and degree of deletion of each one of the genes in question. Accordingly, cells that express both reporter genes (GFP and Thy1.1) harbor both sequences (MYC and Bcl-2, respectively), cells that express Thy1.1 but no GFP have successfully deleted the MYC encoding sequences, but still contain Bcl-2 genes, and lastly, cells that do not express either GFP or Thy1.1 have deleted both of those alleles. FIG. 13 represents this approach in a diagram.

In addition, this approach is tested in mice by obtaining 5FU enriched BM-HSCs from a strain of mice in which the expression of a human MYC transgene can be induced by the withdrawal of tetracycline and the presence of a bacterial protein called tTA (tetracycline transactivator protein). The human MYC cDNA was cloned downstream of a tetracycline regulatory transcription element (TRE). The TRE-MYC mice are treated with 5FU and used to harvest BM-HSCs. Those cells are transduced in vitro with retroviruses expressing Bcl-2 and tTA (pMIT-Bcl2 and pMIG-tTA). The cells are cultured in the continuous presence of Doxycycline in order to maintain the MYC transgene silent. Once the cells are analyzed by flow cytometry, they can be used for transplantation back into mice that will not be maintained on a doxycycline containing diet (this is a more stable form of tetracycline is normally used in vivo).

Once the lt-HSC cell lines are generated, the effect of culturing them in the presence of doxycycline in vitro will be examined in parallel with MYC.ER harboring cell lines that will be cultured in the absence of 4OHT. The protein levels of MYC are monitored by western blots and intracellular staining approaches throughout.

Example 6

The following example describes the generation of many hematopoietic lineages in vitro, following the withdrawal of 4OHT from the liquid tissue culture media.

The traditional methods used to determine the potency of an HSC involve the use of semi-solid media (methycellulose) with defined cytokines in order to potentiate the differentiation of HSCs into specific lineages. The inventors were interested in determining the pluripotency of this cell population created using the method of the present invention in vitro. In order to examine this issue, the ABM42 and ABM46 cell lines described herein were maintained in media containing IL-3, IL-6 and SCF, but without 4OHT. In addition to the lineages that the inventors were able to detect in the reconstituted mice (i.e., lymphoid, myeloid and granulocytic), GFP+ cells could also be detected that expressed NK1.1 or ter-119 (FIG. 14). The NK1.1 cells could either be NK-cell, or NK-T cells. The ter-119 expressing cells are of the erythroid lineage. These findings indicate that these cell lines are capable of giving rise to all of the elements of a normal hematopoietic system and that the cells will be useful for generation of large quantities of specific elements to be used for passive therapies. In addition, they will be of great use and importance to study the early events in hematopoiesis and to identify novel therapy for therapeutic intervention in genetic disorders, or complications that arise the normal course of chemotherapy, or even infectious disease.

Example 7

The following example describes a method for high throughput screens of small molecules or biological agents that induce or inhibit differentiation in conditionally transformed long term HSCs.

The following is a general method for screening small molecules or biological agents that induce or inhibit HSC differentiation. Previously, these types of large screens were prohibited by the fact that large numbers of stem cells were unobtainable. With the present inventors current ability to conditionally immortalize long term HSCs, it is now feasible to propose such technologies.

By way of example, one such method is a myeloid differentiation read-out that has been adapted from Schneider, et al. (Schneider, T., and Issekutz, A. C. (1996). Quantitation of eosinophil and neutrophil infiltration into rat lung by basic assays for eosinophil peroxidase and myeloperoxidase. Application in a Brown Norway rat model of allergic pulmonary inflammation. J Immunol Methods 198, 1-14). Briefly, conditionally transformed long term HSCs are plated in 96 well, flat bottom plates at various concentrations of cell numbers (usually $2\times10^4$-$5\times10^4$ cells/well). The screens are carried out either in complete media (DMEM +15% heat inactivated fetal calf serum, 1× penicillin/streptomycin, 1×1-glutamine and 1× non-essential amino acids, supplemented with IL-3, IL-6 and SCF) with added 4OHT in order to maintain the cells in an undifferentiated state, or in the absence of added 4OHT in order to induce differentiation. These conditions have been shown to give rise to Mac-1+ cells, consistent with a myeloid differentiation pattern. Additional cytokines can be added to direct differentiation in specific paths, although this system can also be used to screen for specific functions of a panel of cytokines. In this instance, the complete media will be added without supplementation with IL-3, IL-6 and SCF, but instead with the given cytokines to be tested or used to direct differentiation (e.g., CSF-1, G-CSF, GM-CSF, EPO, TEPO, etc.).

Small molecules, biological agents or positive control substances (e.g., Arsenic $0_3$) are titrated across the 96 well plate and incubated with the ltHSCs for time frames ranging from 24 to 72 hours, or longer, if needed and as determined based on the agents or molecules to be tested. After incubation, the cells are washed with PBS and resuspended in PBS for overnight storage at −80° C. to lyse the cells. The cells are then thawed at room temperature and the plates are centrifuged for 10 min at 3,000 rpm. The supernatant is then transferred to a new 96 well plate and mixed with tetramethybenzidine (TMB) for 40 min. The reaction is stopped with $4NH_2SO_4$ and the O.D. is read at 450 nm. This type of high-throughput assay can be used to test small molecules or biological agents for the ability to induce or block the differentiation of conditionally transformed long term HSCs into a wide variety of cell types. Results of these screens can then further be tested for the ability to induce or inhibit HSC differentiation in vivo. Variations on this assay format will be apparent to those of skill in the art and are encompassed by the present invention.

Example 8

The following example describes the use of the method of the invention to generate cell lines of an intermediate hematopoietic lineage.

The following protocol can be used to induce the development of cell lines representing intermediate stages of hematopoietic lineage development following transplantation of conditionally immortalized lt-HSC cell lines into lethally irradiated mice. First, $10^3$-$10^5$ conditionally transformed lt-HSC cell lines generated according to the method of the invention are transferred into cohorts of lethally irradiated recipient mice. The transplants will also include $10^5$ Rag-$1^{-/-}$ cells as carriers in order to ensure the initial survival of the irradiated mice. The mice are treated with weekly injections of 1 mg tamoxifen, intraperitoneally, in order to immortalize partially differentiated cells derived from the conditionally transformed lt-HSC cell lines. Injections begin either 3 days-1 week after the initial transplant, or 8 weeks after the transplant, once the mice have been fully reconstituted by the conditionally transformed lt-HSC cell lines. Cells are collected from the spleen and bone marrow cells from mice three days after treatment with tamoxifen, or when they show clinical signs associated with leukemias. The cells are cultured in either the standard bone marrow culture conditions with 4-OHT (DMEM, 15% fetal calf serum, pen/strep, L-glut, non essential amino acids, IL-3, IL-6 and SCF), or in the presence of other cytokines and medium used for different hematopoietic cell types. Cell lines are frozen and/or expanded, and cell lines are also single-cell cloned by limiting dilution and defined by PCR amplification of proviral integrations, frozen, and then characterized for surface marker expression by flow cytometry. These types of approaches are used for both murine and human ctlt-HSC cell lines, using either NOD/SCID mice as the recipients, or neonatal Rag-1–/– mice, which will be given intrahepatic injections.

Example 9

The following example describes the use of the method of the invention and the adoption of protocols used to generate mature CD4+ αβ T-cells in vitro to develop cell lines representing intermediate stages of T-cell development.

In this experiment, conditionally immortalized lt-HSC cell lines generated according to the method of the invention are plated in the presence of the normal cytokine cocktail, supplemented with IL-7 and without tamoxifen. Parallel cultures are established on a layer of OP-9 stromal cells that express Jagged, a Notch-1 ligand. Cells are stained for T-cell lineage markers every 48 hours after the cultures are initiated to monitor for signs of T-cell development. The wells that show signs of T-lineage commitment and development are switched to media containing tamoxifen in order to stabilize the phenotype and establish cell lines. The resulting cell lines are expanded, cloned and characterized as described in Example 8. The T-cell lines are specifically stained for individual TCR-Vβ alleles in order to determine their T-cell receptor repertoire usage. Some mature T-cell lines, or cell lines representing progenitor populations, are transplanted into Rag-$1^{-/-}$ mice in order to evaluate their ability to conform to normal tolerance and homeostatic mechanisms in vivo, as well as their ability to further differentiate in vivo, when appropriate. Finally, their ability to respond to antigenic stimulation is evaluated in vitro and in vivo.

Example 10

The following example describes the use of the method of the invention and the adoption of protocols used for the directed differentiation of HSCs into myeloid cell lineages to develop intermediate developmental cell lines and myeloid leukemia models.

In this experiment, conditionally immortalized lt-HSC cell lines generated according to the methods of the present invention are plated in the presence of the normal cytokine cocktail, supplemented with G-CSF and without tamoxifen. Cells are stained for myeloid lineage markers every 48 hours after the cultures are initiated to monitor for signs of myeloid development. The wells that show signs of myeloid lineage commitment and development are switched to media containing tamoxifen in order to stabilize the phenotype and establish cell lines. The resulting cell lines are expanded, cloned and characterized as described in Example 8. Some of the resulting cell lines are transplanted back into mice in order to monitor their ability to repopulate Op/Op mice (mutant mice that naturally lack macrophages). Those cell lines are also transplanted into wild type mice that will be maintained on tamoxifen throughout, in order to determine if these cell lines will also give rise to myeloid leukemias similar to human AML, CML and APL. These novel tumors provide novel models for preclinical therapeutics.

Example 11

The following example describes the generation of Human adult ctlt-HSC cell lines and examination of their pluripotential in vivo using NOD/SCID or RAG$^{-/-}$ xenotransplant models.

In this experiment, CD34+ cells (from mobilized blood or cord blood) are transduced in vitro with retroviral vectors encoding MYC-ER, Bcl-2 and GFP (for later detection of transplanted cells), packaged using amphotrophic envelopes (according to the methods of the present invention). lt-HSC are selected by propagation in vitro in the presence of 4OHT and growth factors, as described above using murine HSCs. Pluripotency of the selected cells is evaluated by transplantation of lt-HSC lines into sublethally irradiated NOD/SCID or NOD/SCID/β-2M$^{-/-}$ or Rag-$1^{-/-}$ or Rag-$2^{-/-}$ mice, followed 6-12 weeks later by analysis of all blood cell lineages by immunofluorescence flow cytometry. More particularly, following the generation of ctlt-HSC cell lines using the method of the present invention, one can use two different and complimentary approaches to examine their pluripotency. In a first approach, varying amounts of clonal ctlt-HSC cell lines are introduced into sublethally irradiated NOD/SCID mice or NOD/SCID/β-2M$^{-/-}$ mice. In this instance, $10^3$-$10^5$ cells derived from a human ctlt-HSC cell lines are transferred intravenously after the mice are subjected to a sublethal irradiation regimen (0.3 Gy). The mice are analyzed for reconstitution at 6-12 weeks after transplantation. Second, $10^3$-$10^5$ cells derived from a human ctlt-HSC cell lines are introduced into the liver of neonatal Rag-$1^{-/-}$ or Rag-$2^{-/-}$ mice by direct injection. Those xenotransplants will also be analyzed for appropriate reconstitution 6-12 weeks after transplantation.

Example 12

The following example describes the use of conditional approaches to abrogate expression of MYC and Bcl-2 from the ctlt-HSCs after transplantation.

In this experiment, viruses (viral vectors) used to transform stem cells are re-engineered to contain two loxP sites flanking the MYC-ER, Bcl-2 and GFP open reading frames (ORFS). When the cells are transplanted, a regulated form of Cre or CRE-TAT fusion protein will be used to delete the oncogene-encoding sequences, thus eliminating risk of insert-driven malignancy in recipients. This approach is first developed in mice, then applied to human lt-HSCs.

In a second approach, lt-HSCs from TRE-MYC mice are used to generate the cell lines with retroviruses that encode Bcl-2 or rtTA. These are transplanted into mice. Mice are fed Doxycycline to abrogate the expression of MYC. One can use lt-HSCs obtained from TRE-MYCxTRE-Bcl-2 bigenic mice that can be transduced with a pMIG-rtTA retrovirus to eliminate MYC and Bcl2 expression.

Example 13

The following example describes the use of HIV-1 Tat protein fusions with MYC and/or Bcl-2 to attain conditional transformation without genetic modification of the lt-HSCs.

MYC-Tat and Bcl-2-Tat fusion proteins are generated and purified using established protocols. The fusion proteins are tested by treatment of cells in which one can easily assay the effects of overexpressed Bcl-2 (e.g., activated T cells, B-cell lymphoma cell lines that are rendered resistant to BCMA-Fc, etc.) or MYC (e.g., anergic B-cells, naïve T-cells, activated T-cells). Combinations of MYC-Tat and Bcl-2-Tat proteins are used to allow propagation of lt-HSCs prior to transplantation. This approach is readily developed and tested in the mouse system, then applied to human.

The entire disclosure of each of U.S. Provisional Patent Application Nos. 60/728,131 and 60/765,993 is incorporated herein by reference.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method of producing a population of conditionally immortalized hematopoietic stem cells, comprising:
    a) introducing into a plurality of hematopoietic stem cells:
        i. an exogenously synthesized first polypeptide comprising: a MYC polypeptide that has MYC activity; and
        ii. an exogenously synthesized second polypeptide comprising: a Bcl-2 polypeptide;
    so as to produce at least one conditionally immortalized hematopoietic stem cell;
    b) culturing the plurality of hematopoietic stem cells in media comprising at least one of: IL-3, IL-6, stem cell factor, thrombopoietin, Flt3 ligand, or a combination thereof such that a population of conditionally immortalized hematopoietic stem cells is produced,
    and wherein the first polypeptide, the second polypeptide, or both the first and second polypeptides comprise a TAT sequence.

2. The method of claim 1, further comprising (c) removing the first polypeptide such that the population of the stem cells differentiate.

3. The method of claim 1, further comprising (c) removing the first polypeptide such that the population of the stem cells differentiate and, culturing the population of stem cells in the presence of at least one cytokine that directs differentiation towards a specific cell type.

4. The method of claim 1, wherein the Myc polypeptide is a c-MYC polypeptide, a n-MYC polypeptide, a s-MYC polypeptide, or a l-MYC polypeptide.

5. The method of claim 1, wherein the first polypeptide further comprises the hormone-binding domain of the human estrogen receptor.

6. The method of claim 5, further comprising expanding the population of conditionally immortalized stem cells by contacting the plurality of stem cells with: estradiol (E2), 4-hydroxytamoxifen (4-0HT), or both.

7. The method of claim 1, wherein the plurality of stem cells are isolated from umbilical cord blood, bone marrow, or a combination thereof.

8. The method of claim 1, further comprising modifying one or more genes of the plurality of stem cells.

9. A method of producing a population of conditionally immortalized hematopoietic stem cells, comprising:
    a) introducing into a plurality of hematopoietic stem cells:
        i. an exogenously synthesized first polypeptide comprising: a MYC polypeptide that has MYC activity; and
        ii. an exogenously synthesized second polypeptide comprising: a Bcl-2 polypeptide;
    so as to produce at least one conditionally immortalized hematopoietic stem cell;
    b) culturing the plurality of hematopoietic stem cells in media such that a population of conditionally immortalized hematopoietic stem cells is produced,
    and wherein the first polypeptide, the second polypeptide, or both the first and second polypeptides comprise a TAT sequence.

* * * * *

SEQUENCE LISTING

<160> NUMBER OF SEQ ID NOS: 14

<210> SEQ ID NO 1
<211> LENGTH: 2377
<212> TYPE: DNA
<213> ORGANISM: Homo sapiens

<400> SEQUENCE: 1

```
accccgagc tgtgctgctc gcggccgcca ccgccgggcc ccggccgtcc ctggctcccc      60
tcctgcctcg agaagggcag ggcttctcag aggcttggcg ggaaaaagaa cggagggagg    120
gatcgcgctg agtataaaag ccggttttcg gggctttatc taactcgctg tagtaattcc    180
agcgagaggc agagggagcg agcgggcggc cggctagggt ggaagagccg ggcgagcaga    240
gctgcgctgc gggcgtcctg ggaagggaga tccggagcga atagggggct tcgcctctgg    300
cccagccctc ccgctgatcc cccagccagc ggtccgcaac ccttgccgca tccacgaaac    360
tttgcccata gcagcgggcg ggcactttgc actggaactt acaacacccg agcaaggacg    420
cgactctccc gacgcgggga ggctattctg cccatttggg gacacttccc cgccgctgcc    480
aggacccgct tctctgaaag gctctccttg cagctgctta gacgctggat ttttttcggg    540
tagtggaaaa ccagcagcct cccgcgacga tgcccctcaa cgttagcttc accaacagga    600
actatgacct cgactacgac tcggtgcagc cgtatttcta ctgcgacgag gaggagaact    660
tctaccagca gcagcagcag agcgagctgc agccccggc gccagcgag gatatctgga     720 agaaattcga gctgctgccc accccgcccc tgtccctag ccgccgctcc gggctctgct    780
cgccctccta cgttgcggtc acaccttct ccttcgggg agacaacgac ggcggtggcg     840
ggagcttctc cacggccgac cagctggaga tggtgaccga gctgctggga ggagacatgg    900
tgaaccagag tttcatctgc gacccggacg acgagacctt catcaaaaac atcatcatcc    960
aggactgtat gtggagcggc ttctcggccg ccgccaagct cgtctcagag aagctggcct   1020 cctaccagc tgcgcgcaaa gacagcggca gcccgaaccc cgcccgcggc cacagcgtct   1080
gctccacctc cagcttgtac ctgcaggatc tgagcgccgc cgcctcagag tgcatcgacc   1140
cctcggtggt cttcccctac cctctcaacg acagcagctc gcccaagtcc tgcgcctcgc   1200
aagactccag cgccttctct ccgtcctcgg attctctgct ctcctcgacg gagtcctccc   1260
cgcagggcag ccccgagccc ctggtgctcc atgaggagac accgccacc accagcagcg   1320 actctgagga ggaacaagaa gatgaggaag aaatcgatgt tgtttctgtg gaaaagaggc   1380
aggctcctgg caaaaggtca gagtctggat caccttctgc tggaggccac agcaaacctc   1440
```

-continued

```
ctcacagccc actggtcctc aagaggtgcc acgtctccac acatcagcac aactacgcag   1500
cgcctccctc cactcggaag gactatcctg ctgccaagag ggtcaagttg gacagtgtca   1560
gagtcctgag acagatcagc aacaaccgaa aatgcaccag ccccaggtcc tcggacaccg   1620
aggagaatgt caagaggcga acacacaacg tcttggagcg ccagaggagg aacgagctaa   1680
aacggagctt ttttgccctg cgtgaccaga tcccggagtt ggaaaacaat gaaaaggccc   1740
ccaaggtagt tatccttaaa aaagccacag catacatcct gtccgtccaa gcagaggagc   1800
aaaagctcat ttctgaagag gacttgttgc ggaaacgacg agaacagttg aaacacaaac   1860
ttgaacagct acggaactct tgtgcgtaag gaaaagtaag gaaaacgatt ccttctaaca   1920
gaaatgtcct gagcaatcac ctatgaactt gtttcaaatg catgatcaaa tgcaacctca   1980
caaccttggc tgagtcttga gactgaaaga tttagccata atgtaaactg cctcaaattg   2040
gactttgggc ataaaagaac ttttttatgc ttaccatctt ttttttttct ttaacagatt   2100
tgtatttaag aattgttttt aaaaaatttt aagatttaca caatgtttct ctgtaaatat   2160
tgccattaaa tgtaaataac tttaataaaa cgtttatagc agttacacag aatttcaatc   2220
ctagtatata gtacctagta ttataggtac tataaaccct aatttttttt atttaagtac   2280
attttgcttt ttaaagttga ttttttttcta ttgtttttag aaaaaataaa ataactggca   2340
aatatatcat tgagccaaaa aaaaaaaaaa aaaaaaa                            2377
```

```
<210> SEQ ID NO 2
<211> LENGTH: 454
<212> TYPE: PRT
<213> ORGANISM: Homo sapiens

<400> SEQUENCE: 2

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
            20                  25                  30

Ser Val Gln Pro Tyr Phe Tyr Cys Asp Glu Glu Glu Asn Phe Tyr Gln
        35                  40                  45

Gln Gln Gln Gln Ser Glu Leu Gln Pro Pro Ala Pro Ser Glu Asp Ile
    50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
            100                 105                 110

Gln Leu Glu Met Val Thr Glu Leu Leu Gly Gly Asp Met Val Asn Gln
        115                 120                 125

Ser Phe Ile Cys Asp Pro Asp Asp Glu Thr Phe Ile Lys Asn Ile Ile
    130                 135                 140

Ile Gln Asp Cys Met Trp Ser Gly Phe Ser Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ala Ser Glu Cys Ile Asp Pro Ser Val
        195                 200                 205
```

Val Phe Pro Tyr Pro Leu Asn Asp Ser Ser Pro Lys Ser Cys Ala
    210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Gln Glu
            260                 265                 270

Asp Glu Glu Glu Ile Asp Val Val Ser Val Glu Lys Arg Gln Ala Pro
            275                 280                 285

Gly Lys Arg Ser Glu Ser Gly Ser Pro Ser Ala Gly Gly His Ser Lys
    290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
    355                 360                 365

Val Lys Arg Arg Thr His Asn Val Leu Glu Arg Gln Arg Arg Asn Glu
370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
            420                 425                 430

Asp Leu Leu Arg Lys Arg Arg Glu Gln Leu Lys His Lys Leu Glu Gln
    435                 440                 445

Leu Arg Asn Ser Cys Ala
    450

<210> SEQ ID NO 3
<211> LENGTH: 51552
<212> TYPE: DNA
<213> ORGANISM: Homo sapiens
<220> FEATURE:
<221> NAME/KEY: modified_base
<222> LOCATION: (31450)..(31450)
<223> OTHER INFORMATION: a, c, g or t

<400> SEQUENCE: 3

```
acttgagccc aagagttcaa ggctacggtg agccatgatt gcaacaccac acgccagcct      60
tggtgacaga atgagaccct gtctcaaaaa aaaaaaaaaa aattgaaata atataaagca     120
tcttctctgg ccacagtgga acaaaaccag aaatcaacaa caagaggaat tttgaaaact     180
atacaaacac atgaaaatta aacaatatac ttctgaatga ccagtgagtc aatgaagaaa     240
ttaaaaagga aattgaaaaa tttatttaag caaatgataa cggaaacata acctctcaaa     300
acccacggta tacagcaaaa gcagtgctaa gaaggaagtt tatagctata agcagctaca     360
tcaaaaaagt agaaaagcca ggcgcagtgg ctcatgcctg taatcccagc actttgggag     420
gccaaggcgg gcagatcgcc tgaggtcagg agttcgagac cagcctgacc aacacagaga     480
aaccttgtcg ctactaaaaa tacaaaatta gctgggcatg gtggcacatg cctgtaatcc     540
cagctactcg ggaggctgag gcaggataac cgcttgaacc caggaggtgg aggttgcggt     600
```

```
gagccgggat tgcgccattg gactccagcc tgggtaacaa gagtgaaacc ctgtctcaag      660
aaaaaaaaaa aagtagaaaa acttaaaaat acaacctaat gatgcacctt aaagaactag      720
aaaagcaaga gcaaactaaa cctaaaattg gtaaaagaaa agaaataata aagatcagag      780
cagaaataaa tgaaactgaa agataacaat acaaagatc  aacaaaatta aaagttggtt      840
ttttgaaaag ataaacaaaa ttgacaaacc tttgcccaga ctaagaaaaa aggaagaag       900 acctaaataa ataaagtcag agatgaaaaa agagacatta caactgatac cacagaaatt      960
caaaggatca ctagaggcta ctatgagcaa ctgtacacta ataaattgaa aaacctagaa     1020
aaaatagata aattcctaga tgcatacaac ctaccaagat tgaaccatga agaaatccaa     1080
agcccaaaca gaccaataac aataatggga ttaaagccat aataaaaagt ctcctagcaa     1140
agagaagccc aggacccaat ggcttccctg ctggattta  ccaatcattt aaagaagaat     1200
gaattccaat cctactcaaa ctattctgaa aaatagagga agaatactt  ccaaactcat     1260 tctacatggc cagtattacc ctgattccaa aaccagacaa aaacacatca aaacaaaca      1320 aacaaaaaaa cagaaagaaa gaaaactaca ggccaatatc cctgatgaat actgatacaa     1380
aaatcctcaa caaaacacta gcaaaccaaa ttaaacaaca ccttcgaaag atcattcatt     1440
gtgatcaagt gggatttatt ccagggatgg aaggatggtt caacatatgc aaatcaatca     1500
atgtgataca tcatcccaac aaaatgaagt acaaaaacta tatgattatt tcactttatg     1560
cagaaaaagc atttgataaa attctgcacc cttcatgata aaaccctca  aaaaaccagg     1620 tatacaagaa acatacaggc caggcacagt ggctcacacc tgcgatccca gcactctggg     1680
aggccaaggt gggatgattg cttgggccca ggagtttgag actagcctgg gcaacaaaat     1740
gagacctggt ctacaaaaaa cttttttaaa aaattagcca ggcatgatgg catatgcctg     1800
tagtcccagc tagtctggag gctgaggtgg gagaatcact taagcctagg aggtcgaggc     1860
tgcagtgagc catgaacatg tcactgtact ccagcctaga caacagaaca agaccccact     1920
gaataagaag aaggagaagg agaagggaga agggagggag aagggaggag gaggagaagg     1980
aggaggtgga ggagaagtgg aaggggaagg ggaagggaaa gaggaagaag aagaaacata     2040
tttcaacata ataaaagccc tatatgacag accgaggtag tattatgagg aaaaactgaa     2100
agcctttcct ctaagatctg gaaaatgaca agggcccact ttcaccactg tgattcaaca     2160
tagtactaga agtcctagct agagcaatca gataagagaa agaaataaaa ggcatccaaa     2220
ctggaaagga agaagtcaaa ttatcctgtt tgcagatgat atgatcttat atctggaaaa     2280
gacttaagac accactaaaa aactattaga gctgaaattt ggtacagcag gatacaaaat     2340
caatgtacaa aaatcagtag tatttctata ttccaacagc aaacaatctg aaaaagaaac     2400
caaaaaagca gctacaaata aaattaaaca gctaggaatt aaccaaagaa gtgaaagatc     2460
tctacaatga aaactataaa atgttgataa agaaattga  agagggcaca aaaaaagaaa     2520
agatattcca tgttcataga ttggaagaat aaatactgtt aaaatgtcca tactacccaa     2580
agcaatttac aaattcaatg caatccctat taaaatacta atgacgttct tcacagaaat     2640
agaagaaaca attctaagat ttgtacagaa ccacaaaaga cccagaatag ccaaagctat     2700
cctgaccaaa agaacaaaaa ctggaagcat acattacct  gacttcaaat tatactacaa     2760
agctatagta acccaaacta catggtactg gcataaaaac agatgagaca tggaccagag     2820
gaacagaata gagaatccag aaacaaatcc atgcatctac agtgaactca ttttgacaa      2880 aggtgccaag aacatacttt ggggaaaaga taatctcttc aataaatggt gctggaggaa     2940
```

```
ctggatatcc atatgcaaaa taacaatact agaactctgt ctctcaccat atacaaaagc    3000
aaatcaaaat ggatgaaagg cttaaatcta aaacctcaaa ctttgcaact actaaaagaa    3060
aacaccggag aaactctcca ggacattgga gtgggcaaag acttcttgag taattccctg    3120
caggcacagg caaccaaagc aaaaacagac aaatgggatc atatcaagtt aaaaagcttc    3180
tgcccagcaa aggaaacaat caacaaagag aagagacaac ccacagaatg ggagaatata    3240
tttgcaaact attcatctaa caaggaatta ataaccagta tatataagga gctcaaacta    3300
ctctataaga aaacacccta ataagctgat tttcaaaaat aagcaaaaga tctgggtaga    3360
catttctcaa ataagtcat acaaatggca acaggcatc tgaaaatgtg ctcaacacca     3420
ctgatcatca gagaaatgca aatcaaaact actatgagag atcatctcat cccagttaaa    3480
atggctttta ttcaaaagac aggcaataac aaatgccagt gaggatgtgg ataaaaggaa    3540
acccttggac actgttggtg ggaatggaaa ttgctaccac tatggagaac agtttgaaag    3600
ttcctcaaaa aactaaaaat aaagctacca tacagcaatc ccattgctag gtatatactc    3660 caaaaaggg aatcagtgta tcaacaagct atctccactc ccacatttac tgcagcactg     3720
ttcatagcag ccaaggtttg gaagcaacct cagtgtccat caacagacga atggaaaaag    3780
aaaatgtggt gcacatacac aatggagtac tacgcagcca taaaaagaa tgagatcctg     3840 tcagttgcaa cagcatgggg ggcactggtc agtatgttaa gtgaaataag ccaggcacag    3900
aaagacaaac ttttcatgtt ctcccttact tgtgggagca aaaattaaaa caattgacat    3960
agaaatagag gagaatggtg gttctagagg ggtgggggac agggtgacta gagtcaacaa    4020
taatttattg tatgttttaa ataactaaa agagtataat tgggttgttt gtaacacaaa     4080
gaaaggataa atgcttgaag gtgacagata ccccatttac cctgatgtga ttattacaca    4140
ttgtatgcct gtatcaaaat atctcatgta tgctatagat ataaacccta ctatattaaa    4200
aattaaaatt ttaatggcca ggcacggtgg ctcatgtccg taatcccagc actttgggag    4260
gccgaggcgg gtggatcacc tgaggtcagg agtttgaaac cagtctggcc accatgatga    4320
aaccctgtct ctactaaaga tacaaaaatt agccaggcgt ggtggcacat acctgtagtc    4380
ccaactactc aggaggctga gacaggagaa ttgcttgaac ctgggaggcg gaggttgcag    4440
tgagccgaga tcatgccact gcactgcagc ctgggtgaca gagcaagact ccatctcaaa    4500
acaaaaacaa aaaaagaag attaaaattg taattttat gtaccgtata aatatatact      4560
ctactatatt agaagttaaa aattaaaaca attataaaag gtaattaacc acttaatcta    4620
aaataagaac aatgtatgtg gggtttctag cttctgaaga agtaaaagtt atggccacga    4680
tggcagaaat gtgaggaggg aacagtggaa gttactgttg ttagacgctc atactctctg    4740
taagtgactt aattttaacc aaagacaggc tgggagaagt taaagaggca ttctataagc    4800
cctaaaacaa ctgctaataa tggtgaaagg taatctctat taattaccaa taattacaga    4860
tatctctaaa atcgagctgc agaattgca cgtctgatca caccgtcctc tcattcacgg     4920 tgctttttt cttgtgtgct tggagatttt cgattgtgtg ttcgtgtttg gttaaactta     4980
atctgtatga atcctgaaac gaaaatggt ggtgatttcc tccagaagaa ttagagtacc     5040
tggcaggaag caggtggctc tgtggacctg agccacttca atcttcaagg gtctctggcc    5100
aagacccagg tgcaaggcag aggcctgatg acccgaggac aggaaagctc ggatgggaag    5160
gggcgatgag aagcctgcct cgttggtgag cagcgcatga agtgccctta tttacgcttt    5220
gcaaagattg ctctgatac catctggaaa aggcggccag cggaatgca aggagtcaga     5280 agcctcctgc tcaaacccag gccagcagct atggcgccca cccgggcgtg tgccagaggg    5340
```

```
agaggagtca aggcacctcg aagtatggct taaatctttt tttcacctga agcagtgacc   5400
aaggtgtatt ctgagggaag cttgagttag gtgccttctt taaaacagaa agtcatggaa   5460
gcacccttct caagggaaaa ccagacgccc gctctgcggt catttacctc tttcctctct   5520
ccctctcttg ccctcgcggt ttctgatcgg gacagagtga cccccgtgga gcttctccga   5580
gcccgtgctg aggaccctct tgcaagggc tccacagacc cccgccctgg agaggagt   5640 ctgagcctgg cttaataaca aactgggatg tggctggggg cggacagcga cggcgggatt   5700
caaagactta attccatgag taaattcaac cttttccacat ccgaatggat ttggatttta   5760
tcttaatatt ttcttaaatt tcatcaaata acattcagga ctgcagaaat ccaaaggcgt   5820
aaaacaggaa ctgagctatg tttgccaagg tccaaggact taataaccat gttcagaggg   5880
atttttcgcc ctaagtactt tttattggtt ttcataaggt ggcttagggt gcaagggaaa   5940
gtacacgagg agaggcctgg gcggcagggc tatgagcacg gcagggccac cggggagaga   6000
gtccccggcc tgggaggctg acagcaggac cactgaccgt cctccctggg agctgccaca   6060
ttgggcaacg cgaaggcggc cacgctgcgt gtgactcagg accccatacc ggcttcctgg   6120
gcccacccac actaacccag gaagtcacgg agctctgaac ccgtggaaac gaacatgacc   6180
cttgcctgcc tgcttccctg ggtgggtcaa gggtaatgaa gtggtgtgca ggaaatggcc   6240
atgtaaatta cacgactctg ctgatgggga ccgttccttc catcattatt catcttcacc   6300
cccaaggact gaatgattcc agcaacttct tcgggtgtga caagccatga caaaactcag   6360
tacaaacacc actcttttac taggcccaca gagcacggsc cacacccctg atatattaag   6420
agtccaggag agatgaggct gctttcagcc accaggctgg ggtgacaaca gcggctgaac   6480
agtctgttcc tctagactag tagaccctgg caggcactcc cccagattct agggcctggt   6540
tgctgcttcc cgagggcgcc atctgccctg gagactcagc ctggggtgcc acactgaggc   6600
cagccctgtc tccacaccct ccgcctccag gcctcagctt ctccagcagc ttcctaaacc   6660
ctgggtgggc cgtgttccag cgctactgtc tcacctgtcc cactgtgtct tgtctcagcg   6720
acgtagctcg cacggttcct cctcacatgg ggtgtctgtc tccttcccca acactcacat   6780
gcgttgaagg gaggagattc tgcgcctccc agactggctc ctctgagcct gaacctggct   6840
cgtggccccc gatgcaggtt cctggcgtcc ggctgcacgc tgacctccat ttccaggcgc   6900
tccccgtctc ctgtcatctg ccggggcctg ccggtgtgtt cttctgtttc tgtgctcctt   6960
tccacgtcca gctgcgtgtg tctctgcccg ctagggtctc ggggttttta taggcatagg   7020
acgggggcgt ggtgggccag ggcgctcttg ggaaatgcaa catttgggtg tgaaagtagg   7080
agtgcctgtc ctcacctagg tccacgggca caggcctggg gatggagccc cgccaggga   7140 cccgcccttc tctgcccagc actttcctgc cccctccct ctggaacaca gagtggcagt   7200
ttccacaagc actaagcatc ctcttcccaa aagacccagc attggcaccc ctggacattt   7260
gccccacagc cctgggaatt cacgtgacta cgcacatcat gtacacactc ccgtccacga   7320 ccgaccccg ctgttttatt taatagcta caaagcaggg aaatccctgc taaaatgtcc   7380
tttaacaaac tggttaaaca aacgggtcca tccgcacggt ggacagttcc tcacagtgaa   7440
gaggaacatg ccgtttataa agcctgcagg catctcaagg gaattacgct gagtcaaaac   7500
tgccacctcc atgggatacg tacgcaacat gctcaaaaag aaagaatttc accccatggc   7560
aggggagtgg ttaggggggt taaggacggt ggggcggca gctgggggct actgcacgca   7620
ccttttacta aagccagttt cctggttctg atggtattgg ctcagttatg ggagactaac   7680
```

```
catagggag tgggatggg ggaacccgga ggctgtgcca tctttgccat gcccgagtgt    7740
cctgggcagg ataatgctct agagatgccc acgtcctgat tcccccaaac ctgtggacag    7800
aacccgcccg gccccagggc ctttgcaggt gtgatctccg tgaggaccct gaggtctggg    7860
atccttcggg actacctgca ggcccgaaaa gtaatccagg ggttctggga agaggcgggc    7920
aggagggtca gagggggca gcctcaggac gatggaggca gtcagtctga ggctgaaaag    7980
ggagggaggg cctcgagccc aggcctgcaa gcgcctccag aagctggaaa aagcggggaa    8040
gggaccctcc acggagcctg cagcaggaag gcacggctgg cccttagccc accagggccc    8100
atcgtggacc tccggcctcc gtgccatagg agggcactcg cgctgccctt ctagcatgaa    8160
gtgtgtgggg atttgcagaa gcaacaggaa acccatgcac tgtgaatcta ggattatttc    8220
aaaacaaagg tttacagaaa catccaagga cagggctgaa gtgcctccgg gcaagggcag    8280
ggcaggcacg agtgatttta tttagctatt ttatttattt tacttacttt ctgagacaga    8340
gttatgctct tgttgcccag gctggagtgc agcggcatga tcttggctca ctgcaacctc    8400
cgtctcctgg gttcaagcaa ttctcgtgcc tcagcctccc aagtagctgg gatttcaggc    8460
gtgcaccacc acacccggct aattttgtat tttagtagag atgggctttt caccatgttg    8520
gtcaagctga tctcaaaatc ctgacctcag gtgatccgcc cacctcagcc tcccaaagtg    8580
ctgggattac aggcatgagc cactgcacct ggcctattta accattttaa aacttccctg    8640
ggctcaagtc acacccactg gtaaggagtt catggagttc aatttcccct ttactcagga    8700
gttaccctcc tttgatattt tctgtaattc ttcgtagact ggggatacac cgtctcttga    8760
catattcaca gtttctgtga ccacctgtta tcccatggga cccactgcag gggcagctgg    8820
gaggctgcag gcttcaggtc ccagtggggt tgccatctgc cagtagaaac ctgatgtaga    8880
atcagggcgc aagtgtggac actgtcctga atctcaatgt ctcagtgtgt gctgaaacat    8940
gtagaaatta aagtccatcc ctcctactct actgggattg agccccttcc ctatcccccc    9000
ccaggggcag aggagttcct ctcactcctg tggaggaagg aatgatactt tgttattttt    9060
cactgctggt actgaatcca ctgtttcatt tgttggtttg tttgttttgt tttgagaggc    9120
ggtttcactc ttgttgctca ggctggaggg agtgcaatgg cgcgatcttg gcttactgca    9180
gcctctgcct cccaggttca agtgattctc ctgcttccgc ctcccatttg gctgggatta    9240
caggcacccg ccaccatgcc cagctaattt tttgtatttt tagtagagac ggggtgggt    9300 ggggttcacc atgttggcca ggctggtctc gaacttctga cctcagatga tccacctgcc    9360
tctgcctcct aaagtgctgg gattacaggt gtgagccacc atgcccagct cagaatttac    9420
tctgtttaga aacatctggg tctgaggtag gaagctcacc ccactcaagt gttgtggtgt    9480
tttaagccaa tgatagaatt tttttattgt tgttagaaca ctcttgatgt tttacactgt    9540
gatgactaag acatcatcag cttttcaaag acacactaac tgcacccata atactggggt    9600
gtcttctggg tatcagcaat cttcattgaa tgccggagg cgtttcctcg ccatgcacat    9660
ggtgttaatt actccagcat aatcttctgc ttccatttct tctcttccct cttttaaaat    9720
tgtgttttct atgttggctt ctctgcagag aaccagtgta agctacaact taacttttgt    9780
tggaacaaat tttccaaacc gcccctttgc cctagtggca gagacaattc acaaacacag    9840
ccctttaaaa aggcttaggg atcactaagg ggatttctag aagagcgacc tgtaatccta    9900
agtatttaca agacgaggct aacctccagc gagcgtgaca gcccagggag ggtgcgaggc    9960
ctgttcaaat gctagctcca taaataaagc aattcctcc ggcagtttct gaaagtagga    10020
aaggttacat ttaaggttgc gtttgttagc atttcagtgt ttgccgacct cagctacagc    10080
```

```
atccctgcaa ggcctcggga gacccagaag tttctcgccc ccttagatcc aaacttgagc    10140
aacccggagt ctggattcct gggaagtcct cagctgtcct gcggttgtgc cggggcccca    10200
ggtctggagg ggaccagtgg ccgtgtggct tctactgctg ggctggaagt cgggcctcct    10260
agctctgcag tccgaggctt ggagccaggt gcctggaccc cgaggctgcc ctccaccctg    10320
tgcgggcggg atgtgaccag atgttggcct catctgccag acagagtgcc ggggcccagg    10380
gtcaaggccg ttgtggctgg tgtgaggcgc ccggtgcgcg ccagcagga gcgcctggct    10440
ccatttccca cccttctcg acgggaccgc cccgtgggt gattaacaga tttggggtgg    10500
tttgctcatg gtggggaccc ctcgccgcct gagaacctgc aaagagaaat gacgggcctg    10560
tgtcaaggag cccaagtcgc ggggaagtgt tgcagggagg cactccggga ggtcccgcgt    10620
gcccgtccag ggagcaatgc gtcctcgggt tcgtccccag ccgcgtctac gcgcctccgt    10680
cctcccttc acgtccggca ttcgtggtgc ccggagcccg acgccccgcg tccggacctg    10740
gaggcagccc tgggtctccg gatcaggcca gcggccaaag ggtcgccgca cgcacctgtt    10800
cccagggcct ccacatcatg gcccctccct cgggttaccc cacagcctag gccgattcga    10860
cctctctccg ctggggccct cgctggcgtc cctgcaccct gggagcgcga gcggcgcgcg    10920
ggcggggaag cgcggcccag accccgggt ccgcccggag cagctgcgct gtcggggcca    10980
ggccgggctc ccagtggatt cgcgggcaca gacgcccagg accgcgctcc ccacgtggcg    11040
gagggactgg ggacccgggc accgtcctg ccccttcacc ttccagctcc gcctcctccg    11100
cgcggacccc gccccgtccc gacccctccc gggtccccgg cccagccccc tccgggccct    11160
cccagcccct cccttccttt tccgcggccc cgccctctcc tcgcggcgcg agtttcaggc    11220
agcgctgcgt cctgctgcgc acgtgggaag ccctggcccc ggccaccccc gcgatgccgc    11280
gcgctccccg ctgccgagcc gtgcgctccc tgctgcgcag ccactaccgc gaggtgctgc    11340
cgctggccac gttcgtgcgg cgcctggggc cccaggctg gcggctggtg cagcgcgggg    11400
acccggcggc tttccgcgcg ctggtggccc agtgcctggt gtgcgtgccc tgggacgcac    11460
ggccgccccc cgccgccccc tccttccgcc aggtgggcct ccccggggtc ggcgtccggc    11520
tggggttgag ggcggccggg gggaaccagc gacatgcgga gagcagcgca ggcgactcag    11580
ggcgcttccc ccgcaggtgt cctgcctgaa ggagctggtg gcccgagtgc tgcagaggct    11640
gtgcgagcgc ggcgcgaaga acgtgctggc cttcggcttc gcgctgctgg acggggcccg    11700
cgggggcccc cccgaggcct tcaccaccag cgtgcgcagc tacctgccca acacggtgac    11760
cgacgcactg cggggagcg gggcgtgggg gctgctgctg cgccgcgtgg gcgacgcgt    11820
gctggttcac ctgctggcac gctgcgcgct ctttgtgctg gtggctccca gctgcgccta    11880
ccaggtgtgc gggccgccgc tgtaccagct cggcgctgcc actcaggccc ggcccccgcc    11940
acacgctagt ggaccccgaa ggcgtctggg atgcgaacgg gcctggaacc atagcgtcag    12000
ggaggccggg gtcccctgg gcctgccagc cccgggtgcg aggaggcgcg ggggcagtgc    12060
cagccgaagt ctgccgttgc ccaagaggcc caggcgtggc gctgcccctg agccggagcg    12120
gacgcccgtt gggcagggt cctgggccca cccgggcagg acgcgtggac cgagtgaccg    12180
tggtttctgt gtggtgtcac ctgccagacc cgccgaagaa gccacctctt tggagggtgc    12240
gctctctggc acgcgccact cccacccatc cgtgggccgc cagcaccacg caggccccc    12300
atccacatcg cggccaccac gtccctggga cacgccttgt cccccggtgt acgccgagac    12360
caagcacttc ctctactcct caggcgacaa ggagcagctg cggccctcct tcctactcag    12420
```

```
ctctctgagg cccagcctga ctggcgctcg gaggctcgtg gagaccatct ttctgggttc    12480
caggccctgg atgccaggga ctccccgcag gttgccccgc ctgccccagc gctactggca    12540
aatgcggccc ctgtttctgg agctgcttgg gaaccacgcg cagtgcccct acgggtgct    12600 cctcaagacg cactgcccgc tgcgagctgc ggtcacccca gcagccggtg tctgtgcccg    12660
ggagaagccc cagggctctg tggcggcccc cgaggaggag gacacagacc ccgtcgcct    12720 ggtgcagctg ctccgccagc acagcagccc ctggcaggtg tacggcttcg tgcgggcctg    12780
cctgcgccgg ctggtgcccc caggcctctg ggctccagg cacaacgaac gccgcttcct    12840
caggaacacc aagaagttca tctccctggg gaagcatgcc aagctctcgc tgcaggagct    12900
gacgtggaag atgagcgtgc gggactgcgc ttggctgcgc aggagcccag gtgaggaggt    12960
ggtggccgtc gagggcccag gccccagagc tgaatgcagt aggggctcag aaaagggggc    13020
aggcagagcc ctggtcctcc tgtctccatc gtcacgtggg cacacgtggc ttttcgctca    13080
ggacgtcgag tggacacggt gatctctgcc tctgctctcc ctcctgtcca gtttgcataa    13140
acttacgagg ttcaccttca cgttttgatg gacacgcggt ttccaggcgc cgaggccaga    13200
gcagtgaaca gaggaggctg ggcgcggcag tggagcccgg ttgccggcaa tggggagaag    13260
tgtctggaag cacagacgct ctggcgaggg tgcctgcagg ttacctataa tcctcttcgc    13320
aatttcaagg gtgggaatga gaggtgggga cgagaacccc ctcttcctgg gggtgggagg    13380
taagggtttt gcaggtgcac gtggtcagcc aatatgcagg tttgtgttta agatttaatt    13440
gtgtgttgac ggccaggtgc ggtggctcac gccggtaatc ccagcacttt gggaagctga    13500
ggcaggtgga tcacctgagg tcaggagttt gagaccagcc tgaccaacat ggtgaaaccc    13560
tatctgtact aaaaatacaa aaattagctg ggcatggtgg tgtgtgcctg taatcccagc    13620
tacttgggag gctgaggcag gagaatcact tgaacccagg aggcggaggc tgcagtgagc    13680
tgagattgtg ccattgtact ccagcctggg cgacaagagt gaaactctgt ctttaaaaaa    13740
aaaaagtgtt cgttgattgt gccaggacag ggtagaggga gggagataag actgttctcc    13800
agcacagatc ctggtcccat ctttaggtat gaagagggcc acatgggagc agaggacagc    13860
agatggctcc acctgctgag gaagggacag tgtttgtggg tgttcagggg atggtgctgc    13920
tgggccctgc cgtgtcccca ccctgttttt ctggatttga tgttgaggaa cctccgctcc    13980 agccccttt tggctcccag tgctcccagg ccctaccgtg gcagctagaa gaagtcccga    14040 tttcacccc tccccacaaa ctcccaagac atgtaagact tccggccatg cagacaagga    14100
gggtgacctt cttggggctc ttttttttct tttttctttt ttatggtggc aaaagtcata    14160
taacatgaga ttggcactcc taacaccgtt ttctgtgtac agtgcagaat tgctaactcg    14220
gcggtgttta cagcaggttg cttgaaatgc tgcgtcttgc gtgactggaa gtccctaccc    14280
atcgaacggc agctgcctca cacctgctgc ggctcaggtg gaccacgccg agtcagataa    14340
gcgtcatgca acccagtttt gcttttttgtg ctccagcttc cttcgttgag gagagtttga    14400
gttctctgat caggactctg cctgtcattg ctgttctctg acttcagatg aggtcacaat    14460
ctgcccctgg cttatgcagg gagtgaggcg tggtccccgg gtgtccctgt cacgtgcagg    14520
gtgagtgagg cgttgccccc aggtgtccct gtcacgtgta gggtgagtga ggcgcggccc    14580
ccgggtgtcc ctgtcccgtg cagcgtgatt gaggtgtggc cccgggtgt ccctgtcacg    14640 tgtagggtga gtgaggcgcc atccccgggt gtcctgtca cgtgtagggt gagtgaggcg    14700
tggtccccgg gtgtccctgt cccgtgcagg gtgagtgagg cactgtcccc gggtgtccct    14760
gtcacgtgca gggtgagtga ggcgcggtcc ccgggtgtcc ctctcaggtg tagggtgagt    14820
```

```
gaggcgcggc cccagggtgt ccctgtcacg tgtagggtga gtgaggcacc gtccctgggt   14880
gtccctccca ggtatagggt gagtgaggca ctgtccccgg gtgtccctgt cacgtgcagg   14940
gtgagtgagg cgcggccccc gggtgtccct ctcaggtgca gggtgagtga ggcgctgtcc   15000
ctgggtgtcc ctgtctcgtg tagggtgagt gaggctctgt ccccaggtgt ccttggcgtt   15060
tgctcacttg agcttgctcc tgaatgtttg ctctttctat agccacagct gcgccggttg   15120
cccattgcct gggtagatgg tgcaggcgca gtgctggtcc ccaagcctat cttttctgat   15180
gctcggctct tcttggtcac ctctccgttc cattttgcta cggggacacg ggactgcagg   15240
ctctcgcctc ccgcgtgcca ggcactgcag ccacagcttc aggtccgctt gcctctgttg   15300
ggcctggctt gctcaccacg tgcccgccac atgcatgctg ccaatactcc tctcccagct   15360
tgtctcatgc cgaggctgga ctcgggctg cctgtgtctg ctgccacgtg ttgctggaga   15420
catcccagaa agggttctct gtgccctgaa ggaaagcaag tcaccccagc cccctcactt   15480
gtcctgtttt ctcccaagct gccctctgc ttggcccct tgggtgggtg gcaacgcttg   15540
tcaccttatt ctgggcacct gccgctcatt gcttaggctg ggctctgcct ccagtcgccc   15600
cctcacatgg attgacgtcc agccacaggt tggagtgtct ctgtctgtct cctgctctga   15660
gacccacgtg gagggccggt gtctccgcca gccttcgtca gacttccctc ttgggtctta   15720
gttttgaatt tcactgattt acctctgacg tttctatctc tccattgtat gcttttcttt   15780
ggtttattct ttcattcctt ttctagcttc ttagtttagt catgccttc cctctaagtg   15840 ctgccttacc tgcaccctgt gttttgatgt gaagtaatct caacatcagc cactttcaag   15900
tgttcttaaa atacttcaaa gtgttaatac ttctttaag tattcttatt ctgtgatttt   15960
tttctttgtg cacgctgtgt tttgacgtga aatcattttg atatcagtga cttttaagta   16020
ttctttagct tattctgtga tttctttgag cagtgagtta tttgaacact gtttatgttc   16080
aagatatgta gagtatcaag atacgtagag tattttaagt tatcatttta ttattgattt   16140
ctaactcagt tgtgtagtgg tctgtataat accaattatt tgaagtttgc ggagccttgc   16200
tttgtgatct agtgtgtgca tggttttccag aactgtccat tgtaaatttg acatcctgtc   16260
aatagtgggc atgcatgttc actatatcca gcttattaag gtccagtgca aagcttctgt   16320
ctccttctag atgcatgaaa ttccaagaag gaggccatag tccctcacct ggggatggg   16380 tctgttcatt tcttctcgtt tggtagcatt tatgtgaggc attgttaggt gcatgcacgt   16440
ggtagaattt ttatcttcct gatgagtgaa tcttttggag acttctatgt ctctagtaat   16500
ctagtaattc ttttttaaa ttgctcttag tactgccaca ctgggcttct tttgattagt   16560
attttcctgc tgtgtctgtt ttctgccttt aatttatata tatatatata tttttttttt   16620
ttttgagaca gagtcttggt ctgtcgccca gggtgagtgc agtggtgtga tcacaggtca   16680
gtgtaacttt taccttctgg cctgagccgt cctctcacct cagcctcctg agtagctgga   16740
actgcagaca cgcaccgcta cacctggcta attttaaat ttttctgga cagggtct    16800 tgctgtgttg cccaggctgg tctcaaactc ttggactcaa gggatccatc tacctcggct   16860
tcccaaagtg ctgaattaca ggcatgagcc accatgtctg gcctaatttt caacactttt   16920
atattcttat agtgtgggta tgtcctgtta acagcatgta ggtgaatttc caatccagtc   16980
tgacagtcgt tgtttaactg gataaccctga tttattttca tttttttgtc actagagacc   17040
cgcctggtgc actctgattc tccacttgcc tgttgcatgt cctcgttccc ttgtttctca   17100
ccacctcttg ggttgccatg tgcgtttcct gccgagtgtg tgttgatcct ctcgttgcct   17160
```

```
cctggtcact gggcatttgc ttttatttct ctttgcttag tgttaccccc tgatcttttt    17220
attgtcgttg tttgcttttg tttattgaga cagtctcact ctgtcaccca ggctggagtg    17280
taatggcaca atctcggctc actgcaacct ctgcctcctc ggttcaagca gttctcattc    17340
ctcaacctca tgagtagctg ggattacagg cgcccaccac cacgcctggc taattttttgt   17400 attttttagta gagataggct ttcaccatgt tggccaggct ggtctcaaac tcctgacctc    17460
aagtgatctg cccgccttgg cctcccacag tgctgggatt acaggtgcaa gccaccgtgc    17520
ccggcatacc ttgatctttt aaaatgaagt ctgaaacatt gctacccttg tcctgagcaa    17580 taagacccctt agtgtatttt agctctggcc accccccagc ctgtgtgctg ttttccctgc   17640
tgacttagtt ctatctcagg catcttgaca cccccacaag ctaagcatta ttaatattgt    17700
tttccgtgtt gagtgtttct gtagctttgc ccccgccctg cttttcctcc tttgttcccc    17760
gtctgtcttc tgtctcaggc ccgccgtctg gggtccccctt ccttgtcctt tgcgtggttc   17820
ttctgtcttg ttattgctgg taaacccccag ctttacctgt gctggcctcc atggcatcta   17880
gcgacgtccg gggacctctg cttatgatgc acagatgaag atgtgagac tcacgaggag     17940 ggcggtcatc ttggcccgtg agtgtctgga gcaccacgtg ccagcgttc cttagccagt     18000 gagtgacagc aacgtccgct cggcctgggt tcagcctgga aaaccccagg catgtcgggg    18060
tctggtggct ccgcggtgtc gagtttgaaa tcgcgcaaac ctgcggtgtg gcgccagctc    18120
tgacggtgct gcctggcggg ggagtgtctg cttcctccct tctgcttggg aaccaggaca    18180
aaggatgagg ctccgagccg ttgtcgccca acaggagcat gacgtgagcc atgtggataa    18240
ttttaaaatt tctaggctgg gcgcggtggc tcacgcctgt aatcccagca ctttgggagg    18300
ccaaggcggg tggatcacga ggtcaggagg tcgagaccat cctggccaac atgatgaaac    18360
cccatctgta ctaaaaacac aaaaattagc tgggcgtggt ggcgggtgcc tgtaatccca    18420
gctactcggg aggctgaggc aggagaattg cttgaacctg ggagttggaa gttgcagtga    18480
gccgacattg caccactgca ctccagcctg gcaacacagc gagactctgt ctcaaaaaaa    18540
aaaaaaaaaa aaaaaaaaa aattctagta gccacattaa aaagtaaaaa agaaaaggt      18600 gaaattaatg taataataga ttttactgaa gcccagcatg tccacacctc atcatttag     18660 ggtgttattg gtgggagcat cactcacagg acatttgaca ttttttgagc tttgtctgcg    18720
ggatcccgtg tgtaggtccc gtgcgtggcc atctcggcct ggacctgctg ggcttcccat    18780
ggccatggct gttgtaccag atggtgcagg tccgggatga ggtcgccagg ccctcagtga    18840
gctggatgtg cagtgtccgg atggtgcacg tctgggatga ggtcgccagg ccctgctgtg    18900
agctggatgt gtggtgtctg gatggtgcag gtcaggggtg aggtctccag gccctcggtg    18960
agctggaggt atggagtccg gatgatgcag gtccggggtg aggtcgccag gccctgctgt    19020
gagctggatg tgtggtgtct ggatggtgca ggtcagggt gaggtctcca ggccctcggt     19080
aagctggagg tatggagtcc ggatgatgca ggtccggggt gaggtcgcca ggccctgctg    19140
tgagctggat gtgtggtgtc tggatggtgc aggtctgggg tgaggtcacc aggccctgcg    19200
gtgagctggg tgtgcggtgt ctggatggtg caggtctgga gtgaggtcgc cagacggtgc    19260
cagaccatgc ggtgagctgg atatgcggtg tccggatggt gcaggtctgg ggtgaggttc    19320
ccaggccctg ctgtgagttg gatgtggggt gtccggatgc tgcaggtccg gtgtgaggtc    19380
accaggccct gctgtgagct ggatgtgtgg tgtctggatg gtgcaggtct ggggtgaagg    19440
tcgccaggcc cctgcttgtg agctggatgt gtggtgtctg gatggtgcag gtctggagtg    19500
aggtcgccag gccctcggtg agctggatgt gcagtgtcca gatggtgcag gtccggggtg    19560
```

```
aggtcgccag accctgcggt gagctggatg tgcggtgtct ggatggtgca ggtctggagt    19620
gaggtcgcca ggccctcggt gagctggatg tatggagtcc ggatggtgcc ggtccggggt    19680
gaggtcgcca gacccxgctg tgagctggat gtgcggtgtc tggatggtac aggtctggag    19740
tgaggtcgcc agaccctgct gtgagctgga tatgcggtgt ccggatggtg caggtcaggg    19800
gtgaggtctc caggccctcg gtgagctgga ggtatggagt ccggatgatg caggtccggg    19860
gtgaggtcgc caggccctgc tgtgaactgg atgtgcggcg tctggatggt gcaggtctgg    19920
ggtgtggtcg ccaggccctc ggtgagctgg aggtatggag tccggatgat gcaggtccgg    19980
ggtgaggtcg ccaggccctg ctgtgagctg gatgtgcggc gtctggatgg tgcaggtctg    20040
gggtgtggtc gccaggccct cggtgagctg gaggtatgga gtccggatga tgcaggtccg    20100
gggtgaggtt gccaggccct gctgtgagct ggatgtgctg tatccggatg gtgcagtccg    20160
gggtgaggtc gccaggccct gctgtgagct ggatgtgctg tatccggatg gtgcaggtct    20220
ggggtgaggt caccaggccc tgcggtgagc tggttgtgcg gtgtccggtt gctgcaggtc    20280
cggggtgagt tcgccaggcc ctcggtgagc tggatgtgcg gtgtccccgt gtccggatgg    20340
tgcaggtcca gggtgaggtc gctaggccct tggtgggctg gatgtgccgt gtccggatgg    20400
tgcaggtctg gggtgaggtc gccaggcctt tggtgagctg gatgtgcggt gtctgcatgg    20460
tgcaggtctg gggtgaggtc gccaggccct tggtgggctg gatgtgtggt gtccggatgg    20520
tgcaggtccg gcgtgaggtc gccaggccct gctgtgagct ggatgtgcgg tgtctggatg    20580
gtgcaggtcc gggtgaggt agccaaggcc ttcggtgagc tggatgtggg gtgtccggat    20640
ggtgcaggtc cggggtgagg tcgccaggcc ctgcggttag ctggatatgc ggtgtccgga    20700
tggtgcaggt ccggggtgag gtcaccaggc cctgcggtta ctggatgtg cggtgtctgg    20760 atggtgcagg tccggggtga ggtcgccagg ccctgctgtg agctggatgt gctgtatccg    20820
gatggtgcag gtccggggtg aggtcgccag gccctgcagt gagctggatg tgctgtatcc    20880
ggatggtgca ggtctggcgt gaggtcgcca ggccctgcgg ttagctggat atgcggtgtc    20940
ggatggtgca ggtccggggt gaggtcacca ggccctgcgg ttagctggat gtgcggtgtc    21000
cggatggtgc aggtctgggg tgaggtcgcc aggccctgct gtgagctgga tgtgctgtat    21060
ccggatggtg caggtccggg gtgaggtcgc caggccctgc ggtgagctgg atgtgctgta    21120
tccggatggt gcaggtctgg cgtgaggtcg ccaggccctg cggtgagctg gatgtgcagt    21180
gtacggatgg tgcaggtccg gggtgaggtc gccaggccct gcggtgggct gtatgtgtgt    21240
tgtctggatg gtgcaggtcc ggggtgagtt cgccaggccc tgcggtgagc tggatgtgtg    21300
gtgtctggat gctgcaggtc cggggtgagt tcgccaggcc ctcggtgagc tggatatgcg    21360
gtgtccccgt gtccgaatgg tgcaggtcca gggtgaggtc gccaggccct tggtgggctg    21420
gatgtgccgt gtccggatgg tgcaggtctg gggtgaggtc gccaggccct tggtgagctg    21480
gatgtgcggt gtccggatgg tgcaggtccg gggtgaggtc accaggccct cggtgatctg    21540
gatgtggcat gtccttctcg tttaaggggt tggctgtgtt ccggccgcag agcaccgtct    21600
gcgtgaggag atcctggcca agttcctgca ctggctgatg agtgtgtacg tcgtcgagct    21660
gctcaggtct ttcttttatg tcacggagac cacgtttcaa aagaacaggc tcttttcta    21720 ccggaagagt gtctggagca agttgcaaag cattggaatc aggtactgta tccccacgcc    21780
aggcctctgc ttctcgaagt cctggaacac cagcccggcc tcagcatgcg cctgtctcca    21840
cttgcctgtg cttccctggc tgtgcagctc tgggctggga gccaggggcc ccgtcacagg    21900
```

```
cctggtccaa gtggattctg tgcaaggctc tgactgcctg gagctcacgt tctcttactt   21960
gtaaaatcag gagtttgtgc caagtggtct ctagggtttg taaagcagaa gggatttaaa   22020
ttagatggaa acactaccac tagcctcctt gcctttccct gggatgtggg tctgattctc   22080
tctctctttt tttttttcttt tttgagatgg agtctcactc tgttgcccag gctggagtgc   22140
agtggcataa tcttggctca ctgcaacctc cacctcctgg gtttaagcga ttcaccagcc   22200
tcagcctcct aagtagctgg gattacaggc acctgccacc acgcctggct aattttttgta   22260 cttttaggag agacggggtt tcaccatgtt ggccaggctg gtctcgaact catgacctca   22320
ggtgatccac ccaccttggc ctcccaaagt gctgggttta caggctaagc caccgtgccc   22380
agcccccgat tctcttttaa ttcatgctgt tctgtatgaa tcttcaatct attggattta   22440
ggtcatgaga ggataaaatc ccacccactt ggcgactcac tgcagggagc acctgtgcag   22500
ggagcacctg gggataggag agttccacca tgagctaact tctaggtggc tgcatttgaa   22560
tggctgtgag attttgtctg caatgttcgg ctgatgagag tgtgagattg tgacagattc   22620
aagctggatt tgcatcagtg agggacggga gcgctggtct gggagatgcc agcctggctg   22680
agcccaggcc atggtattag cttctccgtg tcccgcccag gctgactgtg gagggcttta   22740
gtcagaagat cagggcttcc ccagctcccc tgcacactcg agtccctggg gggccttgtg   22800
acaccccatg ccccaaatca ggatgtctgc agagggagct ggcagcagac ctcgtcagag   22860
gtaacacagc ctctgggctg ggacccccga cgtggtgctg gggccatttc cttgcatctg   22920
ggggagggtc agggctttcc ctgtgggaac aagttaatac acaatgcacc ttacttagac   22980
tttacacgta tttaatggtg tgcgacccaa catggtcatt tgaccagtat tttggaaaga   23040
atttaattgg ggtgaccgga aggagcagac agacgtggtg gtccccaaga tgctccttgt   23100
cactactggg actgttgttc tgcctggggg gccttggagg ccctcctcc ctggacaggg   23160 taccgtgcct tttctactct gctgggcctg cggcctgcgg tcagggcacc agctccggag   23220
cacccgcggc cccagtgtcc acggagtgcc aggctgtcag ccacagatgc ccaggtccag   23280
gtgtggccgc tccagccccc gtgcccccat gggtggtttt ggggggaaaag gccaagggca   23340 gaggtgtcag gagactggtg ggctcatgag agctgattct gctccttggc tgagctgccc   23400
tgagcagcct ctcccgccct ctccatctga agggatgtgg ctcttctac ctgggggtcc   23460 tgcctggggc cagccttggg ctaccccagt ggctgtacca gagggacagg catcctgtgt   23520 ggagggcat gggttcacgt ggccccagat gcagcctggg accaggctcc ctggtgctga   23580
tggtgggaca gtcaccctgg gggttgaccg ccggactggg cgtccccagg gttgactata   23640
ggaccaggtg tccaggtgcc ctgcaagtag aggggctctc agaggcgtct ggctggcatg   23700 ggtgacgtg gccccgggca tggccttcag cgtgtgctgc cgtgggtgcc ctgagccctc   23760
actgagtcgg tgggggcttg tggcttcccg tgagcttccc cctagtctgt tgtctggctg   23820
agcaagcctc ctgaggggct ctctattgca gacagcactt gaagagggtg cagctgcggg   23880
agctgtcgga agcagaggtc aggcagcatc gggaagccag gccgccctg ctgacgtcca   23940 gactccgctt catccccaag cctgacgggc tgcggccgat tgtgaacatg gactacgtcg   24000
tgggagccag aacgttccgc agagaaaaga gggtggctgt gctttggttt aacttccttt   24060
ttaaacagaa gtgcgtttga gccccacatt tggtatcagc ttagatgaag gcccggagg   24120 agggggcacg ggacacagcc agggccatgg cacggcgcca acccatttgt gcgcacagtg   24180
aggtggccga ggtgccggtg cctccagaaa agcagccgtgg gggtgtaggg ggagctcctg   24240
gggcagggac aggctctgag gaccacaaga agcagccggg ccagggcctg gatgcagcac   24300
```

```
ggcccgaggt cctggatccg tgtcctgctg tggtgcgcag cctccgtgcg cttccgctta   24360
cggggcccgg ggaccaggcc acgactgcca ggagcccacc gggctctgag gatcctggac   24420
cttgccccac ggctcctgca ccccacccct gtggctgcgg tggctgcggt gaccccgtca   24480
tctgaggaga gtgtggggtg aggtggacag aggtgtggca tgaggatccc gtgtgcaaca   24540
cacatgcggc caggaacccg tttcaaacag ggtctgagga agctgggagg ggttctaggt   24600
cccgggtctg ggtggctggg gacactgggg aggggctgct tctcccctgg gtccctatgg   24660
tggggtgggc acttggccgg atccactttc ctgactgtct cccatgctgt cccgccagg    24720 ccgagcgtct cacctcgagg gtgaaggcac tgttcagcgt gctcaactac gagcgggcgc   24780
ggcgccccgg cctcctgggc gcctctgtgc tgggcctgga cgatatccac agggcctggc   24840 gcacttcgt gctgcgtgtg cgggcccagg acccgccgcc tgagctgtac tttgtcaagg    24900
tgggtgccgg ggaccccgt gagcagccct gctggacctt gggagtggct gcctgattgg    24960
cacctcatgt tgggtggagg aggtactcct gggtgggccg cagggagtgc aggtgaccct   25020
gtcactgttg aggacacacc tggcacctag ggtggaggcc ttcagccttt cctgcagcac   25080
atggggccga ctgtgcaccc tgactgcccg ggctcctatt cccaaggagg gtcccactgg   25140
attccagttt ccgtcagaga aggaaccgca acggctcagc caccaggccc cggtgccttg   25200 cacccccagtc ctgagccagg ggtctcctgt cctgaggctc agagagggga cacagcccgc  25260
cctgcccttg gggtctggag tggtgggggt cagagagaga gtgggggaca ccgccaggcc   25320
aggccctgag ggcagaggtg atgtctgagt ttctgcgtgg ccactgtcag tctcctcgcc   25380
tccactcaca caggtggatg tgacgggcgc gtacgacacc atcccccagg acaggctcac   25440
ggaggtcatc gccagcatca tcaaacccca gaacacgtac tgcgtgcgtc ggtatgccgt   25500
ggtccagaag gccgcccatg ggcacgtccg caaggccttc aagagccacg taaggttcac   25560
gtgtgatagt cgtgtccagg atgtgtgtct ctgggatatg aatgtgtcta gaatgcagtc   25620
gtgtctgtga tgcgtttctg tggtggaggt acttccatga tttacacatc tgtgatatgc   25680
gtgtgtggca cgtgtgtgtc gtggtgcatg tatctgtggc gtgcatattt gtggtgtgtg   25740
tgtgtgtggc acgtgtgtgt ccatggtgtg tgtgcctgtg gtgtgcatgt gtgtgtgtct   25800
gtgacacgtg catgttcatg ctgtgtgctg catgtctgtg atgtgcctat ttgtggtgtg   25860
tgtgtgcatg tgtccgtgac atatgcgtgt ctatggcatg ggtgtgtgtg gcccttggc   25920 cttactcctt cctcctccag gcatggtccg caccattgtc ctcacgctct cgggtgctgg   25980
tttggggagc tccacattca gggtcctcac ttctagcatg ggtgcccctg tcctgtcaca   26040
gggctgggcc ttggagactg taagccaggt ttgagaggag agtagggatg ctggtggtac   26100
cttcctggac ccctggcacc cccaggaccc cagtctggcc tatgccggct ccatgagata   26160
taggaaggct gattcaggcc tcgctccccg ggacacactc ctcccagagc ggccgggggc   26220 cttgggctc ggcaggggtg aaaggggccc tgggcttggg ttcccaccca gtggtcatga    26280
gcacgctgga ggggtaagcc ctcaaagtcg tgccaggccg gggtgcagag gtgaagaagt   26340
atccctggag cttcggtctg gggagaggca catgtggaaa cccacaagga cctctttctc   26400
tgacttcttg agcttgtggg attggttttc atgtgtggga taggtgggga tctgtgggat   26460
tggtttttat gagtggggta acacagagtt caaggcgagc tttcttcctg tagtgggtct   26520
gcaggtgctc caacagcttt attgaggaga ccatatcttc ctttgaacta tggtcggtt    26580 tatagtaagt caggggtgtg gaggcctccc ctgggctccc tgttctgttt cttccactct   26640
```

```
ggggtcgtgt ggtgcctgct gtggtgtgtg gccggtgggc agggcttcca ggcctccttg   26700
tgttcattgg cctggatgtg gccctggcta cgctccgtcc ttggaattcc cctgcgagtt   26760
ggaggctttc tttctttctt ttttctttc ttttttttt tttttgataa cagagtctcg    26820
ctcttttttg cccaggctgg agtggtttgg cgtgatcttg gctcactgca acctgtgctt   26880
cctgagttca agcaattctc ttgcctcagc ctcccaagta gctggaatta taggcgccca   26940
ccaccatgct gactaatttt tgtaatttta gtagagacga ggtttctcca tgttggccag   27000
gctggtctcg aactcctgac ctcaggtgat cctcccacct cggcctccca aagtgctggg   27060
atgacaggtg tgaaccgccg cgcccggccg agactcgctt cctgcagctt ccgtgagatc   27120
tgcagcgata gctgcctgca gccttggtgc tgacaacctc cgttttcctt ctccaggtct   27180
cgctaggggt ctttccattt catgactctc ttcacagaag agtttcacgt gtgctgattt   27240
cccggctgtt tcctgcgtaa ttggtgtctg ctgtttatcg atggcctcct tccatttcct   27300
ttaggctttg tttattgttg ttttttccggc tccttgaagg aaaagtttcg attatggatg   27360
tttgaacttt cttttctaaa caagcatctg aagttgccgt tttccctcta aagcagggat   27420
cccgaggccc ctggctgtgg agtggcaccg gtctggggcc tgttaggaac ccggcgcaca   27480
gcgggaggct aggtgggggtg tggggagcca gcgttcccgc ctgagcccg cccctctcag   27540 atcagcagtg gcatgcggtg ctcagaggcg cacacaccct actgagaact gtgcgtgaga   27600
ggggtctaga ttctgtgctc cttatgggaa tctaatgcct gatgatcga ggtggaaccg    27660 tttgctccca aaaccatccc cttccccact gctgtcctgt ggaaaaatcg tcttccacga   27720
aaccagtccc tggtaccaca atggttgggg accctgtgct aaagacctgc ttcagcagcc   27780
tctcgtcagt gttgatatat tggcttttct gtgttgagtc cagaataatt acggatttct   27840
gtgatgcttt ccgccgacct cagacccatg ggctatttgt gggcgtgttg cctgctcctg   27900
ggttgggaag ggtgcaggcc ccatgtacct tcctgttact gccttccagg ttggttctca   27960
gggttgaatc gtactcgatg tggttttagc ccacggccct gccgccagct cctgggggct   28020
ggggaacatg ctgaagcaca gagtcaccgt gcgcgtcttt tgatgcctca caagctcgag   28080
gcctcctgtg tccgtgttag tgtgtgtcac gtgcctgctc acatcctgtc ttggggacgc   28140
aggggcttag caggtcccgt agtaaatgac aagcgtcctg ggggagtctg cagaatagga   28200
ggtgggggtg ccggtctctc tcccgcgtct tcagactctt ctcctgcctg tgctgtggct   28260
gcacctgcat ccctgcaatc cctccagcac tgggctggag aggcccggga gctcgagtgc   28320
cacttgtgcc acgtgactgt ggatggcagt cggtcacggg ggtctgatgt gtggtgactg   28380
tggatggcgg ttggtcacag gggtctgatg tgtggtgact gtggatggcg gtcgtggggt   28440
ctgatgtggt gactgtggat ggcggtcgtg gggtctgatg tgtggtgact gtggatggcg   28500
gtcgtggggt ctgatgtggt gactgtggat ggcggtcgtg gggtctgatg tggtgactgt   28560
ggatggcggt cgtggggtct gatgtggtga ctgtggatgg cagtcgtggg gtctgatgtg   28620
tggtgactgt ggatggcggt cgtggggtct gatgtggtga ctgtggatgg cagtcgtggg   28680
gtctgatgtg tggtgactgt ggatggcggt cgtggggtct gatgtgtggt gactgtggat   28740
ggcggtcgtg gggtctgatg tgtggtgact gtgatggcg tcgtggggt ctgatgtgtg    28800 gtgactgtgg atggcggtcg tggggtctga tgtggtgact gtggatggcg tcgtggggt    28860 ctgatgtgtg gtgactgtgg atggtgatcg gtcacagggg tctgatgtgt ggtgactgtg   28920
gatggcggtc gtggggtctg atgtgtggtg actgtggatg gtgatcggtc acaggggtct   28980
gatgtgtggt gactgtggat ggcggtcgtg gggtctgatg tgtggtgact gtggatggcg   29040
```

```
gttggtcccg ggggtctgat gtgtggtgac tgtggatggc gatcggtcac agggtctga    29100
tgtgtggtga ctgtggatgg cggtcgtggg gtctgatgtg tggtgactgt ggatggcggt    29160
cgtggggtct gatgtgtggt gactgtggat ggcggtcgtg gggtctgatg tggtgactgt    29220
ggatggcggt cgtggggtct gatgtggtga ctgtggatgg cggtcgtggg gtctgatgtg    29280
tggtgactgt ggatggcggt tggtcccggg ggtctgatgt gtggtgactg tggatggcgg    29340
tcgtggggtc tgatgtggtg actgtggatg gcagtcgtgg ggtctgatgt gtggtgactg    29400
tggatggcgg tcgtggggtc tgatgtgtgg tgactgtgga tggcggtcgt ggggtctgat    29460
gtgtggtgac tgtggatggc ggtcgtgggg tctgatgtgt ggtgactgtg gatggcggtc    29520
gtgggtctg atgtggtgac tgtggatggc ggtcgtgggg tctgatgtgt ggtgactgtg    29580
gatggtgatc ggtcacaggg gtctgatgtg tggtgactgt ggatggcggt cgtggggtct    29640
gatgtgtggt gactgtggat ggcggtcgtg gggtctgatg tggtgactgt ggatggcggt    29700
cgtggggtct gatgtgtggt gactgtggat ggcggtcgta gggtctgatg tgtggtgact    29760
gtggatggca gtcggtcaca ggggtctgat gtgtggtgac tgtggatggc ggtcgtgggg    29820
tctgatgtgt ggtgactgtg gatggcggtc gtgggtctg atgtggtgtg actgtggatg    29880
gcggtcgtgg ggtctgatgt gtggtgactg tggatggcgg tcgtggggtc tgatgtggtg    29940
actgtggatg gtgatcggtc acaggggtct gatgtgtggt agctgcaggt ggagtcccag    30000
gtgtgtctgt agctactttg cgtcctcggc ccccggccc ccgtttccca aacagaagct    30060
tcccaggcgc tctctgggct tcatcccgcc atcgggcttg ccgcaggtc cacacgtcct    30120
gatcggaaga aacaagtgcc cagctctggc cggggcaggc cacatttgtg gctcatgccc    30180
tctcctctgc cggcaggtct ctaccttgac agacctccag ccgtacatgc gacagttcgt    30240
ggctcacctg caggagacca gcccgctgag ggatgccgtc gtcatcgagc aggtctgggc    30300
actgccctgc agggttgggc acggactccc agcagtgggt cctcccctgg gcaatcactg    30360
ggctcatgac cggacagact gttggccctg ggggcagtg ggggaatga ctgtgatgg    30420
gggcatgatg agctgtgtgc cttggcgaaa tctgagctgg gccatgccag gctgcgacag    30480
ctgctgcatt caggcacctg ctcacgtttg actgcgcggc ctctctccag ttccgcagtg    30540
cctttgttca tgatttgcta aatgtcttct ctgccagttt tgatcttgag gccaaaggaa    30600
aggtgtcccc ctcctttagg agggcaggcc atgtttgagc cgtgtcctgc ccagctggcc    30660
cctcagtgct gggtctgagg ccaaaggaaa cgtgtccccc ttcttaggag gacgggccgt    30720
gtttgagcca cgcccgctg agcgggcctc tcagtgctgg gtctgtccac gtggccctgt    30780
ggccctttgc agatgtggtc tgtccacgtg gccctgtggc tctttgcaga tgcctgttag    30840
cacttgctcg gctctagggg acagtcgtgt ccaccgcatg aggctcagag acctctgggc    30900
gaatttcctt ggctcccagg gtgggggtgg aggtggcctg ggctgctggg acccagaccc    30960
tgtgcccggc agctgggcag caactcctgg atcacatatg ccatccgggc cacggtgggc    31020
tgtgtgggtg tgagcccagc tggacccaca ggtggcccag aggagacgtt ctgtgtcaca    31080
cactctgcct aagcccatgt gtgtctgcag agactcggcc cggccagccc acgatggccc    31140
tgcattccag cccagccccg cacttcatca caaacactga cccaaaagg gacggagggt    31200
cttggccacg tggtcctgcc tgtctcagca cccaccggct cactcccatg tgtctcccgt    31260
ctgctttcgc agagctcctc cctgaatgag gccagcagtg gcctcttcga cgtcttccta    31320
cgcttcatgt gccaccacgc cgtgcgcatc aggggcaagt gagtcaggtg gccaggtgcc    31380
```

```
attgccctgc gggtggctgg gcgggctggc agggcttctg ctcacctctc tcctgcccct   31440
tccccactgn ccttctgccc ggggccacca gagtctcctt ttctggcccc cgccccctcc   31500
ggctcctggg ctgcaggctc ccgaggcccc ggaaacatgg ctcggcttgc ggcagccgga   31560
gcggagcagg tgccacacga ggcctggaaa tggcaagcgg ggtgtggagt tgctcctgcg   31620
tggaggacga ggggcggggg gtgtgtctgg gtcaggtgtg cgccgagcgt ttgagcctgc   31680
agcttgtcag ctccaagtta ctactgacgc tggacacccg gctctcacac gcttgtatct   31740
ctctctcccg atacaaaagg attttatccg attctcattc ctgtccctgt cgtgtgaccc   31800
ccgcgagggc gcgggctctt ctctctgtga ctagatttcc catctggaaa gtgcggggtt   31860
gaccgtgtag tttgctcctc tcggggggcc tgtggtggcc atggggcagg cggcctggga   31920
gagctgccgt cacacagcca ctgggtgagc cacactcacg gtggtagagc cacagtgcct   31980
ggtgccacat cacgtcctct ggattttaag taaaaccaca cacctcccgg caggcatctg   32040
cctgcgaccc tgtgtgtgcc tggggagagt ggtagcacgg aggaaattcg tgcacactca   32100
aggtcatcag caaggtcatc cgcagtcagg tggaacgtgg aggcctctct ctgggatcgt   32160
ctccagcgga taaggactg tgcacagctt cggaagcttt tatttaaaaa tataactatt   32220
aattattgca ttataagtaa tcactaatgg tatcagcaat tataatattt attaaagtat   32280
aattagaaat attaagtagt acacacgttc tggaaaaaca caaattgcac atggcagcag   32340
agtgaatttt ggccgaggga cacgtgtgca catgtgtgta agcggccccc aggcccacag   32400
aattcgctga caaagtcacc tccccagaga agccaccacg ggcctccttc gtggtcgtga   32460
attttattaa gatggatcaa gtcacgtacc gtccacgtgt ggcagggctt tggggaatgt   32520
gaggtgatga ctgcgtcctc atgccctgac agacaggagg tgactgtgtc tgtcctgtcc   32580
ctaggacacg gacaggcccg aagctctagt ccccatcgtg gtccagtttg gcctctgaat   32640
aaaaacgtct tcaaaacctg ttgccccaaa aactaagaac agagagagtt tcccatccca   32700
tgtgctcaca ggggcgtatc tgcttgcgtt gactcgctgg gctggccgga ctcctagagt   32760
tggtgcgtgt gcttctgtgc aaaaagtgca gtcctcttgc ccatcactgt gatatctgca   32820
ccagcaagga aagcctcttt tcttttcttt cttttttttt ttttgagacg gaacgtcact   32880
gttgtctgcc tgggcttgag tgcagtggcg cgatctcaac tcactgcaac ctccgcctcc   32940
cgggttccag catttctcct gcctcagcct cccgagcagc tgagattaca ggcacccacc   33000
ccctgcgcct ggctaatttt tgtatttta gtagagaggg gttttgccca tgttggccag   33060
gctggtctcg aactcctgac ctcaggtgat ccacccacct cggcctccca aagtgctggg   33120
attacaggtg tgagccatca cgcccagccg gaaagcctct ttttaaggtg accacctata   33180
gcgcttcccg aaaataacag gtcttgtttt tgcagtaggc tgcaagcgtc tcttagcaac   33240
aggagtggcg tcctgtgggc tctggggatg gctgagggtc gcgtggcagc catgccttct   33300
gtgtgcacct ttaggttcca cggggctatt ctgctctcac tgtttgtctg aaaacgcacc   33360
cttggcatcc ttgtttggag agtttctgct tctcgttggt catgctgaaa ctaggggcaa   33420
ggttgtatcc gttggcgcgc agcggctaca tgtagggtca tgagtctttc accgtggaca   33480
aattccttga aaaaaaaaaa aggagtccgg ttaagcattc attccgggtc aagtgtctgg   33540
ttctgtgaat aaactctaag atttaagaaa ccttaatgaa agaaaccttt gatgattcag   33600
agcaaggatg tggtcacacc tgtggctgga tctgtttcag ccgcccagt gcatggtgag   33660
agtgggagc agggattgtt tgttcagagg tctcatctgg tatgtttctg aggtgtttgc   33720
cggctgaatg gtagacgtgt cgtttgtgtg tatgaggttc tgtgtctgtg tgtggctcgg   33780
```

```
tttgagtgta cgcatgtcca gcacatgccc tgcccgtctc tcacctgtgt cttcccgccc    33840
caggtcctac gtccagtgcc aggggatccc gcagggctcc atcctctcca cgctgctctg    33900
cagcctgtgc tacggcgaca tggagaacaa gctgtttgcg gggattcggc gggacgggtg    33960
aggcctcctc ttccccaggg gggcttgggt ggggggttgat ttgcttttga tgcattcagt    34020
gttaatattc ctggtgctct ggagaccatg actgctctgt cttgaggaac cagacaaggt    34080
tgcagcccct tcttggtatg aagccgcacg ggaggggttg cacagcctga ggactgcggg    34140
ctccacgcag gctctgtcca gcggccatgt ccagaggcct cagggctcag caggcgggag    34200
ggccgctgcc ctgcatgatg agcatgtgaa ttcaacaccg aggaagcaca ccagcttctg    34260
tcacgtcacc caggttccgt tagggtcctt ggggagatgg ggctggtgca gcctgaggcc    34320
ccacatctcc cagcaggccc tcgacaggtg gcctggactg ggcgcctctt cagcccattg    34380
cccatcccac ttgcatgggg tctacaccca aggacgcaca cacctaaata tcgtgccaac    34440
ctaatgtggt tcaactcagc tggcttttat tgacagcagt tactttttt tttttaatac    34500 tttaagttct agggtacatg tgcacgacgt gcaggttagt tacatatgta tacatgtgcc    34560
atgttggtgt gctgcaccca ttaactcatc atttacatta ggtatatctc ctaatgctat    34620
ccctccccac tccccccatc ccatgacagg ccctggtgtg tgatgttccc caccctgtgt    34680
ccaagtgttc tcattgttca gttcccacct gtgagtgaga acatgtggtg tttggttttc    34740
tttccttgca atagtttgct cagagtgatg gtttccagct tcgtccatgt ccctacaaag    34800
gacatgaact catcctttt tatgactgca tagtattccg tggtgtatat gtgccacatt    34860
ttcttaatcc agtctatcat cgatggacat ttgggttggt tgcaagtctt tgctactgtg    34920
aatagtgccg caataaacat acgtgtgcat gtgtctttat agcagcatga tttataatcc    34980
tttgggtata tacccagtaa tgggatggct gggtcaaatg gtatttctag ttctagatcc    35040
ttgaggaatc accacactgt cttccacaat ggttgaacta gtttacactc ccaccaacag    35100
tgtaaaagtg ttctggtgct ggagaggatg tggacagcag ttattttttt atgaaaatag    35160
tatcactgaa caagcagaca gttagtgaag gatgcgtcag gaagcctgca ggccacacag    35220
ccatttctct cgaagactcc gggttttttcc tgtgcatctt ttgaaactct agctccaatt    35280
atagcatgta cagtggatca aggttcttct tcattaaggt tcaagttcta gattgaaata    35340
agtttatgta acagaaacaa aaatttcttg tacacacaac ttgctctggg atttggagga    35400
aagtgtcctc gagctggcgg cacactggtc agccctctgg gacaggatac ctctggccca    35460
tggtcatggg gcgctgggct tgggcctgag ggtcacacag tgcaccatgc ccagcttcct    35520
gtggatagga tctgggtctc ggatcatgct gaggaccaca gctgccatgc tggtaaaggg    35580
caccacgtgg ctcagagggg gcgaggtcc cagcccagc tttcttaccg tcttcagtta    35640 ttttcccta agagtctgag aagtggggcc gcgcctgatg gccttcgttc gtcttcagct    35700
ggcacagaat tgcacaagct gatggtaaac actgagtact tataatgaat gaggaattgc    35760
tgtagcagtt aactgtagag agctcgtctg ttggaaagaa atttaagttt ttcatttaac    35820
cgctttggag aatgttactt tatttatggc tgtgtaaatt gtttgacatt cagtccctcg    35880
tagacagata ctacgtaaaa agtgtaaagt taaccttgct gtgtattttc ccttatttta    35940
ggctgctcct gcgtttggtg gatgatttct tgttggtgac acctcacctc acccacgcga    36000
aaaccttcct caggtgaggc ccgtgccgtg tgtctgtggg gacctccaca gcctgtgggc    36060
tttgcagttg agccccccgt gtcctgcccc tggcaccgca gcgttgtctc tgccaagtcc    36120
```

```
tctctctctg ccggtgctgg atccgcaaga gcagaggcgc ttggccgtgc acccaggcct    36180
gggggcgcag gggcaccttc gggagggagt gggtaccgtg caggccctgg tcctgcagag    36240
acgcacccag gttacacacg tggtgagtgc aggcggtgac ctggctcctg ctgctctttg    36300
gaaagtcaag agtggcggct cctggggccc cagtgagacc cccaggagct gtgcacaggg    36360
cctgcagggc cgaggcggca gcctcctccc cagggtgcac ctgagcctgc ggagagcagg    36420
agctgctgag tgagctggcc cacagcgttc gctgcggtca cgttcctgcg tggggttgtt    36480
tgggatcggt gggagaattt ggatttgctg agtgctgctg tcttgaacca cggagatggc    36540
taggagtggg tttcagagtt gattttttgtg aatcaaacta aaatcaggca caggggacct    36600
ggcctcagca caggggattg tccaatgtgg tccccctcaa gggcgcccca cagagccggt    36660
gggcttgttt taaagtgcga tttgacgagg gacgagaaac cttgaaagct gtaaagggaa    36720
ccctcagaaa atgtggccgc caggggtggt ttcaggtgct ttgctgggct gtgtttgtga    36780
aaacccattt ggacccgccc tccaagtcca ccctccaggt ccaccctcca gggccgccct    36840
gggctggggg tatgcctggc gttccttgtg ccgcagcccg gagcacagca ggctgtgcac    36900
atttaaatcc actaagattc actcgggggg agcccaggtc ccaagcaact gagggctcag    36960
gagtcctgag gctgctgagg ggacagagca gacggggaac gctgcttctg tgtggcaagt    37020
tcctgagggt gctggccagg gaggtggctc agagtgtatg ttggggtccc accgggggca    37080
gaactctgtc tctgatgagt cggcagccat gtaacaggaa ggggtggcca cagggagctg    37140
ggaatgcacc aggggagctg cgcagctggc cgaggtccca gggccaggcc acaggaaggg    37200 caggggggacc cccggggcca cagcagaggc cgcaggaagg gaagggggatg cccaggccag    37260 agcagaggct accgggcaca ggggggctcc ctgagctggg tgagcgaggc tcatgactcg    37320
gcgagggaac ctccttgacg tgaagctgac gactggtgtt gcccagctca cagcccagcc    37380
aggtcccgcg cctgagcagg aactcagaac cctcccctt tgtctaaagca cagcagatgc    37440 cttcagggca tctaggagaa aacaggcaaa gtcgttgaga aacgtcttaa aagaaggtgg    37500
gatggtggca atttcttgtc cagattttag tctgccccgg accacagatg agtctataac    37560
gggattgtgg tgttgccatg gggacacatg agatggacca tcacagaggc cactgggggct    37620 gcacctccca tctgagtcct ggctgtcccg gtccaggcc aggttcttgc atgctcacct    37680
acctgtcctg cccgggagac agggaaagca ccccgaagtc tggagcaggg ctgggtccag    37740
gctcctcaga gctcctgcca ggcccagcac cctgctccaa atcaccactt ctctggggtt    37800
ttccaaagca tttaacaagg gtgtcaggtt acctcctggg tgacggcccc gcatcctggg    37860
gctgacattg cccctctgcc ttaggaccct ggtccgaggt gtccctgagt atggctgcgt    37920
ggtgaacttg cggaagacag tggtgaactt ccctgtagaa gacgaggccc tgggtggcac    37980
ggcttttgtt cagatgccgg cccacggcct attcccctgg tgcggcctgc tgctggatac    38040
ccggaccctg gaggtgcaga gcgactactc caggtgagcg cacctggccg gaagtggagc    38100
ctgtgcccgg ctggggcagg tgctgctgca ggccgttgc gtccacctct gcttccgtgt    38160
ggggcaggcg actgccaatc ccaaagggtc agaggccaca gggtgcccct cgtcccatct    38220 gggctgagc agaaatgcat ctttctgtgg gagtgagggt gctcacaacg ggagcagttt    38280
tctgtgctat tttggtaaaa ggaaatggtg caccagacct gggtgcactg aggtgtcttc    38340
agaaagcagt ctggatccga acccaagacg cccgggccct gctggcgtg agtctctcaa    38400 acccgaacac aggggccctg ctgggcatga gtccctctga acccgagacc ctggggccct    38460
gctgggcgtg agtctctccg aacccagaga cttcagggcc ctttttgggcg tgagtctctc    38520
```

```
cgctgtgagc cccacactcc aaggctcatc cacagtctac aggatgccat gagttcatga   38580
tcacgtgtga cccatcaggg gacagggcca tggtgtgggg ggggtctcta caaaattctg   38640
gggtcttgtt tccccagagc ccgagagctc aaggccccgt ctcaggctca gacacaaatg   38700
aattgaagat ggacacagat gcagaaatct gtgctgtttc ttttatgaat aaaaagtatc   38760
aacattccag gcagggcaag gtggctcaca cctataatcc cagcactttg ggaggccgag   38820
gtgggtggat cacttgaggc caggagtttg aggccaacct aaccaacata gtgaaattcc   38880
atttctactt aaaaaataca aaaattagcc tggcctggtg gcacacgcct gtagtcccog   38940 ctatgcggga ggctgaggca ggagaatcat ttgaacccag gaggcagagg ttgcagtgag   39000
ccgagatcac accactgcac tccagcctgg gcaacagagt gagacttcat cttaaaaaaa   39060
aaaaaaaaag tatcagcatt ccaaaaccat agtggacagg tgttttttta ttctgtcctt   39120
cgataatatt tactggtgct gtgctagagg ccggaactgg gggtgccttc ctctgaaagg   39180
cacaccttca tgggaagaga aataagtggt gaatggttgt taaaccagag gtttaaactg   39240
gggtcctgtc gttctgagtt aacagtccag atctggactt tgcctctttc cagaatgctc   39300
cctgggtttt gcttcatggg ggagcagcag gtgtggacac cctcgtgatg ggggagcagc   39360
aggtgcagac gccctcatga tgggggagtg gcaggtgcag acaccttgt gcatggtgcc    39420 cagcatgtcc ctgttgcagc tccctcccca caaggatgcc ggtctcctgt gctcccaca    39480 gtccctgctt ccctctcaca gccttacctg gtcctggcct ccactggctt tgtctgcatg   39540
atttccacat ttcctgggct cccagcacct cttcgcctct cccaggcacc tctgcagtgc   39600
tggccatacc agtcagctgt gaactgtcca ctgcttattt tgctccccat gaaatgtatt   39660
ttttaggaca ggcaccoctg gttccagcct ctggcacagc atcagtgaat gttattgaag   39720
gacaaaggac agacaaacaa atcaggaaaa tgggttctct ctaaacacat tgcaaagcca   39780
cagaggctag tgcaggatgg gtgggcatca ggtcatcaga tgtgggtcca atgccagaat   39840
attctgtgct cccaaaggcc acttggtcag agtgtgtgct tgcagaggtg gctctaaaag   39900
ctcagcagtg gaggcagtgg ttcgccatac tcagggtgaa ctcacatcct ctgtgtctga   39960
agtatacagc agaggcttga agggcatctg ggagaagaaa acaggcaaaa tgattaagaa   40020
aagtgaaaaa ggaaaagtgg taagatggga attttcttgt ccagatttta gtctcccaaa   40080
ccacagctca gatggtagaa tgtggtcaga actgatggac agaacaatag aacaaaacgg   40140
aagccctatc tctcagaaac gtgtgttaat gtggtatgtg gcacagctga tggaaaagag   40200
agtgtgtgtg taattttttt ttctgagaaa actgactgga agcaaataag ttgtgtcttt   40260
acagcatata ccagagcaga ttctaggtag aagaggagac acatgcaaac aacaccagca   40320
acagaaataa aacaaaagac tcaaaggaa gggaggtgaa cgttccctgg tttggtgttg    40380
gggaaggaca cacagggagg cggatgaaac cagtgaggca acgggcattg ctttcactgc   40440
agagaaactc agcttgcctg agccacagtg aaaatggcca ttccctggag cgtttgtgca   40500
cgtgatttat ttaaggcgcc ctgtgaggtc ctgcacattc atcctctcac tttgttctcc   40560
taaccacctg agaggtagag gaggaaaggc tccaggggag cagccgccct tggtcaccca   40620
gctggcaaag ggcatgcatg attgcagcct ggcctcctgc tccggggccc ttgctctgcc   40680
cgaggacccc acacaagtca gacccatagg ctcagggtga gccggagccc aaggtcgtgt   40740
tggggatggc tgtgaaagaa gaaatggacg tctgatgcac acttgggaag gtcctaccag   40800
cagcgtcaaa gaaatgcatg tgaaactgac agcgagaccc atccctcaaa gaaacgcacg   40860
```

```
tgaaactgat ggcgagacct gtccccatcc ctcatgctgg ctccttttct gggcttgcca   40920
agagccagca tcaggttgag gcaagctgga aagacttttc tggaaagcag cttgtttgca   40980
tggaagtcct cacaatgtcc tgtgtcttcc cagtaattcc acttctgaag tgaccagaca   41040
ttatcacggg tcttatttac catttccagt gttccaggca gggggacttg ccacagcaag   41100
tcacgaacct gcccaaatac agggctaagg agatattatg catcacaaaa cttgctctgc   41160
cattaaacat tttttcaaaga attttttgaag aatgtttaat ggcacaaaac gtttatttca   41220
atgtagcagt gttcaaagct ggatgtaaaa gaacacaccc caggagcctg ccgtgaatgt   41280
catgtgtgtt catctttgga catggacata catgggcagt gagtggtggt gaggccctgg   41340
aggacatcgg tgggatgcct ccatcctgcc cctctggaga caccatgtgt gccacgtgca   41400
ctcactggag ccctgtttag ctggtgccac ctggctcttc catccctgag attcaaacac   41460
agtgagattc cccacgccca actcagtgtt ctcccacaaa aaacctgagt cacacctgtg   41520
ttcactcgag ggacgcccgg gagccagggc tccacagttt attatgtgtt tttggctgag   41580
ttatgtgcag atctcatcag ggcagatgat gagtgcacaa acacgccgt gcgaggtttg   41640 gatacactca acatcactag ccaggtcctg gtggagtttg gtcatgcaga gtctggatgg   41700
catgtagcat ttggagtcca tggagtgagc acccagcccc ctcgggctgc agcgcatgcc   41760
ccaggcagga caaggaagcg ggaggaaggc aggaggctct ttggagcaag ctttgcagga   41820
gggggctggg tgtggggcag gcacctgtgt ctgacattcc cccctgtgtc tcagctatgc   41880
ccggacctcc atcagagcca gtctcacctt caaccgcggc ttcaaggctg gaggaacat   41940 gcgtcgcaaa ctctttgggg tcttgcggct gaagtgtcac agcctgtttc tggatttgca   42000
ggtgagcagg ctgatggtca gcacagagtt cagagttcag gaggtgtgtg cgcaagtatg   42060
tgtgtgtgtg tgtgcgcgcg tgcctgcaag gctgatggtg actggctgca cgtaagagtg   42120
cacatgtacg catatacacg tgagcacata catgtgtgca tgtgtgtaca tgaaggcatg   42180
gcagtgtgtg cacaggtgtg caagggcaca agtgtgtgca catgcgaatg cacacctgac   42240
atgcatgtgt gttcgtgcac agtcgtgtgg gcattcacgt gaggtgcatg cgtgtgggtg   42300
tgcagtgtga gtagcatgtg tgcacataac atgtattgag gggtcctcgt gttcaccccg   42360
ctaggtcctc agcaccagtg ccactcctta caggatgaga cggggtccca ggccttggtg   42420
ggctgaggct ctgaagctgc agccctgagg gcattgtccc atctgggcat ccgcgtccac   42480
tccctctcct gtgggcttct gtgtccactc cccctctcct gtgggcattt acatccactc   42540
cactccctct ctcctgtggg catccgcgtc cactcccccct ctctgtgggc atctgcgtcc   42600
acctcccctc tctgtgggca tttgcgtcca ctccctctcc tggttccttc ctgtcttggc   42660
cgagcctcgg gggcaggcag atgacacaga gtcttgactc gcccagggtg gttcgcagct   42720
gccgggtgag ggcaggccg gatttcactg ggaagaggga tagtttcttg tcaaaatgtt   42780
cctctttctt gttccatctg aatggatgat aaagcaaaaa gtaaaaactt aaaatcccag   42840
agaggtttct accgtttctc actctttctt ggcgactcta ggtgaacagc ctccagacgg   42900
tgtgcaccaa catctacaag atcctcctgc tgcaggcgta caggtgagcc gccaccaagg   42960
ggtgcaggcc cagcctccag ggaccctccg cgctctgctc acctctgacc cggggcttca   43020
ccttggaact cctgggtttt aggggcaagg aatgtcttac gttttcagtg gtgctgctgc   43080
ctgtgcacag ttctgttcgc gtggctctgt gcaaagcacc tgttctccat ctctgggtag   43140
tggtaggagc cggtgtggcc ccaggtgtcc ccactgtgcc tgtgcactgg ccgtgggacg   43200
tcatggaggc catcccaggg cagcaggggc atggggtaaa gagatgttta tggggagtct   43260
```

-continued

```
tagcagagga ggctgggaag gtgtctgaac agtagatggg agatcagatg cccggaggat    43320
ttggggtctc agcaaagagg gccgaggtgg gtgcaggtga gggtcgctgg ccccacccc    43380
gggaaggtgc agcagagctg tggctcccca cacagcccgg ccagcacctg tgctctgggc    43440
atggctgtgc tcctggaacg ttccctgtcc tggctggtca gggggtgccc ctgccaagaa    43500
tcgacaactt tatcacagag ggaagggcca atctgtggag gccacagggc cagcttctgc    43560
ctggagtcag ggcaggtggt ggcacaagcc tcggggctgt accaaagggc agtcgggcac    43620
cacaggcccg ggcctccacc tcaacaggcc tcccgagcca ctgggagctg aatgccagga    43680
ggccgaagcc ctcgcccat gagggctgag aaggagtgtg agcatttgtg ttacccaggg    43740
ccgaggctgc gcgaattacc gtgcacactt gatgtgaaat gaggtcgtcg tctatcgtgg    43800
aaacccagca agggctcacg ggagagtttt ccattacaag gtcgtaccat gaaaatggtt    43860
tttaacccga gtgcttgcgc cttcatgctc tggcagggag ggcagagcca cagctgcatg    43920
ttaccgcctt tgcaccagct ccagaggctt gggaccaggc tgtctcagtt ccagggtgcg    43980
tccggctcag accgccctcc tctctgcctt ctctctctgc ctcaaatctt ccctcgtttg    44040
catctccctg acgcgtgcct gggccctcgt gcaagctgct tgactccttt ccggaaaccc    44100
ttggggtgtg ctggatacag gtgccactga ggactggagg tgtctgacac tgtggttgac    44160
cccagggtcc agctggcgtg cttgggcct ccttgggcca tgatgaggtc agaggagttt    44220
tcccaggtga aaactcctgg gaaactccca gggccatgtg acctgccacc tgctcctccc    44280
atattcagct cagtcttgtc ctcatttccc caccagggtc tctagctccg aggagctccc    44340
gtagagggcc tgggctcagg gcagggcggc tgagtttccc cacccatgtg ggacccttg    44400
ggtagtcgct tgattgggta gccctgagga ggccgagatg cgatgggcca cgggccgttt    44460
ccaaacacag agtcaggcac gtggaaggcc caggaatccc cttccctcga ggcaggagtg    44520
ggagaacgga gagctgggcc ccgatttcac ggcagccagg ctgcagtggg cgaggctgtg    44580
gtggtccacg tggcgctggg ggcggggtct gattcaaatc cgctggggct cggccttcct    44640
ggcccgtgct ggccgcgcct ccacacgggc ttggggtgga cgccccgacc tctagcaggt    44700
ggctatttct ccctttggaa gagagcccct cacccatgct aggtgtttcc ctcctgggtc    44760
aggagcgtgg ccgtgtggca accccgggac cttaggctta tttatttgtt taaaaacatt    44820
ctgggcctgg cttccgttgt tgctaaatgg ggaaaagaca tcccacctca gcagagttac    44880
tgagaggctg aaaccggggt gctggcttga ctggtgtgat ctcaggtcat tccagaagtg    44940
gctcaggaag tcagtgagac caggtacatg gggggctcag gcagtgggtg agatgaggta    45000
cacgggggc tcaggcagtg ggtgaggcca ggtacatggg gggctcaggc actgggtgag    45060
atgaggtaca cggggggctc aggcagaggg tcagaccagg tacacggggg ctctgatcac    45120
acgcacatat gagcacatgt gcacatgtgc tgtttcatgg tagccaggtc tgtgcacacc    45180
tgccccaaag tccaggaag ctgagaggcc aaagatggag gctgacaggg ctggcgcggt    45240
ggctcacacc tgtagtccca gcactttggg aggccgaggc gagaggatcc cttgagccca    45300
ggagtttaag accagcctga gcaacatagt agaacccat ctctatgaaa aataaaaaca    45360
aaaattagct gaacatggtg gtgtgcgcct gtagttccaa tacttgggag gctgaagtgg    45420
gaggatcact tgagcccagg aggtggaagc tgcagtgagc tgagattgca ccactgtact    45480
gcagcctggg tgcagagtg agagcccatc tcaacaacaa caaagaagac tgacaaatgc    45540
agtttcttgg aaagaaacat ttagtaggaa cttaacctac acacagaagc caagtcggtg    45600
```

```
tctcggtgtc agtgagatga gatgatgggt cctcacacca tcaccccaga cccagggttt   45660
atgcaccaca ggggcgggtg gctcagaagg gatgcgcagg acgttgatat acgatgacat   45720
caaggttgtc tgacgaaggg caggattcat gataagtacc tgctggtaca caaggaacaa   45780
tggataaact ggaaacctta gaggccttcc cggaacaggg gctaatcaga agccagcatg   45840
gggggctggc atccaggatg gagctgcttc agcctccaca tgcgtgttca tacagatggt   45900
gcacagaaac gcagtgtacc tgtgcacaca cagacacgca gctactcgca cacacaagca   45960
cacacacaga catgcatgca tgcatccgtg tgtgtgcacc tgtgcccatg aggaaaccca   46020
tgcatgtgca ttcatgcacg cacacaggca ccggtgggcc catgcccaca cccacgagca   46080
ccgtctgatt aggaggcctt tcctctgacg ctgtccgcca tcctctcagg tttcacgcat   46140
gtgtgctgca gctcccattt catcagcaag tttggaagaa ccccacattt ttcctgcgcg   46200
tcatctctga cacggcctcc ctctgctact ccatcctgaa agccaagaac gcaggtatgt   46260
gcaggtgcct ggcctcagtg gcagcagtgc ctgcctgctg gtgttagtgt gtcaggagac   46320
tgagtgaatc tgggcttagg aagttcttac cccttttcgc atcaggaagt ggtttaaccc   46380
aaccactgtc aggctcgtct gcccgccctc tcgtggggtg agcagagcac ctgatggaag   46440
ggacaggagc tgtctgggag ctgccatcct tcccaccttg ctctgcctgg ggaagcgctg   46500
gggggcctgg tctctcctgt ttgccccatg gtgggatttg gggggcctgg cctctcctgt   46560
ttgccctgtg gtgggattgg gctgtctccc gtccatggca cttagggccc ttgtgcaaac   46620
ccaggccaag ggcttaggag gaggccaggc ccaggctacc ccacccctct caggagcaga   46680
ggccgcgtat caccacgaca gagccccgcg ccgtcctctg cttcccagtc accgtcctct   46740
gcccctggac actttgtcca gcatcaggga ggtttctgat ccgtctgaaa ttcaagccat   46800
gtcgaacctg cggtcctgag cttaacagct tctactttct gttctttctg tgttgtggaa   46860
atttcacctg gagaagccga agaaaacatt tctgtcgtga ctcctgcggt gcttgggtcg   46920
ggacagccag agatggagcc accccgcaga ccgtcgggtg tgggcagctt tccggtgtct   46980
cctgggaggg gagctgggct gggcctgtga ctcctcagcc tctgttttcc cccagggatg   47040
tcgctggggg ccaagggcgc cgccggccct ctgccctccg aggccgtgca gtggctgtgc   47100
caccaagcat tcctgctcaa gctgactcga caccgtgtca cctacgtgcc actcctgggg   47160
tcactcagga caggcaagtg tgggtggagg ccagtgcggg ccccacctgc caggggtca   47220 tccttgaacg ccctgtgtgg ggcgagcagc ctcagatgct gctgaagtgc agacgccccc   47280
gggcctgacc ctgggggcct ggagccacgc tggcagccct atgtgattaa acgctggtgt   47340
ccccaggcca cggagcctgg cagggtcccc aacttcttga acccctgctt cccatctcag   47400
gggcgatggc tccccacgct tgggagcctt ctgacccctg acctgtgtcc tctcacagcc   47460
tcttccctgg ctgctgccct gagctcctgg ggtcctgagc aagttctctc cccgccccgc   47520
cgctccagcg tcactgggct gcctgtctgc tcgccccggt ggaggggtgt ctgtcccttc   47580
actgaggttc ccaccagcca gggccacgag gtgcaggccc tgcctgcccg ccacccaca   47640 cgtcctagga gggttggagg atgccacctc tggcctcttc tggaacggag tctgattttg   47700
gccccgcagc ccagacgcag ctgagtcgga agctcccggg gacgacgctg actgccctgg   47760
aggccgcagc caacccggca ctgccctcag acttcaagac catcctggac tgatggccac   47820
ccgcccacag ccaggccgag agcagacacc agcagccctg tcacgcccgg gctctacgtcc  47880 cagggaggga gggcgggccc acacccaggc ccgcaccgct gggagtctga ggcctgagtg   47940
agtgtttggc cgaggcctgc atgtccggct gaaggctgag tgtccggctg aggcctgagc   48000
```

```
gagtgtccag ccaagggctg agtgtccagc acacctgccg tcttcacttc cccacaggct  48060
ggcgctcggc tccaccccag ggccagcttt tcctcaccag gagcccggct tccactcccc  48120
acataggaat agtccatccc cagattcgcc attgttcacc cctcgccctg ccctcctttg  48180
ccttccaccc ccaccatcca ggtggagacc ctgagaagga ccctgggagc tctgggaatt  48240
tggagtgacc aaaggtgtgc cctgtacaca ggcgaggacc ctgcacctgg atggggtcc   48300
ctgtgggtca aattgggggg aggtgctgtg ggagtaaaat actgaatata tgagtttttc  48360
agttttgaaa aaatctcat gtttgaatcc taatgtgcac tgcatagaca ccactgtatg   48420
caattacaga agcctgtgag tgaacggggt ggtggtcagt gcgggcccat ggcctggctg  48480
tgcatttacg gaagtctatg agtgaatggg gttgtggtca gtgcgggccc atggcctggc  48540
tgggcctggg aggtttctga tgctgtgagg caggagggga aggagggtag gggatagaca  48600
gtgggagccc ccaccctgga agacataaca gtaagtccag gcccgaaggg cagcagggat  48660
gctgggggcc cagcttgggc ggcggggatg atggagggcc tggccagggt ggcagggatg  48720
atgggggccc cagctggggt ggcaggggtg atgggggggg ctggtctggg tggcggggaa  48780
gatggggaag cctggctggg cccctcctc ccctgcctcc cacctgcagc cgtggatccg   48840
gatgtgcttc cctggtgcac atcctctggg ccatcagctt tcatggaggt gggggcagg   48900
ggcatgacac catcctgtat aaaatccagg attcctcctc ctgaacgccc caactcaggt  48960
tgaaagtcac attccgcctc tggccattct cttaagagta gaccaggatt ctgatctctg  49020
aagggtgggt agggtggggc agtggagggt gtggacacag gaggcttcag ggtggggctg  49080
gtgatgctct ctcatcctct tatcatctcc cagtctcatc tctcatcctc ttatcatctc  49140
ccagtctcat ctgtcttcct cttatctccc agtctcatct gtcatcctct taccatctcc  49200
cagtctcatc tcttatcctc ttatctccta gtctcatcca gacttacctc ccagggcggg  49260
tgccaggctc gcagtggagc tggacatacg tccttcctca ggcagaagga actggaagga  49320
ttgcagagaa caggagggc ggctcagagg gacgcagtct tggggtgaag aaacagcccc   49380
tcctcagaag ttggcttggg ccacacgaaa ccgagggccc tgcgtgagtg gctccagagc  49440
cttccagcag gtccctggtg gggccttatg gtatggccgg tcctactga gtgcaccttg   49500
gacagggctt ctggtttgag tgcagcccgg acgtgcctgg tgtcggggtg ggggcttatg  49560
gccactggat atggcgtcat ttattgctgc tgcttcagag aatgtctgag tgaccgagcc  49620
taatgtgtat ggtgggccca agtccacaga ctgtgtcgta aatgcactct ggtgcctgga  49680
gcccccgtat aggagctgtg aggaaggagg ggctcttggc agccggcctg ggggcgcctt  49740
tgccctgcaa actggaaggg agcggccccg ggcgccgtgg gcggacgacc tcaagtgaga  49800
ggttggacag aacagggcgg ggacttccca ggagcagagg ccgctgctca ggcacacctg  49860
ggtttgaatc acagaccaac aggtcaggcc attgttcagc tatccatctt ctacaaagct  49920
ccagattcct gtttctccgg gtgttttttg ttgaaatttt actcaggatt acttatattt  49980
tttgctaaag tattagaccc ttaaaaaagg tatttgcttt gatatggctt aactcactaa  50040
gcacctactt tatttgtctg tttttattta ttattattat tattattaga gatggtgtct  50100
actctgtcac ccaggttgtt agtgcagtgg cacagtcatg gctcgctgta gccgcaaacc  50160
cccaggctca gtgatcctc cggcctcagc ttcccagagt gctgggatta caggtgtgag   50220
ccactgccct tgcctggcac ttttaaaaac cactatgtaa ggtcaggtcc agtggcttcc  50280
acacctgtca tcccagtagt ttgggaagcc gaggcagaag gattgtctga ggccaggagt  50340
```

```
ttgagaccag catgggtaac atagggagac cccatctcta caaaaaatgc aaaaagttat    50400
ccgggcgtgg ggtccagcat ctgtagtccc agctgctcgg gaggctgagt gggaggatcg    50460
cttgagcccg ggaggtcatg gctgcagtga gctgtgattg taccatcgca ctccagcctg    50520
ggcaacagag tgagaccctg tctcaaaaaa aaaaaaaaa aaagaaggag aaggagaaga    50580
gaagaagaag gaagaaggaa agagaagaag aaggaagaag gaagaaagaa ggagaaggag    50640
gcctgctagg tgctaggtag actgtcaaat ctcagagcaa aatgaaaata acaaagtttt    50700
aaagggaaag aaaaacccca gctctttgga cttccttagg cctgaacttc atctcaagca    50760
gcttccttcc acagacaagc gtgtatggag cgagtgagtt caaagcagaa agggaggaga    50820
agcaggcaag ggtggaggct gtgggtgaca ccagccagga cccctgaaag ggagtggttg    50880 tttcctgcc tcagccccac gctcctgccg gtcctgcacc tgctgtaacc gtcgatgttg    50940
gtgccaggtg cccacctggg aaggatgctg tgcaggggc ttgccaaact ttggtgggtt    51000
tcagaagccc caggcacttg tggcaggcac aattacagcc cctcccccaaa gatgcccacg    51060 tccttctcct ggaacctgtg aatgtgtcac ccgcaaggca gaggctggtg aaggctgcag    51120
gtggaatcac ggctgccagt cagccgatct taaggtcatc ctggattatc tggtgggcct    51180
gatatggcca caagggtccc tagaagtgag agagggaggc aggggagagt cagagagggg    51240
acgtgagaag gaccactggc cactgctggc tttgagatgg aggaggggt ccccagccaa    51300 ggaatggggg cagccgctcc atgctggaaa agcaagcaat cctccccggt cctgagggca    51360
cacggccctg cccacgcctc gatttcaggc cagtgggacc tgtttcagct ttccggcctc    51420
cagagctgta agatgatgcg tttgtgttca gccactaagc tgcagtgatt cgtcacagca    51480
gcaaatggaa tagcagtaca gggaaatgaa tacagggaca gttctcagag tgactctcag    51540
cccacccctg gg                                                       51552
```

<210> SEQ ID NO 4
<211> LENGTH: 1132
<212> TYPE: PRT
<213> ORGANISM: Homo sapiens

<400> SEQUENCE: 4

```
Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160
```

```
Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro His Ala Ser Gly
            180                 185                 190

Pro Arg Arg Arg Leu Gly Cys Glu Arg Ala Trp Asn His Ser Val Arg
            195                 200                 205

Glu Ala Gly Val Pro Leu Gly Leu Pro Ala Pro Gly Ala Arg Arg Arg
        210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
                260                 265                 270

Val Ser Pro Ala Arg Pro Ala Glu Glu Ala Thr Ser Leu Glu Gly Ala
            275                 280                 285

Leu Ser Gly Thr Arg His Ser His Pro Ser Val Gly Arg Gln His His
        290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
                340                 345                 350

Ser Leu Thr Gly Ala Arg Arg Leu Val Glu Thr Ile Phe Leu Gly Ser
            355                 360                 365

Arg Pro Trp Met Pro Gly Thr Pro Arg Arg Leu Pro Arg Leu Pro Gln
        370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Glu Asp Thr Asp Pro Arg Arg Leu
        435                 440                 445

Val Gln Leu Leu Arg Gln His Ser Ser Pro Trp Gln Val Tyr Gly Phe
        450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Ile Leu Ala Lys Phe
        530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575
```

-continued

```
Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
            595                 600                 605

His Arg Glu Ala Arg Pro Ala Leu Leu Thr Ser Arg Leu Arg Phe Ile
            610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
            645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
            675                 680                 685

Ala Trp Arg Thr Phe Val Leu Arg Val Arg Ala Gln Asp Pro Pro Pro
            690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
            725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
            755                 760                 765

Leu Gln Pro Tyr Met Arg Gln Phe Val Ala His Leu Gln Glu Thr Ser
            770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
            805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
            835                 840                 845

Met Glu Asn Lys Leu Phe Ala Gly Ile Arg Arg Asp Gly Leu Leu Leu
850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
            885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
            915                 920                 925

Pro Trp Cys Gly Leu Leu Leu Asp Thr Arg Thr Leu Glu Val Gln Ser
            930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
            965                 970                 975

Val Leu Arg Leu Lys Cys His Ser Leu Phe Leu Asp Leu Gln Val Asn
            980                 985                 990

Ser Leu Gln Thr Val Cys Thr Asn  Ile Tyr Lys Ile Leu  Leu Leu Gln
```

```
                 995              1000               1005
Ala Tyr Arg Phe His Ala Cys Val Leu Gln Leu Pro Phe His Gln
   1010              1015              1020

Gln Val Trp Lys Asn Pro Thr Phe Phe Leu Arg Val Ile Ser Asp
   1025              1030              1035

Thr Ala Ser Leu Cys Tyr Ser Ile Leu Lys Ala Lys Asn Ala Gly
   1040              1045              1050

Met Ser Leu Gly Ala Lys Gly Ala Ala Gly Pro Leu Pro Ser Glu
   1055              1060              1065

Ala Val Gln Trp Leu Cys His Gln Ala Phe Leu Leu Lys Leu Thr
   1070              1075              1080

Arg His Arg Val Thr Tyr Val Pro Leu Leu Gly Ser Leu Arg Thr
   1085              1090              1095

Ala Gln Thr Gln Leu Ser Arg Lys Leu Pro Gly Thr Thr Leu Thr
   1100              1105              1110

Ala Leu Glu Ala Ala Ala Asn Pro Ala Leu Pro Ser Asp Phe Lys
   1115              1120              1125

Thr Ile Leu Asp
   1130

<210> SEQ ID NO 5
<211> LENGTH: 6492
<212> TYPE: DNA
<213> ORGANISM: Homo sapiens

<400> SEQUENCE: 5
tttctgtgaa gcagaagtct gggaatcgat ctggaaatcc tcctaatttt tactccctct    60
ccccgcgact cctgattcat tgggaagttt caaatcagct ataactggag agtgctgaag   120
attgatggga tcgttgcctt atgcatttgt tttggtttta caaaaggaa acttgacaga    180 ggatcatgct gtacttaaaa aatacaacat cacagaggaa gtagactgat attaacaata   240
cttactaata ataacgtgcc tcatgaaata aagatccgaa aggaattgga ataaaaattt   300
cctgcatctc atgccaaggg ggaaacacca gaatcaagtg ttccgcgtga ttgaagacac   360
cccctcgtcc aagaatgcaa agcacatcca ataaatagc tggattataa ctcctcttct    420
ttctctgggg gccgtggggt gggagctggg gcgagaggtg ccgttggccc ccgttgcttt    480
tcctctggga aggatggcgc acgctgggag aacagggtac gataaccggg agatagtgat   540
gaagtacatc cattataagc tgtcgcagag gggctacgag tgggatgcgg gagatgtggg   600
cgccgcgccc ccgggggccg ccccccgcacc gggcatcttc tcctcccagc ccgggcacac   660
gccccatcca gccgcatccc gggacccggt cgccaggacc tcgccgctgc agaccccggc   720 tgccccggc gccgccgcgg ggcctgcgct cagcccggtg ccacctgtgg tccacctgac    780
cctccgccag gccggcgacg acttctcccg ccgctaccgc gcgacttcg ccgagatgtc    840 cagccagctg cacctgacgc ccttcaccgc gcggggacgc tttgccacgg tggtggagga   900
gctcttcagg gacggggtga actggggagg gattgtggcc ttctttgagt cggtggggt    960 catgtgtgtg gagagcgtca accgggagat gtcgcccctg gtggacaaca tcgccctgtg   1020
gatgactgag tacctgaacc ggcacctgca cacctggatc caggataacg gaggctggga   1080
tgcctttgtg gaactgtacg gcccagcat gcggcctctg tttgatttct cctggctgtc   1140
tctgaagact ctgctcagtt tggccctggt gggagcttgc atcaccctgg gtgcctatct   1200
gggccacaag tgaagtcaac atgcctgccc caaacaaata tgcaaaggt tcactaaagc    1260
```

-continued

```
agtagaaata atatgcattg tcagtgatgt accatgaaac aaagctgcag gctgtttaag    1320
aaaaaataac acacatataa acatcacaca cacagacaga cacacacaca cacaacaatt    1380
aacagtcttc aggcaaaacg tcgaatcagc tatttactgc caaagggaaa tatcatttat    1440
tttttacatt attaagaaaa aaagatttat ttatttaaga cagtcccatc aaaactcctg    1500
tctttggaaa tccgaccact aattgccaag caccgcttcg tgtggctcca cctggatgtt    1560
ctgtgcctgt aaacatagat tcgctttcca tgttgttggc cggatcacca tctgaagagc    1620
agacggatgg aaaaaggacc tgatcattgg ggaagctggc tttctggctg ctggaggctg    1680
gggagaaggt gttcattcac ttgcatttct ttgccctggg ggctgtgata ttaacagagg    1740
gagggttcct gtgggggggaa gtccatgcct ccctggcctg aagaagagac tctttgcata    1800
tgactcacat gatgcatacc tggtgggagg aaaagagttg ggaacttcag atggacctag    1860
tacccactga gatttccacg ccgaaggaca gcgatgggaa aaatgccctt aaatcatagg    1920
aaagtatttt tttaagctac caattgtgcc gagaaaagca ttttagcaat ttatacaata    1980
tcatccagta ccttaagccc tgattgtgta tattcatata ttttggatac gcacccccca    2040
actcccaata ctggctctgt ctgagtaaga aacagaatcc tctggaactt gaggaagtga    2100
acatttcggt gacttccgca tcaggaaggc tagagttacc cagagcatca ggccgccaca    2160
agtgcctgct tttaggagac cgaagtccgc agaacctgcc tgtgtcccag cttggaggcc    2220
tggtcctgga actgagccgg ggccctcact ggcctcctcc agggatgatc aacagggcag    2280
tgtggtctcc gaatgtctgg aagctgatgg agctcagaat ccactgtca agaaagagca    2340 gtagaggggt gtggctgggc ctgtcaccct ggggccctcc aggtaggccc gttttcacgt    2400
ggagcatggg agccacgacc cttcttaaga catgtatcac tgtagaggga aggaacagag    2460
gccctgggcc cttcctatca gaaggacatg gtgaaggctg ggaacgtgag gagaggcaat    2520
ggccacggcc catttttggct gtagcacatg gcacgttggc tgtgtggcct tggcccacct    2580
gtgagtttaa agcaaggctt taaatgactt tggagagggt cacaaatcct aaaagaagca    2640
ttgaagtgag gtgtcatgga ttaattgacc cctgtctatg gaattacatg taaaacatta    2700
tcttgtcact gtagtttggt tttatttgaa aacctgacaa aaaaaaagtt ccaggtgtgg    2760
aatatggggg ttatctgtac atcctggggc attaaaaaaa aaatcaatgg tggggaacta    2820
taaagaagta acaaaagaag tgacatcttc agcaaataaa ctaggaaatt tttttttctt    2880
ccagtttaga atcagccttg aaacattgat ggaataactc tgtggcatta ttgcattata    2940
taccatttat ctgtattaac tttggaatgt actctgttca atgtttaatg ctgtggttga    3000
tatttcgaaa gctgctttaa aaaaatacat gcatctcagc gttttttttgt ttttaattgt    3060 atttagttat ggcctataca ctatttgtga gcaaaggtga tcgttttctg tttgagattt    3120
ttatctcttg attcttcaaa agcattctga gaaggtgaga taagccctga gtctcagcta    3180
cctaagaaaa acctggatgt cactggccac tgaggagctt tgtttcaacc aagtcatgtg    3240
catttccacg tcaacagaat tgtttattgt gacagttata tctgttgtcc ctttgacctt    3300
gtttcttgaa ggtttcctcg tccctgggca attccgcatt taattcatgg tattcaggat    3360
tacatgcatg tttggttaaa cccatgagat tcattcagtt aaaaatccag atggcaaatg    3420
accagcagat tcaaatctat ggtggtttga cctttagaga gttgctttac gtggcctgtt    3480
tcaacacaga cccacccaga gccctcctgc cctccttccg cggggctttt ctcatggctg    3540
tccttcaggg tcttcctgaa atgcagtggt gcttacgctc caccaagaaa gcaggaaacc    3600
tgtggtatga agccagacct ccccggcggg cctcaggaa cagaatgatc agacctttga    3660
```

```
atgattctaa tttttaagca aaatattatt ttatgaaagg tttacattgt caaagtgatg    3720
aatatggaat atccaatcct gtgctgctat cctgccaaaa tcattttaat ggagtcagtt    3780
tgcagtatgc tccacgtggt aagatcctcc aagctgcttt agaagtaaca atgaagaacg    3840
tggacgtttt taatataaag cctgttttgt cttttgttgt tgttcaaacg ggattcacag    3900
agtatttgaa aaatgtatat atattaagag gtcacggggg ctaattgctg gctggctgcc    3960
ttttgctgtg gggttttgtt acctggtttt aataacagta aatgtgccca gcctcttggc    4020
cccagaactg tacagtattg tggctgcact tgctctaaga gtagttgatg ttgcattttc    4080
cttattgtta aaaacatgtt agaagcaatg aatgtatata aaagcctcaa ctagtcattt    4140
ttttctcctc ttcttttttt tcattatatc taattatttt gcagttgggc aacagagaac    4200
catccctatt ttgtattgaa gagggattca catctgcatc ttaactgctc tttatgaatg    4260
aaaaaacagt cctctgtatg tactcctctt tacactggcc agggtcagag ttaaatagag    4320
tatatgcact ttccaaattg gggacaaggg ctctaaaaaa agcccccaaaa ggagaagaac    4380 atctgagaac ctcctcggcc ctcccagtcc ctcgctgcac aaatactccg caagagaggc    4440
cagaatgaca gctgacaggg tctatggcca tcgggtcgtc tccgaagatt tggcaggggc    4500
agaaaactct ggcaggctta agatttggaa taaagtcaca gaattaagga agcacctcaa    4560
tttagttcaa acaagacgcc aacattctct ccacagctca cttacctctc tgtgttcaga    4620
tgtggccttc catttatatg tgatctttgt tttattagta aatgcttatc atctaaagat    4680
gtagctctgg cccagtggga aaaattagga agtgattata aatcgagagg agttataata    4740
atcaagatta aatgtaaata atcagggcaa tcccaacaca tgtctagctt tcacctccag    4800
gatctattga gtgaacagaa ttgcaaatag tctctatttg taattgaact tatcctaaaa    4860
caaatagttt ataaatgtga acttaaactc taattaattc caactgtact tttaaggcag    4920
tggctgtttt tagactttct tatcacttat agttagtaat gtacacctac tctatcagag    4980
aaaaacagga aaggctcgaa atacaagcca ttctaaggaa attagggagt cagttgaaat    5040
tctattctga tcttattctg tggtgtcttt tgcagcccag acaaatgtgg ttacacactt    5100
tttaagaaat acaattctac attgtcaagc ttatgaaggt tccaatcaga tctttattgt    5160 tattcaatttt ggatctttca gggatttttt ttttaaatta ttatgggaca aaggacattt    5220
gttggagggg tgggagggag gaagaatttt taaatgtaaa acattcccaa gtttggatca    5280
gggagttgga agttttcaga ataaccagaa ctaagggtat gaaggacctg tattggggtc    5340
gatgtgatgc ctctgcgaag aaccttgtgt gacaaatgag aaacattttg aagtttgtgg    5400
tacgaccttt agattccaga gacatcagca tggctcaaag tgcagctccg tttggcagtg    5460
caatggtata aatttcaagc tggatatgtc taatgggtat ttaaacaata aatgtgcagt    5520
tttaactaac aggatattta atgacaacct tctggttggt agggacatct gtttctaaat    5580
gtttattatg tacaatacag aaaaaaattt tataaaatta agcaatgtga aactgaattg    5640
gagagtgata atacaagtcc tttagtctta cccagtgaat cattctgttc catgtctttg    5700
gacaaccatg accttggaca atcatgaaat atgcatctca ctggatgcaa agaaaatcag    5760
atggagcatg aatggtactg taccggttca tctggactgc cccagaaaaa taacttcaag    5820
caaacatcct atcaacaaca aggttgttct gcataccaag ctgagcacag aagatgggaa    5880
cactggtgga ggatggaaag gctcgctcaa tcaagaaaat tctgagacta ttaataaata    5940
agactgtagt gtagatactg agtaaatcca tgcacctaaa cctttggaa aatctgccgt    6000
```

-continued

```
gggccctcca gatagctcat tcattaagt ttttccctcc aaggtagaat ttgcaagagt    6060
gacagtggat tgcatttctt ttggggaagc tttcttttgg tggttttgtt tattataccctt  6120 tcttaagttt tcaaccaagg tttgcttttg ttttgagtta ctggggttat ttttgttttta   6180 aataaaaata agtgtacaat aagtgttttt gtattgaaag cttttgttat caagattttc   6240
atacttttac cttccatggc tcttttttaag attgatactt ttaagaggtg gctgatattc   6300
tgcaacactg tacacataaa aaatacggta aggatacttt acatggttaa ggtaaagtaa    6360
gtctccagtt ggccaccatt agctataatg gcactttgtt tgtgttgttg gaaaaagtca   6420
cattgccatt aaactttcct tgtctgtcta gttaatattg tgaagaaaaa taaagtacag   6480
tgtgagatac tg                                                        6492
```

<210> SEQ ID NO 6
<211> LENGTH: 239
<212> TYPE: PRT
<213> ORGANISM: Homo sapiens

<400> SEQUENCE: 6

```
Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235
```

<210> SEQ ID NO 7
<211> LENGTH: 1207
<212> TYPE: DNA
<213> ORGANISM: Homo sapiens

<400> SEQUENCE: 7

```
tttctgtgaa gcagaagtct gggaatcgat ctggaaatcc tcctaatttt tactccctct      60
ccccgcgact cctgattcat tgggaagttt caaatcagct ataactggag agtgctgaag     120
attgatggga tcgttgcctt atgcatttgt tttggtttta caaaaaggaa acttgacaga     180
ggatcatgct gtacttaaaa aatcaacat cacagaggaa gtagactgat attaacaata     240
cttactaata ataacgtgcc tcatgaaata aagatccgaa aggaattgga ataaaattt      300 cctgcatctc atgccaaggg ggaaacacca gaatcaagtg ttccgcgtga ttgaagacac     360
cccctcgtcc aagaatgcaa agcacatcca ataaaatagc tggattataa ctcctcttct     420
ttctctgggg gccgtggggt gggagctggg gcgagaggtg ccgttggccc ccgttgcttt     480
tcctctggga aggatggcgc acgctgggag aacagggtac gataaccggg agatagtgat     540
gaagtacatc cattataagc tgtcgcagag gggctacgag tgggatgcgg agatgtggg     600 cgccgcgccc ccgggggccg ccccgcacc gggcatcttc tcctcccagc ccgggcacac     660
gccccatcca gccgcatccc gggacccggt cgccaggacc tcgccgctgc agaccccggc     720
tgcccccggc gccgccgcgg ggcctgcgct cagcccggtg ccacctgtgg tccacctgac     780
cctccgccag gccggcgacg acttctcccg ccgctaccgc cgcgacttcg ccgagatgtc     840
cagccagctg cacctgacgc ccttcaccgc gcggggacgc tttgccacgg tggtggagga     900
gctcttcagg gacggggtga actggggag gattgtggcc ttctttgagt tcggtggggt     960
catgtgtgtg gagagcgtca accgggagat gtcgcccctg gtggacaaca tcgccctgtg    1020
gatgactgag tacctgaacc ggcacctgca cacctggatc caggataacg gaggctgggt    1080
aggtgcactt ggtgatgtga gtctgggctg aggccacagg tccagatgc gggggttgga    1140 gtgcgggtgg gctcctgggg caatgggagg ctgtggagcc ggcgaaataa aatcagagtt    1200
gttgcta                                                             1207
```

<210> SEQ ID NO 8
<211> LENGTH: 205
<212> TYPE: PRT
<213> ORGANISM: Homo sapiens

<400> SEQUENCE: 8

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

| | | | | | |
|---|---|---|---|---|---|
|Ser|Val Asn Arg Glu|Met Ser Pro Leu Val|Asp Asn Ile Ala|Leu Trp| |
| |165| 170 | 175| | |

Met Thr Glu Tyr Leu Asn Arg His Leu His Thr Trp Ile Gln Asp Asn
           180                 185                 190

Gly Gly Trp Val Gly Ala Leu Gly Asp Val Ser Leu Gly
        195                 200               205

<210> SEQ ID NO 9
<211> LENGTH: 2594
<212> TYPE: DNA
<213> ORGANISM: Human immunodeficiency virus

<400> SEQUENCE: 9

| | | | | |
|---|---|---|---|---|
|atggagccag|tagatcctag|actagagccc|tggaagcatc|caggaagtca gcctaaaact|60|
|gcttgtacca|attgctattg|taaaaagtgt|tgctttcatt|gccaagtttg tttcataaca|120|
|aaagccttag|gcatctccta|tggcaggaag|aagcggagac|agcgacgaag agctcatcag|180|
|aacagtcaga|ctcatcaagc|ttctctatca|aagcagtaag|tagtacatgt aatgcaacct|240|
|ataccaatag|tagcaatagt|agcattagta|gtagcaataa|taatagcaat agttgtgtgg|300|
|tccatagtaa|tcatagaata|taggaaaata|ttaagacaaa|gaaaaataga caggttaatt|360|
|gatagactaa|tagaaagagc|agaagacagt|ggcaatgaga|gtgaaggaga aatatcagca|420|
|cttgtggaga|tgggggtgga|gatggggcac|catgctcctt|gggatgttga tgatctgtag|480|
|tgctacagaa|aaattgtggg|tcacagtcta|ttatgggta|cctgtgtgga aggaagcaac|540|
|caccactcta|ttttgtgcat|cagatgctaa|agcatatgat|acagaggtac ataatgtttg|600|
|ggccacacat|gcctgtgtac|ccacagaccc|caacccacaa|gaagtagtat tggtaaatgt|660|
|gacagaaaat|tttaacatgt|ggaaaaatga|catggtagaa|cagatgcatg aggatataat|720|
|cagtttatgg|gatcaaagcc|taaagccatg|tgtaaaatta|accccactct gtgttagttt|780|
|aaagtgcact|gatttgaaga|atgatactaa|taccaatagt|agtagcggga gaatgataat|840|
|ggagaaagga|gagataaaaa|actgctcttt|caatatcagc|acaagcataa gaggtaaggt|900|
|gcagaaagaa|tatgcatttt|tttataaact|tgatataata|ccaatagata atgatactac|960|
|cagctataag|ttgacaagtt|gtaacacctc|agtcattaca|caggcctgtc caaaggtatc|1020|
|ctttgagcca|attcccatac|attattgtgc|cccggctggt|tttgcgattc taaaatgtaa|1080|
|taataagacg|ttcaatggaa|caggaccatg|tacaaatgtc|agcacagtac aatgtacaca|1140|
|tggaattagg|ccagtagtat|caactcaact|gctgttaaat|ggcagtctag cagaagaaga|1200|
|ggtagtaatt|agatctgtca|atttcacgga|caatgctaaa|accataatag tacagctgaa|1260|
|cacatctgta|gaaattaatt|gtacaagacc|caacaacaat|acaagaaaaa gaatccgtat|1320|
|ccagagagga|ccagggagag|catttgttac|aataggaaaa|ataggaaata tgagacaagc|1380|
|acattgtaac|attagtagag|caaaatggaa|taacacttta|aaacagatag ctagcaaatt|1440|
|aagagaacaa|tttggaaata|taaaacaat|aatctttaag|caatcctcag gaggggaccc|1500|
|agaaattgta|acgcacagtt|ttaattgtgg|aggggaattt|ttctactgta attcaacaca|1560|
|actgtttaat|agtacttggt|ttaatagtac|ttggagtact|gaagggtcaa ataacactga|1620|
|aggaagtgac|acaatcaccc|tcccatgcag|aataaaacaa|attataaaca tgtggcagaa|1680|
|agtaggaaaa|gcaatgtatg|cccctcccat|cagtggacaa|attagatgtt catcaaatat|1740|
|tacagggctg|ctattaacaa|gagatggtgg|taatagcaac|aatgagtccg agatcttcag|1800|
|acctggagga|ggagatatga|gggacaattg|gagaagtgaa|ttatataaat ataaagtagt|1860|

```
aaaaattgaa ccattaggag tagcacccac caaggcaaag agaagagtgg tgcagagaga    1920
aaaaagagca gtgggaatag gagctttgtt ccttgggttc ttgggagcag caggaagcac    1980
tatgggcgca gcctcaatga cgctgacggt acaggccaga caattattgt ctggtatagt    2040
gcagcagcag aacaatttgc tgagggctat tgaggcgcaa cagcatctgt tgcaactcac    2100
agtctggggc atcaagcagc tccaggcaag aatcctggct gtggaaagat acctaaagga    2160
tcaacagctc ctggggattt ggggttgctc tggaaaactc atttgcacca ctgctgtgcc    2220
ttggaatgct agttggagta ataaatctct ggaacagatt tggaatcaca cgacctggat    2280
ggagtgggac agagaaatta acaattacac aagcttaata cactccttaa ttgaagaatc    2340
gcaaaaccag caagaaaaga atgaacaaga attattggaa ttagataaat gggcaagttt    2400
gtggaattgg tttaacataa caaattggct gtggtatata aaattattca taatgatagt    2460
aggaggcttg gtaggttaa gaatagtttt tgctgtactt tctatagtga atagagttag    2520
gcagggatat tcaccattat cgtttcagac ccacctccca accccgaggg gacccgacag    2580
gcccgaagga atag                                                     2594
```

<210> SEQ ID NO 10
<211> LENGTH: 86
<212> TYPE: PRT
<213> ORGANISM: Human immunodeficiency virus

<400> SEQUENCE: 10

```
Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Arg Ala His Gln Asn Ser Gln Thr
    50                  55                  60

His Gln Ala Ser Leu Ser Lys Gln Pro Thr Ser Gln Pro Arg Gly Asp
65                  70                  75                  80

Pro Thr Gly Pro Lys Glu
                85
```

<210> SEQ ID NO 11
<211> LENGTH: 2397
<212> TYPE: DNA
<213> ORGANISM: Homo sapiens

<400> SEQUENCE: 11

```
ctgtcccgca agcgccggcg gcagcatggc cagctctggt tccctgaggg cttcaaagtg      60
tctgaggcca gcaagaagaa gcggcgggag cccctcggcg aggactccgt gggcctcaag     120
cccctgaaga acgcttcaga cggtgccctc atggacgaca accagaatga gtgggggac      180 gaggacctgg agaccaagaa gttccggttc gaggagcccg tggttctgcc tgacctggac     240
gaccagacag accaccggca gtggactcag cagcacctgg atgccgctga cctgcgcatg     300
tctgccatgg cccccacacc gccccagggt gaggttgacg ccgactgcat ggacgtcaat     360
gtccgcgggc ctgatggctt cacccgctc atgatcgcct cctgcagcgg ggcggcctg      420 gagacgggca acagcgagga agaggaggac gcgccggccg tcatctccga cttcatctac     480
cagggcgcca gcctgcacaa ccagacagac cgcacgggcg agaccgcctt gcacctggcc     540
```

```
gcccgctact cacgctctga tgccgccaag cgcctgctgg aggccagcgc agatgccaac    600
atccaggaca catgggccg cacccccgctg catgcggctg tgtctgccga cgcacaaggt    660
gtcttccaga tcctgatccg gaaccgagcc acagacctgg atgcccgcat gcatgatggc    720
acgacgccac tgatcctggc tgcccgcctg gccgtggagg gcatgctgga ggacctcatc    780
aactcacacg ccgacgtcaa cgccgtagat gacctgggca agtccgccct gcactgggcc    840
gccgccgtga acaatgtgga tgccgcagtt gtgctcctga agaacggggc taacaaagat    900
atgcagaaca cagggagga cacccctg tttctggccg cccgggaggg cagctacgag       960
accgccaagg tgctgctgga ccactttgcc aaccgggaca tcacggatca tatggaccgc   1020
ctgccgcgcg acatcgcaca ggagcgcatg catcacgaca tcgtgaggct gctggacgag   1080
tacaacctgg tgcgcagccc gcagctgcac ggagccccgc tggggggcac gcccaccctg   1140
tcgcccccgc tctgctcgcc caacggctac ctgggcagcc tcaagcccgg cgtgcagggc   1200
aagaaggtcc gcaagcccag cagcaaaggc ctggcctgtg gaagcaagga ggccaaggac   1260
ctcaaggcac ggaggaagaa gtcccaggac ggcaagggct gcctgctgga cagctccggc   1320
atgctctcgc ccgtggactc cctggagtca ccccatggct acctgtcaga cgtggcctcg   1380
ccgccactgc tgccctcccc gttccagcag tctccgtccg tgcccctcaa ccacctgcct   1440
gggatgccg  acaccacct gggcatcggg cacctgaacg tggcggccaa gcccgagatg   1500
gcggcgctgg tgggggcgg ccggctggcc tttgagactg gccacctcg tctctcccac   1560
ctgcctgtgg cctctggcac cagcaccgtc ctgggctcca gcagcggagg ggccctgaat   1620
ttcactgtgg gcgggtccac cagtttgaat ggtcaatgcg agtggctgtc ccggctgcag   1680
agcggcatgg tgccgaacca atacaaccct ctgcgggga gtgtggcacc aggccccctg   1740
agcacacagg cccctccct gcagcatggc atggtaggcc cgctgcacag tagccttgct   1800
gccagcgccc tgtcccagat gatgagctac cagggcctgc ccagcacccg gctggccacc   1860
cagcctcacc tggtgcagac ccagcaggtg cagcccacaaa acttacagat gcagcagcag   1920
aacctgcagc cagcaaacat ccagcagcag caaagcctgc agccgccacc accaccacca   1980
cagccgcacc ttggcgtgag ctcagcagcc agcggccacc tgggccggag cttcctgagt   2040
ggagagccga gccaggcaga cgtgcagcca ctgggcccca gcagcctggc ggtgcacact   2100
attctgcccc aggagagccc cgccctgccc acgtcgctgc catcctcgct ggtcccaccc   2160
gtgaccgcag cccagttcct gacgcccccc tcgcagcaca gctactcctc gcctgtggac   2220
aacaccccca gccaccagct acaggtgcct gagcacccct cctcacccc  gtccctgag   2280
tcccctgacc agtggtccag ctcgtccccg cattccaacg tctccgactg gtccgagggc   2340
gtctccagcc ctcccaccag catgcagtcc cagatcgccc gcattccgga ggccttc      2397
```

<210> SEQ ID NO 12
<211> LENGTH: 799
<212> TYPE: PRT
<213> ORGANISM: Homo sapiens

<400> SEQUENCE: 12

```
Leu Ser Arg Lys Arg Arg Arg Gln His Gly Gln Leu Trp Phe Pro Glu
1               5                   10                  15

Gly Phe Lys Val Ser Glu Ala Ser Lys Lys Arg Arg Glu Pro Leu
            20                  25                  30

Gly Glu Asp Ser Val Gly Leu Lys Pro Leu Lys Asn Ala Ser Asp Gly
        35                  40                  45
```

Ala Leu Met Asp Asp Asn Gln Asn Glu Trp Gly Asp Glu Asp Leu Glu
    50                  55                  60

Thr Lys Lys Phe Arg Phe Glu Glu Pro Val Val Leu Pro Asp Leu Asp
 65                  70                  75                  80

Asp Gln Thr Asp His Arg Gln Trp Thr Gln Gln His Leu Asp Ala Ala
                 85                  90                  95

Asp Leu Arg Met Ser Ala Met Ala Pro Thr Pro Gln Gly Glu Val
                100                 105                 110

Asp Ala Asp Cys Met Asp Val Asn Val Arg Gly Pro Asp Gly Phe Thr
                115                 120                 125

Pro Leu Met Ile Ala Ser Cys Ser Gly Gly Leu Glu Thr Gly Asn
        130                 135                 140

Ser Glu Glu Glu Glu Asp Ala Pro Ala Val Ile Ser Asp Phe Ile Tyr
145                 150                 155                 160

Gln Gly Ala Ser Leu His Asn Gln Thr Asp Arg Thr Gly Glu Thr Ala
                165                 170                 175

Leu His Leu Ala Ala Arg Tyr Ser Arg Ser Asp Ala Ala Lys Arg Leu
        180                 185                 190

Leu Glu Ala Ser Ala Asp Ala Asn Ile Gln Asp Asn Met Gly Arg Thr
        195                 200                 205

Pro Leu His Ala Ala Val Ser Ala Asp Ala Gln Gly Val Phe Gln Ile
        210                 215                 220

Leu Ile Arg Asn Arg Ala Thr Asp Leu Asp Ala Arg Met His Asp Gly
225                 230                 235                 240

Thr Thr Pro Leu Ile Leu Ala Ala Arg Leu Ala Val Glu Gly Met Leu
                245                 250                 255

Glu Asp Leu Ile Asn Ser His Ala Asp Val Asn Ala Val Asp Asp Leu
            260                 265                 270

Gly Lys Ser Ala Leu His Trp Ala Ala Ala Val Asn Asn Val Asp Ala
        275                 280                 285

Ala Val Val Leu Leu Lys Asn Gly Ala Asn Lys Asp Met Gln Asn Asn
        290                 295                 300

Arg Glu Glu Thr Pro Leu Phe Leu Ala Ala Arg Glu Gly Ser Tyr Glu
305                 310                 315                 320

Thr Ala Lys Val Leu Leu Asp His Phe Ala Asn Arg Asp Ile Thr Asp
                325                 330                 335

His Met Asp Arg Leu Pro Arg Asp Ile Ala Gln Glu Arg Met His His
                340                 345                 350

Asp Ile Val Arg Leu Leu Asp Glu Tyr Asn Leu Val Arg Ser Pro Gln
            355                 360                 365

Leu His Gly Ala Pro Leu Gly Gly Thr Pro Thr Leu Ser Pro Pro Leu
        370                 375                 380

Cys Ser Pro Asn Gly Tyr Leu Gly Ser Leu Lys Pro Gly Val Gln Gly
385                 390                 395                 400

Lys Lys Val Arg Lys Pro Ser Ser Lys Gly Leu Ala Cys Gly Ser Lys
                405                 410                 415

Glu Ala Lys Asp Leu Lys Ala Arg Arg Lys Lys Ser Gln Asp Gly Lys
                420                 425                 430

Gly Cys Leu Leu Asp Ser Ser Gly Met Leu Ser Pro Val Asp Ser Leu
        435                 440                 445

Glu Ser Pro His Gly Tyr Leu Ser Asp Val Ala Ser Pro Pro Leu Leu
450                 455                 460

Pro Ser Pro Phe Gln Gln Ser Pro Ser Val Pro Leu Asn His Leu Pro

```
                465                 470                 475                 480
Gly Met Pro Asp Thr His Leu Gly Ile Gly His Leu Asn Val Ala Ala
                            485                 490                 495

Lys Pro Glu Met Ala Ala Leu Gly Gly Gly Arg Leu Ala Phe Glu
                500                 505                 510

Thr Gly Pro Pro Arg Leu Ser His Leu Pro Val Ala Ser Gly Thr Ser
                    515                 520                 525

Thr Val Leu Gly Ser Ser Gly Gly Ala Leu Asn Phe Thr Val Gly
            530                 535                 540

Gly Ser Thr Ser Leu Asn Gly Gln Cys Glu Trp Leu Ser Arg Leu Gln
545                 550                 555                 560

Ser Gly Met Val Pro Asn Gln Tyr Asn Pro Leu Arg Gly Ser Val Ala
                    565                 570                 575

Pro Gly Pro Leu Ser Thr Gln Ala Pro Ser Leu Gln His Gly Met Val
                580                 585                 590

Gly Pro Leu His Ser Ser Leu Ala Ala Ser Ala Leu Ser Gln Met Met
            595                 600                 605

Ser Tyr Gln Gly Leu Pro Ser Thr Arg Leu Ala Thr Gln Pro His Leu
    610                 615                 620

Val Gln Thr Gln Gln Val Gln Pro Gln Asn Leu Gln Met Gln Gln
625                 630                 635                 640

Asn Leu Gln Pro Ala Asn Ile Gln Gln Gln Ser Leu Gln Pro Pro
                    645                 650                 655

Pro Pro Pro Pro Gln Pro His Leu Gly Val Ser Ser Ala Ala Ser Gly
                660                 665                 670

His Leu Gly Arg Ser Phe Leu Ser Gly Glu Pro Ser Gln Ala Asp Val
            675                 680                 685

Gln Pro Leu Gly Pro Ser Ser Leu Ala Val His Thr Ile Leu Pro Gln
    690                 695                 700

Glu Ser Pro Ala Leu Pro Thr Ser Leu Pro Ser Ser Leu Val Pro Pro
705                 710                 715                 720

Val Thr Ala Ala Gln Phe Leu Thr Pro Pro Ser Gln His Ser Tyr Ser
                    725                 730                 735

Ser Pro Val Asp Asn Thr Pro Ser His Gln Leu Gln Val Pro Glu His
                740                 745                 750

Pro Phe Leu Thr Pro Ser Pro Glu Ser Pro Asp Gln Trp Ser Ser Ser
            755                 760                 765

Ser Pro His Ser Asn Val Ser Asp Trp Ser Glu Gly Val Ser Ser Pro
770                 775                 780

Pro Thr Ser Met Gln Ser Gln Ile Ala Arg Ile Pro Glu Ala Phe
785                 790                 795
```

<210> SEQ ID NO 13
<211> LENGTH: 814
<212> TYPE: DNA
<213> ORGANISM: Homo sapiens

<400> SEQUENCE: 13

```
ccttcacctg cctctgccgc ccaggctaca cgggccacca ctgcgagacc aacatcaacg    60
agtgctccag ccagccctgc cgcctacggg gcacctgcca ggacccggac aacgcctacc   120
tctgcttctg cctgaagggg accacaggac ccaactgcga gatcaacctg atgactgtg    180 ccagcagccc ctgcgactcg ggcacctgtc tggacaagat cgatggctac gagtgtgcct   240
gtgagccggg ctacacaggg agcatgtgta acagcaacat cgatgagtgt gcgggcaacc   300
```

```
cctgccacaa cggggcacc tgcgaggacg gcatcaatgg cttcacctgc cgctgccccg    360
agggctacca cgaccccacc tgcctgtctg aggtcaatga gtgcaacagc aaccccctgcg  420
tccacgggc ctgccgggac agcctcaacg ggtacaagtg cgactgtgac cctgggtgga    480
gtgggaccaa ctgtgacatc aacaacaacg agtgtgaatc caacccttgt gtcaacggcg   540
gcacctgcaa agacatgacc agtggcatcg tgtgcacctg ccgggagggc ttcagcggtc   600
ccaactgcca gaccaacatc aacgagtgtg cgtccaaccc atgtctgaac aagggcacgt   660
gtattgacga cgttgccggg tacaagtgca actgcctgct gccctacaca ggtgccacgt   720
gtgaggtggt gctggccccg tgtgccccca gcccctgcag aaacggcggg gagtgcaggc   780
aatccgagga ctatgagagt tgtcactatg tcct                              814
```

<210> SEQ ID NO 14
<211> LENGTH: 799
<212> TYPE: PRT
<213> ORGANISM: Homo sapiens

<400> SEQUENCE: 14

```
Leu Ser Arg Lys Arg Arg Arg Gln His Gly Gln Leu Trp Phe Pro Glu
 1               5                   10                  15

Gly Phe Lys Val Ser Glu Ala Ser Lys Lys Arg Arg Glu Pro Leu
                20                  25                  30

Gly Glu Asp Ser Val Gly Leu Lys Pro Leu Lys Asn Ala Ser Asp Gly
                35                  40                  45

Ala Leu Met Asp Asp Asn Gln Asn Glu Trp Gly Asp Glu Asp Leu Glu
        50                  55                  60

Thr Lys Lys Phe Arg Phe Glu Glu Pro Val Val Leu Pro Asp Leu Asp
65                  70                  75                  80

Asp Gln Thr Asp His Arg Gln Trp Thr Gln Gln His Leu Asp Ala Ala
                85                  90                  95

Asp Leu Arg Met Ser Ala Met Ala Pro Thr Pro Pro Gln Gly Glu Val
            100                 105                 110

Asp Ala Asp Cys Met Asp Val Asn Val Arg Gly Pro Asp Gly Phe Thr
        115                 120                 125

Pro Leu Met Ile Ala Ser Cys Ser Gly Gly Gly Leu Glu Thr Gly Asn
    130                 135                 140

Ser Glu Glu Glu Glu Asp Ala Pro Ala Val Ile Ser Asp Phe Ile Tyr
145                 150                 155                 160

Gln Gly Ala Ser Leu His Asn Gln Thr Asp Arg Thr Gly Glu Thr Ala
                165                 170                 175

Leu His Leu Ala Ala Arg Tyr Ser Arg Ser Asp Ala Ala Lys Arg Leu
            180                 185                 190

Leu Glu Ala Ser Ala Asp Ala Asn Ile Gln Asp Asn Met Gly Arg Thr
        195                 200                 205

Pro Leu His Ala Ala Val Ser Ala Asp Ala Gln Gly Val Phe Gln Ile
    210                 215                 220

Leu Ile Arg Asn Arg Ala Thr Asp Leu Asp Ala Arg Met His Asp Gly
225                 230                 235                 240

Thr Thr Pro Leu Ile Leu Ala Ala Arg Leu Ala Val Glu Gly Met Leu
                245                 250                 255

Glu Asp Leu Ile Asn Ser His Ala Asp Val Asn Ala Val Asp Asp Leu
            260                 265                 270

Gly Lys Ser Ala Leu His Trp Ala Ala Ala Val Asn Asn Val Asp Ala
        275                 280                 285
```

```
Ala Val Val Leu Leu Lys Asn Gly Ala Asn Lys Asp Met Gln Asn Asn
    290                 295                 300
Arg Glu Glu Thr Pro Leu Phe Leu Ala Ala Arg Glu Gly Ser Tyr Glu
305                 310                 315                 320
Thr Ala Lys Val Leu Leu Asp His Phe Ala Asn Arg Asp Ile Thr Asp
                325                 330                 335
His Met Asp Arg Leu Pro Arg Asp Ile Ala Gln Glu Arg Met His His
            340                 345                 350
Asp Ile Val Arg Leu Leu Asp Glu Tyr Asn Leu Val Arg Ser Pro Gln
        355                 360                 365
Leu His Gly Ala Pro Leu Gly Gly Thr Pro Thr Leu Ser Pro Pro Leu
    370                 375                 380
Cys Ser Pro Asn Gly Tyr Leu Gly Ser Leu Lys Pro Gly Val Gln Gly
385                 390                 395                 400
Lys Lys Val Arg Lys Pro Ser Ser Lys Gly Leu Ala Cys Gly Ser Lys
                405                 410                 415
Glu Ala Lys Asp Leu Lys Ala Arg Arg Lys Lys Ser Gln Asp Gly Lys
            420                 425                 430
Gly Cys Leu Leu Asp Ser Ser Gly Met Leu Ser Pro Val Asp Ser Leu
        435                 440                 445
Glu Ser Pro His Gly Tyr Leu Ser Asp Val Ala Ser Pro Pro Leu Leu
    450                 455                 460
Pro Ser Pro Phe Gln Gln Ser Pro Ser Val Pro Leu Asn His Leu Pro
465                 470                 475                 480
Gly Met Pro Asp Thr His Leu Gly Ile Gly His Leu Asn Val Ala Ala
                485                 490                 495
Lys Pro Glu Met Ala Ala Leu Gly Gly Gly Arg Leu Ala Phe Glu
            500                 505                 510
Thr Gly Pro Pro Arg Leu Ser His Leu Pro Val Ala Ser Gly Thr Ser
        515                 520                 525
Thr Val Leu Gly Ser Ser Ser Gly Gly Ala Leu Asn Phe Thr Val Gly
    530                 535                 540
Gly Ser Thr Ser Leu Asn Gly Gln Cys Glu Trp Leu Ser Arg Leu Gln
545                 550                 555                 560
Ser Gly Met Val Pro Asn Gln Tyr Asn Pro Leu Arg Gly Ser Val Ala
                565                 570                 575
Pro Gly Pro Leu Ser Thr Gln Ala Pro Ser Leu Gln His Gly Met Val
            580                 585                 590
Gly Pro Leu His Ser Ser Leu Ala Ala Ser Ala Leu Ser Gln Met Met
        595                 600                 605
Ser Tyr Gln Gly Leu Pro Ser Thr Arg Leu Ala Thr Gln Pro His Leu
    610                 615                 620
Val Gln Thr Gln Gln Val Gln Pro Gln Asn Leu Gln Met Gln Gln Gln
625                 630                 635                 640
Asn Leu Gln Pro Ala Asn Ile Gln Gln Gln Gln Ser Leu Gln Pro Pro
                645                 650                 655
Pro Pro Pro Pro Gln Pro His Leu Gly Val Ser Ser Ala Ala Ser Gly
            660                 665                 670
His Leu Gly Arg Ser Phe Leu Ser Gly Glu Pro Ser Gln Ala Asp Val
        675                 680                 685
Gln Pro Leu Gly Pro Ser Ser Leu Ala Val His Thr Ile Leu Pro Gln
    690                 695                 700
```

-continued

```
Glu Ser Pro Ala Leu Pro Thr Ser Leu Pro Ser Ser Leu Val Pro Pro
705                 710                 715                 720

Val Thr Ala Ala Gln Phe Leu Thr Pro Pro Ser Gln His Ser Tyr Ser
                725                 730                 735

Ser Pro Val Asp Asn Thr Pro Ser His Gln Leu Gln Val Pro Glu His
            740                 745                 750

Pro Phe Leu Thr Pro Ser Pro Glu Ser Pro Asp Gln Trp Ser Ser Ser
        755                 760                 765

Ser Pro His Ser Asn Val Ser Asp Trp Ser Glu Gly Val Ser Ser Pro
        770                 775                 780

Pro Thr Ser Met Gln Ser Gln Ile Ala Arg Ile Pro Glu Ala Phe
785                 790                 795
```